(12) United States Patent
Cizeron et al.

(10) Patent No.: US 10,927,056 B2
(45) Date of Patent: Feb. 23, 2021

(54) REACTORS AND SYSTEMS FOR OXIDATIVE COUPLING OF METHANE

(71) Applicant: Lummus Technology LLC, The Woodlands, TX (US)

(72) Inventors: Joel Cizeron, Redwood City, CA (US); Guido Radaelli, South San Francisco, CA (US); Satish Lakhapatri, Mountain View, CA (US); Erik Freer, Mountain View, CA (US); Jin Ki Hong, Moraga, CA (US); Jarod McCormick, San Carlos, CA (US); David Sheridan, Menlo Park, CA (US); Charles Reid, Berkeley, CA (US); Roberto Pellizzari, Groton, MA (US); Samuel Weinberger, San Francisco, CA (US); Justin Dwight Edwards, Pacifica, CA (US)

(73) Assignee: Lummus Technology LLC, The Woodlands, TX (US)

( * ) Notice: Subject to any disclaimer, the term of this patent is extended or adjusted under 35 U.S.C. 154(b) by 0 days.

(21) Appl. No.: 16/290,689

(22) Filed: Mar. 1, 2019

(65) Prior Publication Data

US 2020/0031734 A1    Jan. 30, 2020

Related U.S. Application Data

(63) Continuation of application No. 16/035,311, filed on Jul. 13, 2018, now abandoned, which is a
(Continued)

(51) Int. Cl.
*B01J 8/00* (2006.01)
*C07C 2/78* (2006.01)
(Continued)

(52) U.S. Cl.
CPC .............. *C07C 2/78* (2013.01); *B01J 8/0214* (2013.01); *B01J 8/0278* (2013.01); *B01J 8/1827* (2013.01);
(Continued)

(58) Field of Classification Search
CPC .. C07C 2/84; C07C 11/04; C07C 2/78; C07C 9/06; C07C 1/02; C07C 2523/10;
(Continued)

(56) References Cited

U.S. PATENT DOCUMENTS 2,324,172 A     7/1943  Parkhurst
2,486,980 A    11/1949  Robinson
(Continued)

FOREIGN PATENT DOCUMENTS

CA         2041874 C     4/1999
CA         2765769 A1    1/2011
(Continued)

OTHER PUBLICATIONS

Witek-Krowiak, A. et al. Carbon Dioxide Removal in a Membrane Contactor-Selection of Absorptive Liquid/Membrane System. Intl J Chem Eng and Appl. (2012) 3(6):391-395.
(Continued)

*Primary Examiner* — Sharon Pregler
(74) *Attorney, Agent, or Firm* — Calfee, Halter & Griswold LLP

(57) ABSTRACT

In an aspect, the present disclosure provides a method for the oxidative coupling of methane to generate hydrocarbon compounds containing at least two carbon atoms ($C_{2+}$ compounds). The method can include mixing a first gas stream comprising methane with a second gas stream comprising oxygen to form a third gas stream comprising methane and oxygen and performing an oxidative coupling of methane (OCM) reaction using the third gas stream to
(Continued)

produce a product stream comprising one or more $C_{2+}$ compounds.

20 Claims, 50 Drawing Sheets

Related U.S. Application Data continuation of application No. 14/553,795, filed on Nov. 25, 2014, now Pat. No. 10,047,020.

(60) Provisional application No. 61/909,955, filed on Nov. 27, 2013, provisional application No. 61/909,980, filed on Nov. 27, 2013.

(51) Int. Cl.
    *B01J 8/18*         (2006.01)
    *B01J 8/02*         (2006.01)
    *C07C 2/84*        (2006.01)

(52) U.S. Cl.
CPC .......... *C07C 2/84* (2013.01); *B01J 2208/0053* (2013.01); *B01J 2208/0092* (2013.01); *B01J 2208/00132* (2013.01); *B01J 2208/00309* (2013.01); *B01J 2208/00495* (2013.01); *B01J 2208/00849* (2013.01); *B01J 2208/00902* (2013.01); *B01J 2208/00938* (2013.01); *B01J 2208/025* (2013.01); *Y02P 20/52* (2015.11)

(58) Field of Classification Search
CPC ... C07C 9/04; C07C 2521/04; C07C 2521/06; C07C 2521/10; C07C 2523/02; C07C 2523/04; C07C 2523/46; C07C 2523/652; C07C 2523/755; C07C 2523/888; B01J 8/0214; B01J 8/0278; B01J 8/1827; B01J 23/34; B01J 12/007; B01J 19/2485; B01J 19/26; B01J 21/08; B01J 2219/0025; B01J 23/002; B01J 23/10; B01J 23/20; B01J 8/043; B01J 8/0492
See application file for complete search history.

(56) References Cited

U.S. PATENT DOCUMENTS

| | | |
|---|---|---|
| 2,577,701 A | 12/1951 | Deming et al. |
| 2,579,601 A | 12/1951 | Nelson et al. |
| 2,621,216 A | 12/1952 | White |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Tudor |
| 3,128,317 A | 4/1964 | Arkell et al. |
| 3,325,556 A | 6/1967 | De Rosset |
| 3,413,817 A | 12/1968 | Ludwig |
| 3,459,678 A | 8/1969 | Hagemeyer, Jr. et al. |
| 3,584,071 A | 6/1971 | McNulty et al. |
| 3,596,473 A | 8/1971 | Streich |
| 3,660,519 A | 5/1972 | Arakawa et al. |
| 3,686,334 A | 8/1972 | Britton |
| 3,686,350 A | 8/1972 | Ono et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,891,457 A | 1/1990 | Owen et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |

(56) References Cited

U.S. PATENT DOCUMENTS

| | | |
|---|---|---|
| 5,196,634 A | 3/1993 | Washecheck et al. |
| 5,198,596 A | 3/1993 | Kaminsky et al. |
| 5,240,474 A | 8/1993 | Auvil et al. |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | deVries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Truebenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,342,149 B1 | 1/2002 | Koster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |

(56) References Cited

U.S. PATENT DOCUMENTS

| | | |
|---|---|---|
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 * | 3/2012 | Bagherzadeh ........... B01J 37/03 502/313 |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild Hansen |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 | 9/2019 | Radaelli et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1 | 6/2008 | Bozzano et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2010/0000153 A1 | 1/2010 | Kurkjian et al. |
| 2010/0003179 A1 | 1/2010 | Katusic et al. |

(56) References Cited

U.S. PATENT DOCUMENTS

| | | |
|---|---|---|
| 2010/0028735 A1 | 2/2010 | Basset et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2013/0023079 A1 | 1/2013 | Kang et al. |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |
| 2020/0031736 A1 | 1/2020 | Weinberger et al. |
| 2020/0048165 A1 | 2/2020 | Duggal et al. |
| 2020/0055796 A1 | 2/2020 | Nyce et al. |
| 2020/0071242 A1 | 3/2020 | Patel et al. |
| 2020/0172452 A1 | 6/2020 | Duggal et al. |
| 2020/0189994 A1 | 6/2020 | Radaelli et al. |

FOREIGN PATENT DOCUMENTS

| | | |
|---|---|---|
| CA | 2800142 C | 6/2018 |
| CN | 1403375 A | 3/2003 |
| CN | 101224432 A | 7/2008 |
| CN | 101387019 A | 3/2009 |
| CN | 101747927 A | 6/2010 |
| CN | 102093157 A | 6/2011 |

(56) References Cited

FOREIGN PATENT DOCUMENTS

| | | |
|---|---|---|
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 253522 A2 | 1/1988 |
| EP | 303438 A2 | 2/1989 |
| EP | 336823 A1 | 10/1989 |
| EP | 608447 A1 | 8/1994 |
| EP | 634211 A1 | 1/1995 |
| EP | 722822 A1 | 7/1996 |
| EP | 761307 A1 | 3/1997 |
| EP | 764467 A1 | 3/1997 |
| EP | 716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | 8607351 A1 | 12/1986 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 A2 | 7/2005 |
| WO | 2007125360 A1 | 11/2007 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2008150451 A2 | 12/2008 |
| WO | 2008150451 A3 | 3/2009 |
| WO | 2009071463 A2 | 6/2009 |
| WO | 2009074203 A1 | 6/2009 |
| WO | 2009115805 A1 | 9/2009 |
| WO | 2010005453 A2 | 1/2010 |
| WO | 2011008464 A1 | 1/2011 |
| WO | 2011041184 A2 | 4/2011 |
| WO | 2011050359 A1 | 4/2011 |
| WO | 2010069488 A8 | 5/2011 |
| WO | 2011149996 A2 | 12/2011 |
| WO | 2012047274 A2 | 4/2012 |
| WO | 2012047274 A3 | 5/2012 |
| WO | 2012162526 A2 | 11/2012 |
| WO | 2013106771 A2 | 7/2013 |
| WO | 2013169462 A1 | 11/2013 |
| WO | 2013175204 A1 | 11/2013 |
| WO | 2013177433 A2 | 11/2013 |
| WO | 2013177461 A2 | 11/2013 |
| WO | 2014011646 A1 | 1/2014 |
| WO | 2014044387 A1 | 3/2014 |
| WO | 2014049445 A2 | 4/2014 |
| WO | 2014089479 A1 | 6/2014 |
| WO | 2013177433 A3 | 8/2014 |
| WO | 2014131435 A1 | 9/2014 |
| WO | 2014143880 A1 | 9/2014 |
| WO | 2015000061 A1 | 1/2015 |
| WO | 2015003193 A2 | 1/2015 |
| WO | 2015021177 A1 | 2/2015 |
| WO | 2015048295 A1 | 4/2015 |
| WO | 2015066693 A1 | 5/2015 |
| WO | 2015081122 A2 | 6/2015 |
| WO | 2015105911 A1 | 7/2015 |
| WO | 2015106023 A1 | 7/2015 |
| WO | 2015081122 A3 | 12/2015 |
| WO | 2016012371 A1 | 1/2016 |
| WO | 2016149507 A1 | 9/2016 |
| WO | 2016160563 A1 | 10/2016 |
| WO | 2016205411 A2 | 12/2016 |
| WO | 2016210006 A2 | 12/2016 |
| WO | 2016210006 A3 | 4/2017 |
| WO | 2017065947 A1 | 4/2017 |
| WO | 2016205411 A3 | 9/2017 |
| WO | 2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | 2018118105 A1 | 6/2018 |
| WO | 2019010498 A1 | 1/2019 |
| WO | 2019055220 A1 | 3/2019 |

OTHER PUBLICATIONS

Wong, et al. Oxidative coupling of methane over alkali metal oxide promoted La2 03/BaCO3 catalysts. J. Chem. Tech. Biotechnol. 65:351-354, 1996.

Wu, et al., High-Capacity Methane Storage in Metal-Organic Frameworks M2(dhtp): The Important Role of Open Metal Sites, J. Am. Chem. Soc. 131 (13):4995-5000.

Xu, et al. Maximise ethylene gain and acetylene selective hydrogenation efficiency. Petroleum technology quarterly 18.3 (2013): 39-42.

Xu, G. et al. An Improved CO2 Separation and Purification System Based on Cryogenic Separation and Distillation Theory. Energies (2014) 7:3484-3502.

Yan, D. Modeling and Application of a Thermoelectric Generator. Thesis, Univ. Toronto (2011).

Yang, et al. Anistropic synthesis of boat shaped core shell Au-Ag nanocrystals and nanowires. Nanotechnology 17:2304-2310, 2006.

Yu, et al. Oxidative coupling of methane over acceptor-doped SrTi 03: Correlation between p-type conductivity and C2 selectivity and C2 yield. Journal of Catalysis. 13 (5): 338-344, 1992.

Zhang, Q. Journal of Natural Gas Chem., 12:81, 2003.

Zhao, et al. Technologies and catalysts for catalytic preparation of ethene. Industrial catalysis 12 (Supplement): 285-289, 2004.

Zhou, et al. Functionalization of lanthanum hydroxide nanowires by atom transfer radical polymerization. Nanotechnology 18, 2007, 7 pages.

Zhou. BP-UOP Cyclar Process. Handbook of Petroleum Refining Processes, The McGraw-Hill Companies (2004), pp. 2.29-2.38.

Zhou, et al., Enhanced H2 Adsorption in Isostructural Metal-Organic Frameworks with Open Metal Sites: Strong Dependence of the Binding Strength on Metal Ions, J. Am. Chem. Soc., 2008, 130(46):15268-69.

Zimmerman, et al. Ethylene. Ulmann's Encyclopedia of Inudstrial Chemisty, Wiley-VCH Verlag GmbH & Co. KGaA, Weinheim, Germany, 2009, 66 pages.

International search report and written opinion dated Nov. 11, 2015 for PCT Application No. PCT/US2014/067465.

Office action dated Oct. 27, 2017 for U.S. Appl. No. 14/553,795.

U.S. Appl. No. 14/553,795 Notice of Allowance dated May 25, 2018.

Supplementary European search report dated Jun. 27, 2017 for EP Application No. 14866399.0.

Examination Report dated Jul. 24, 2017 for EP Application No. 14866399.0.

Examination Report dated Mar. 12, 2018 for EP Application No. 14866399.0.

Ling, et al. Preparation of Ag core Au shell Nanowires and Their Surface Enhanced Raman Spectroscopic Studies. Acta Chimica Sinica. 65 (9): 779-784, 2007.

Liu, et al. A novel Na2 W04-Mn.SiC monolithic foam catalyst with improved thermal properties for the oxidative coupling of methane. Catalysis Communications 9: 1302-1306, 2008.

Liu, et al. Increasing the Density of Adsorbed Hydrogen with

(56) References Cited

OTHER PUBLICATIONS

Coordinatively Unsaturated Metal Centers in Metal-Organic Frameworks Langmuir, 2008, 24:4772-77.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Lunsford, et al. The oxidative coupling of methane on chlorinated Lithium-doped magnesium oxide. J. Chem. Soc., Chem. Commun., 1991, 1430-1432.
Makal, et al., Methane storage in advanced porous materials, Critical Review, Chem. Soc. Rev., 2012, 41 :7761-7779.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Mokhatab et al. "Handbook of Natural Gas Transmission and Processing: Principles and Practices" 2015. Chapter 7, pp. 237-242. (Year 2015).
Morgan, C.R. et al. Gasoline from Alcohols. Ind Eng Chem Prod Res Dev(1981) 20:185-190.
Natural Gas Spec Sheet, 2003, prepared by Florida Power and Light Company.
Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Niu, et al. Preparation and characterization of La2 O3CO3 nanowires with high surface areas. Jounral of the Chinese Rare Earth Society 23 (Spec. Issue): 33-36, Dec. 2005.
Ogura et al. Formation of Uniform Mesopores in ZSM-5 Zeolite through Treatment in Alkaline Solution, Chemistry Letters, 2000, pp. 882-883.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Olefins Conversion Technology, Website Accessed Aug. 28, 2014, http:www.CBI.com.
Pak, et al. Elementary Reactions in the Oxidative Coupling of Methane over Mn/NA2 W04/Si02 and MN/NA2 W04/Mg0 Catalysts. Journal of Catalysis 179:222-230, 1998.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.

Process Systems; "Steam Tables" Apr. 8, 2017—https://web.archive.org/web/20170408152403/https://valvesonline.com.au/references/steamtables/.
Qiu, et al. Steady-state conversion of methane to aromatics in high yields using an integrated recycle reaction system. Catalysis Letters 48: 11-15, 1997.
Rousseau, Handbook of Separation Process Technology, 1987, p. 682.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK—Conference, Hamburg, Germany (2007).
Simons, K. Membrane Technologies for CO2 Capture. Dissertation, U. of Twente (2010).
Smith, et al. Recent developments in solvent absorption technologies at the CO2CRC in Australia. Energy Procedia 1(2009): 1549-1555.
Somorjai, et al. High technology catalysts towards 100% selectivity Fabrication, characterization and reaction studies. Catalysis today 100:201-215, 2005.
Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Tabak, S.A. et al. Conversion of Methanol over ZSM-5 to Fuels and Chemicals. Cat Today (1990) 307-327.
Takanabe, et al. Mechanistic Aspects and Reaction Pathways for Oxidative Coupling of Methane on Mn/NA2 W04/Si02 Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by Mn/NA2 W04/SiO2 . Angewandte Chemie International Edition 47:7689-7693, 2008.
Tong, et al. Development strategy research of downstream products of ethene in Tianjin. Tianjin Economy, pp. 37-40,1996.
Trautmann, et al. Cryogenic technology for nitrogen rejection from variable content natural gas. Presented at the XIV Convencion Internacional de Gas, Caracas, Venezuela, May 10-12, 2000, 13 pages.
Wang, et al. Autothermal oxidative coupling of methane on the SrCO3/Sm2 03 catalysts. Catalysis communications 10: 807-810, 2009.
Wang, et al. Comparative study on oxidation of methane to ethane and ethylene over NA2 W04-Mn/SiO2 catalysts prepared by different methods. Journal of Molecular Catalysis A: Chemical 245:272-277, 2006.
Wang, et al. Low temperature selective oxidation of methane to ethane and ethylene over BaCO3/La2 03 catalysts prepared by urea combustion method. Catalysis communications 7: 5963, 2006.
Wang, et al., Critical Influence of BaCO3 on Low Temperature Catalytic Activity of BaCO3/Zr02 Catalysts for Oxidative Coupling of Methane, Catalysis Letters (2009), 129:156-162.
Water Electrolysis & Renewable Energy Systems. FuelCellToday (May 2013).
Wikipedia search, Adiabatic Process, Mar. 2011, 10 pages.
Agarwal, et al., Aqueous Au-Pd colloids catalyze selective CH4 oxidation to CH3OH with O2 under mild conditions, Science 358, Oct. 13, 2017, 223-27.
Ahari, et al. Effects of operating parameters on oxidative coupling of methane over Na-WMn/SiO2 catalyst at elevated pressures. Journal of Natural Gas Chemistry. vol. 20, Issue 2, Mar. 2011, pp. 204-213.
American Petroleum Institute Publication 534 Heat Recovery Steam Generators Jan. 1995 (51 pages).
Autothermal Partial Oxidative Coupling of Methane. IP.com, Prior Art Database Technical Disclosure, Jul. 29, 2008, 5 pages.

(56) References Cited

OTHER PUBLICATIONS

Barrett, et al. The determination of pore volume and area distributions in porous substances—Compuatations from nitrogen isotherms. J. Am. Chem. Soc., 1951, vol. 73, pp. 373-380.
Berstad, D. et al. Low-temperature $CO_2$ removal from natural gas. Energy Procedia (2012) 26:41-48.
Bloch, et al. Hydrocarbon Separations in a Metal-Organic Framework with Open Iron(II) Coordination Sites, Science, 2012, 335:1606-1610.
Bollmann, et al. Ethylene tetramerization: a new route to produce 1-octene in exceptionally high selectivities. J Am Chem Soc. Nov. 17, 2004;126(45):14712-3.
Botella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.
Carter, et al. High activity ethylene trimerisation catalysts based on diphosphine ligands. Chem Commun (Camb). Apr. 21, 2002;(8):858-9.
Caskey, et al., Dramatic Tuning of Carbon Dioxide Uptake via Metal Substitution in a Coordination Polymer with Cylindrical Pores, J. Am. Chem. Soc., (2009), 130(33): 10870-71.
Cavani, et al. Oxidative dehydrogenation of ethane and propane: How far from commercial implementation? Catalysis Today. 2007; 127(1-4):113-131.
Chemsystems PERP Report Ethylene Oxide/Ethylene Glycol 2005.
Chen, et al. M2 Forming—A Process for Aromatization of Light Hydrocarbons. Ind. Eng. Chem. Process. Des. Dev. 1986, 25, 151-155.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): 15-25, Feb. 2004.
Choudhary, et al. Surface Basicity and Acidity of Alkaline Earth-Promoted $La_2O_3$ Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Corma, From Microporous to Mesoporous Molecular Sieve Materials and Their Use in Catalysis, Chern. Rev., 97, 1997, pp. 2373-2419.
Debart, et al. $\alpha$-$MNO_2$ Nanowires: a catalyst for the $O_2$ Electrode in Rechargeabl Lithium Batteries. Angewandte Chemie International Edition 47: 4521-4524, 2008.
Dietzel, et al., Adsorption properties and structure of $CO_2$ adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009)18:156-160.
Enger, et al. A review of catalytic partial oxidation of methane to synthesis gas with emphasis on reaction mechanisms over transition metal catalysts. Applied Catalysis A: General 346 (1-2): 1-27, Aug. 2008.
Fallah, et al., A New Nano-(2Li2O/MgO) Catalyst/Porous Alpha-Alumina Composite for the Oxidative Coupling of Methane Reaction, AIChE Journal, Mar. 2010, 56(3):717-28.
Gao, et al. A study on methanol steam reforming to $CO_2$ and $H_2$ over the $La_2CO_4$ nanofiber catalyst. Journal of Solid State Chemistry 181: 7-13, 2008.
Gao, et al. The direct decomposition of NO over the $La_2CuO_4$ nanofiber catalyst. Journal of Solid State Chemistry 181: 2804-2807, 2008.

Geier, et al., Selective adsorption of ethylene over ethane and propylene over propane in the metal-organic frameworks M2(dobdc) (M=Mg, Mn, Fe, Co, Ni, Zn), Chem. Sci., 2013, 4:2054-2061.
Ghosh, et al., Absorption of carbon dioxide into aqueous potassium carbonate promoted by boric acid, Energy Procedia, Feb. 2009, pp. 1075-1081.
Godini, et al. Techno-economic analysis of integrating the methane oxidative coupling and methane reforming processes. Fuel processing technology 2013 v.106 pp. 684-694.
Goto et al, Mesoporous Material from Zeolite, Journal of Poruous Materials, 2002, pp. 43-48.
Graves, C.R. Recycling $CO_2$ into Sustainable Hydrocarbon Fuels: Electrolysis of $CO_2$ and $H_2O$. Dissertation, Columbia University (2010).
Guo, et al. Current Status and Some Perspectives of Rare Earth Catalytic Materials. Journal of the Chinese Rare Earth Society 25(1): 1-15, Feb. 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4 (4):128-131.
Haag, W.O. et al. Aromatics, Light Olefins and Gasoline from Methanol: Mechanistic Pathways with ZSM-5 Zeolite Catalyst. J Mol Catalysis (1982) 17:161-169.
Hosseinpour, Performance of CaX Zeolite for Separation of $C_2H_6$, $C_2H_4$, and $CH_4$ by Adsorption Process; Capacity, Selectivity, and Dynamic Adsorption Measurements, Separation Science and Technology, 2011, 46:349-355.
Huang, et al. Exploiting shape effects of $La_2O_3$ nanocrystals for oxidative coupling of methane reaction. Nanoscale 5 (22): 10844-10848, 2013.
Huang, et al. Exploiting shape effects of $La_2O_3$ nanocrystals for oxidative coupling of methane reaction. Nanoscale—Electronic Supplementary Material, 2013, 7 pages.
Iwamoto, M. One step formation of propene from ethene or ethanol through metathesis on nickel ion-loaded silica. Molecules. Sep. 13, 2011;16(9):7844-63.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, Gas-Adsorption Processes: State of the Art, American Chemical Society, 1983,pp. 145-169.
Keller, et al. Synthesis of Ethylene via Oxidative Coupling of Methane. Journal of Catalysis 73: 9-19, 1982.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Labinger. Oxidative coupling of methane: an inherent limit to selectivity? Catal. Lett. 1988; 1:371-376.
Li, B. et al. Advances in $CO_2$ capture technology: A patent review. Applied Energy (2013) 102:1439-1447.
Li, et al. Combined Single-Pass Conversion of Methane via Oxidative Coupling and Dehydroaromatization. Catalysis Letters, Sep. 2003, vol. 89, Issue 3-4, pp. 275-279.
Li, et al. Energy and Fuels. 2008, 22: 1897-1901.
Zimmerman, et al. Ethylene Ulmann's Encyclopedia of lnudstrial Chemisty, Wiley-VCH Verlag GmbH & Co. KGaA, Weinheim, Germany, 2009, 66 pages.

\* cited by examiner

REACTORS AND SYSTEMS FOR OXIDATIVE COUPLING OF METHANE

CROSS-REFERENCE

This application is a continuation of U.S. patent application Ser. No. 16/035,311, filed Jul. 13, 2018, which is a continuation of U.S. patent application Ser. No. 14/553,795, filed Nov. 25, 2014, now U.S. Pat. No. 10,047,020, which claims priority to U.S. Provisional Patent Application No. 61/909,955, filed Nov. 27, 2013, and U.S. Provisional Patent Application No. 61/909,980, filed Nov. 27, 2013, each of which is entirely incorporated herein by reference.

BACKGROUND

The modern petrochemical industry makes extensive use of cracking and fractionation technology to produce and separate various desirable compounds from crude oil. Cracking and fractionation operations are energy intensive and generate considerable quantities of greenhouse gases.

The gradual depletion of worldwide petroleum reserves and the commensurate increase in petroleum prices may place extraordinary pressure on refiners to minimize losses and improve efficiency when producing products from existing feedstocks, and also to seek viable alternative feedstocks capable of providing affordable hydrocarbon intermediates and liquid fuels to downstream consumers.

Methane may provide an attractive alternative feedstock for the production of hydrocarbon intermediates and liquid fuels due to its widespread availability and relatively low cost when compared to crude oil. Worldwide methane reserves may be in the hundreds of years at current consumption rates and new production stimulation technologies may make formerly unattractive methane deposits commercially viable.

Ethylene is an important commodity chemical intermediate. It may be used in the production of polyethylene plastics, polyvinyl chloride, ethylene oxide, ethylene chloride, ethylbenzene, alpha-olefins, linear alcohols, vinyl acetate, and fuel blendstocks such as, but not limited to, aromatics, alkanes, and alkenes. With economic growth in developed and developing portions of the world, demand for ethylene and ethylene based derivatives continues to increase. Currently, ethylene is produced through the cracking of ethane derived either from crude oil distillates, called naphtha, or from the relatively minor ethane component of natural gas. Ethylene production is primarily limited to high volume production as a commodity chemical in relatively large steam crackers or other petrochemical complexes that also process the large number of other hydrocarbon byproducts generated in the crude oil cracking process. Producing ethylene from far more abundant and significantly less expensive methane in natural gas provides an attractive alternative to ethylene derived from ethane in natural gas or crude oil. Oligomerization processes can be used to further convert ethylene into longer chain hydrocarbons useful as polymer components for plastics, vinyls, and other high value polymeric products. Additionally, these oligomerization processes may be used to convert ethylene to other longer hydrocarbons, such as $C_6$, $C_7$, $C_8$ and longer hydrocarbons useful for fuels like gasoline, diesel, jet fuel and blendstocks for these fuels, as well as other high value specialty chemicals.

SUMMARY

Recognized herein is the need for systems and methods for converting methane to higher chain hydrocarbons, such as hydrocarbon compounds with two or more carbon atoms (also "$C_{2+}$ compounds" herein), in an efficient and/or commercially viable process. An oxidative coupling of methane ("OCM") reaction is a process by which methane can form one or more $C_{2+}$ compounds.

The present disclosure provides reactors, systems and methods that can be used to react methane in an OCM process to yield products comprising $C_{2+}$ compounds. OCM reactors, systems and methods of the present disclosure can be integrated in various hydrocarbon processes. The efficient and/or commercially viable formation of $C_{2+}$ compounds from methane can be influenced by a number of different parameters that can both affect the progress of the overall reaction of methane to ethylene, as well as provide opportunities for efficiency outside of the reaction progress, e.g., through energy efficient processes and systems, recycling opportunities and the like.

An aspect of the present disclosure provides a method for the oxidative coupling of methane to generate hydrocarbon compounds containing at least two carbon atoms ($C_{2+}$ compounds), comprising: (a) mixing a first gas stream comprising methane with a second gas stream comprising oxygen to form a third gas stream comprising methane and oxygen, wherein (i) the temperature variation of said third gas stream is less than about 10° C., (ii) the variation of the concentration of methane to the concentration of oxygen ($CH_4/O_2$) in said third gas stream is less than about 10%, and/or (iii) the variation of the flow rate of said third gas stream is less than about 5%; and (b) performing an oxidative coupling of methane (OCM) reaction using said third gas stream to produce a product stream comprising one or more $C_{2+}$ compounds.

In some embodiments of aspects provided herein, the method further comprises separating said product stream into at least a fourth stream and a fifth stream, wherein said fourth stream has a lower $C_{2+}$ concentration than said fifth stream, wherein said fifth stream has a higher $C_{2+}$ concentration than said product stream. In some embodiments of aspects provided herein, (a) comprises any two of (i)-(iii). In some embodiments of aspects provided herein, wherein (a) comprises (i), (ii) and (iii).

An aspect of the present disclosure provides a method for the oxidative coupling of methane to generate hydrocarbon compounds containing at least two carbon atoms ($C_{2+}$ compounds), comprising: (a) in a mixer, mixing a first gas stream comprising methane with a second gas stream comprising oxygen to form a third gas stream comprising methane and oxygen, wherein said third gas stream has a composition that is selected such that at most 5% of said oxygen in said third gas stream auto-ignites; and (b) performing an oxidative coupling of methane (OCM) reaction using said third gas stream to produce a product stream comprising one or more $C_{2+}$ compounds.

In some embodiments of aspects provided herein, the method further comprises separating said product stream into at least a fourth stream and a fifth stream, wherein said fourth stream has a lower $C_{2+}$ concentration than said fifth stream, wherein said fifth stream has a higher $C_{2+}$ concentration than said product stream. In some embodiments of aspects provided herein, the composition of said third gas stream is selected such that at most 1% of said oxygen in said third gas stream auto-ignites. In some embodiments of aspects provided herein, the composition of said third gas stream is selected such that at most 0.1% of said oxygen in said third gas stream auto-ignites. In some embodiments of aspects provided herein, the composition of said third gas stream is selected such that substantially no oxygen in said third gas stream auto-ignites. In some embodiments of aspects provided herein, said mixer comprises one or more airfoil-shaped manifolds.

An aspect of the present disclosure provides a method for the oxidative coupling of methane to generate hydrocarbon compounds containing at least two carbon atoms ($C_{2+}$ compounds), comprising: (a) in a mixer, mixing a first gas stream comprising methane with a second gas stream comprising oxygen to form a third gas stream comprising methane and oxygen, wherein said third gas stream has a substantially non-symmetric distribution of residence times along a direction of flow of said third stream; and (b) performing an oxidative coupling of methane (OCM) reaction using said third gas stream to produce a product stream comprising one or more $C_{2+}$ compounds.

In some embodiments of aspects provided herein, the method further comprises separating said product stream into at least a fourth stream and a fifth stream, wherein said fourth stream has a lower $C_{2+}$ concentration than said fifth stream, wherein said fifth stream has a higher $C_{2+}$ concentration than said product stream. In some embodiments of aspects provided herein, said OCM reaction is performed in an OCM reactor downstream of said mixer. In some embodiments of aspects provided herein, at least a portion of said OCM reaction is performed in said mixer. In some embodiments of aspects provided herein, said distribution of residence times is selected such that greater than 95% of said third stream spends less than an auto-ignition delay time in said mixer. In some embodiments of aspects provided herein, said distribution of residence times is selected such that greater than 99% of said third stream spends less than an auto-ignition delay time in said mixer. In some embodiments of aspects provided herein, said distribution of residence times is selected such that greater than 99.9% of said third stream spends less than an auto-ignition delay time in said mixer. In some embodiments of aspects provided herein, said mixer comprises one or more airfoil-shaped manifolds.

An aspect of the present disclosure provides a method for the oxidative coupling of methane to generate hydrocarbon compounds containing at least two carbon atoms ($C_{2+}$ compounds), the method comprising: (a) in a mixer, mixing a first gas stream comprising methane with a second gas stream comprising oxygen to form a third gas stream comprising methane and oxygen; and (b) within a time period less than an auto-ignition delay time of oxygen and methane in said third gas stream, performing an oxidative coupling of methane (OCM) reaction using said third gas stream to produce a product stream comprising one or more $C_{2+}$ compounds.

In some embodiments of aspects provided herein, the method further comprises separating said product stream into at least a fourth stream and a fifth stream, wherein said fourth stream has a lower $C_{2+}$ concentration than said fifth stream, wherein said fifth stream has a higher $C_{2+}$ concentration than said product stream. In some embodiments of aspects provided herein, said auto-ignition delay time is from about 20 milliseconds (ms) to 500 ms at a pressure from about 1 bar (absolute) and 30 bars and a temperature from about 400° C. and 750° C. In some embodiments of aspects provided herein, said mixer comprises one or more airfoil-shaped manifolds.

An aspect of the present disclosure provides a method for the oxidative coupling of methane to generate hydrocarbon compounds containing at least two carbon atoms ($C_{2+}$ compounds), the method comprising: (a) in a mixer, mixing a first gas stream comprising methane with a second gas stream comprising oxygen to form a third gas stream comprising methane and oxygen, wherein upon said mixing, flow separation does not occur between said mixer and said first gas stream, said second gas stream, and/or said third gas stream; and (b) performing an oxidative coupling of methane (OCM) reaction using said third gas stream to produce a product stream comprising one or more $C_{2+}$ compounds.

In some embodiments of aspects provided herein, the method further comprises separating said product stream into at least a fourth stream and a fifth stream, wherein said fourth stream has a lower $C_{2+}$ concentration than said fifth stream, wherein said fifth stream has a higher $C_{2+}$ concentration than said product stream. In some embodiments of aspects provided herein, said mixer comprises one or more airfoil-shaped manifolds.

An aspect of the present disclosure provides a method for flame-less auto-thermal reforming (ATR) to generate syngas, the method comprising: (a) mixing a first gas stream comprising methane with a second gas stream comprising oxygen to form a third gas stream; and (b) prior to auto-ignition of said third gas stream, performing a flame-less auto-thermal reforming (ATR) reaction using said third gas stream to produce a product stream comprising hydrogen ($H_2$) and carbon monoxide (CO).

An aspect of the present disclosure provides a system for mixing two or more gas streams, comprising: (a) a conduit comprising a fluid flow path for a first gas; (b) a plurality of airfoil-shaped manifolds distributed across said fluid flow path, wherein each of said airfoil-shaped manifolds comprises one or more openings that inject a second gas into said fluid flow path such that said first gas and second gas become uniformly mixed; and (c) a reactor bed in fluid communication with said fluid flow path, wherein said reactor bed comprises an oxidative coupling of methane catalyst.

In some embodiments of aspects provided herein, said manifolds prevent flow separation within said mixer. In some embodiments of aspects provided herein, said manifolds mix said first gas and said second gas within about 200 milliseconds. In some embodiments of aspects provided herein, said reactor bed is in contact with at least a portion of said manifolds. In some embodiments of aspects provided herein, each of said airfoil-shaped manifolds comprises a first end and a second end situated along said fluid flow path, wherein said one or more openings are disposed between said first end and said second end.

An aspect of the present disclosure provides a reactor system for performing oxidative coupling of methane to generate hydrocarbon compounds containing at least two carbon atoms ($C_{2+}$ compounds), comprising: (a) a mixer comprising (i) a conduit providing a fluid flow path for a first gas stream comprising methane and (ii) a plurality of airfoil-shaped manifolds distributed across said fluid flow path, wherein said airfoil-shaped manifolds inject a second gas stream comprising oxygen into said fluid flow path to provide a third gas stream comprising methane and oxygen; and (b) a catalyst that performs an oxidative coupling of methane (OCM) reaction using said third gas stream to produce a product stream comprising one or more $C_{2+}$ compounds.

In some embodiments of aspects provided herein, said airfoil-shaped manifolds are in contact with said catalyst. In some embodiments of aspects provided herein, said reactor comprises at least two stages of mixer and catalyst. In some embodiments of aspects provided herein, said reactor comprises a bypass leg directing a portion of said first gas stream to a mixer stage located after a first catalyst stage and before a second catalyst stage. In some embodiments of aspects provided herein, said reactor comprises an internal heat exchanger that is capable of transferring heat from said catalyst to said second gas stream prior to said second gas stream entering said mixer. In some embodiments of aspects provided herein, said airfoil-shaped manifolds uniformly mix said first and second gas streams to provide said third gas stream. In some embodiments of aspects provided herein, said catalyst is included in a catalyst bed. In some embodiments of aspects provided herein, at least a portion of said catalyst bed is in said mixer. In some embodiments of aspects provided herein, said catalyst bed is in a reactor downstream of said mixer.

An aspect of the present disclosure provides a reactor system for performing oxidative coupling of methane to generate hydrocarbon compounds containing at least two carbon atoms ($C_{2+}$ compounds), comprising: (a) a mixer capable of mixing a first gas stream comprising methane with a second gas stream comprising oxygen to provide a third gas stream; (b) a catalyst that performs an oxidative coupling of methane (OCM) reaction using said third gas stream to produce a product stream comprising one or more $C_{2+}$ compounds, wherein said OCM reaction liberates heat; and (c) one or more flow reversal pipes in fluid communication with said mixer and at least partially surrounded by said catalyst, wherein said flow reversal pipes comprise an inner pipe circumscribed by an outer pipe along at least a portion of the length of said inner pipe, wherein said inner pipe is open at both ends and said outer pipe is closed at an end that is surrounded by said catalyst, wherein said flow reversal pipes are configured to transfer heat from said catalyst to said second gas stream during flow along said inner pipe and/or a space between said inner pipe and outer pipe.

In some embodiments of aspects provided herein, said second gas stream (i) flows through said inner pipe into said catalyst along a first direction and (ii) flows in a space between said inner pipe and outer pipe out of said catalyst along a second direction that is substantially opposite to said first direction. In some embodiments of aspects provided herein, said second gas stream (i) flows through a space between said inner pipe and outer pipe and into said catalyst along a first direction and (ii) flows in said inner pipe and out of said catalyst along a second direction that is substantially opposite to said first direction.

An aspect of the present disclosure provides a system for performing oxidative coupling of methane (OCM) reaction to generate hydrocarbon compounds containing at least two carbon atoms ($C_{2+}$ compounds), comprising: (a) an OCM reactor comprising an OCM catalyst that facilitates an OCM reaction to generate said $C_{2+}$ compounds; (b) an injector comprising a fluid flow conduit that directs a first gas stream through at least a portion of said OCM reactor to one or more openings that are in fluid communication with said OCM reactor, wherein said fluid flow conduit is in thermal communication with said OCM reactor, and wherein said first gas stream comprises one of methane and an oxidizing agent; and (c) a gas distribution manifold comprising one or more openings that are in fluid communication with said one or more openings of said injector and said OCM reactor, wherein said gas distribution manifold directs a second gas stream into said OCM reactor, which second gas stream comprises the other of methane and said oxidizing agent.

In some embodiments of aspects provided herein, said oxidizing agent comprises $O_2$. In some embodiments of aspects provided herein, said injector comprises one or more ribs each comprising one or more openings. In some embodiments of aspects provided herein, said one or more ribs are airfoils.

An aspect of the present disclosure provides a method for performing oxidative coupling of methane (OCM) reaction to generate hydrocarbon compounds containing at least two carbon atoms ($C_{2+}$ compounds), comprising: (a) directing a first stream comprising methane and a second stream comprising an oxidizing agent to an OCM reactor comprising an OCM catalyst that facilitates an OCM reaction to generate said $C_{2+}$ compounds, wherein at least a portion of said first stream and/or second stream is in thermal communication with said OCM reactor; (b) performing an OCM reaction using said methane and oxidizing agent to generate said $C_{2+}$ compounds and heat; and (c) directing at least a portion of said heat to said first stream and/or said second stream.

In some embodiments of aspects provided herein, said oxidizing agent comprises $O_2$. In some embodiments of aspects provided herein, said first stream is directed through said OCM reactor. In some embodiments of aspects provided herein, said second stream is directed through said OCM reactor.

An aspect of the present disclosure provides a method for producing at least one $C_{2+}$ alkene, comprising: (a) directing methane and an oxidizing agent into a reactor comprising a catalyst unit and a cracking unit downstream of said catalyst unit, wherein said catalyst unit comprises an oxidative coupling of methane (OCM) catalyst that facilitates an OCM reaction, and wherein said cracking unit generates $C_{2+}$ alkene from $C_{2+}$ alkane; (b) reacting said methane and oxidizing agent with the aid of said OCM catalyst to generate at least one OCM product comprising at least one $C_{2+}$ compound; (c) providing at least one OCM product in a hydrocarbon-containing stream that is directed through said cracking unit, which hydrocarbon-containing stream comprises at least one $C_{2+}$ alkane; and (d) in said cracking unit, cracking said at least one $C_{2+}$ alkane to provide said at least one $C_{2+}$ alkene in a product stream that is directed out of said reactor, wherein said cracking unit is operated at a (i) hydrocarbon-containing stream residence time and (ii) cracking unit temperature profile selected such that the ratio of $C_{2+}$ alkene to $C_{2+}$ alkane in said product stream is greater than 0.1.

In some embodiments of aspects provided herein, said OCM catalyst is a nanowire catalyst. In some embodiments of aspects provided herein, said oxidizing agent is $O_2$. In some embodiments of aspects provided herein, said at least one $C_{2+}$ compound comprises said $C_{2+}$ alkane. In some embodiments of aspects provided herein, in (c), said $C_{2+}$ alkane is provided from a source external to said reactor. In some embodiments of aspects provided herein, said source is a natural gas liquids source. In some embodiments of aspects provided herein, said at least one $C_{2+}$ alkane comprises a plurality of $C_{2+}$ alkanes. In some embodiments of aspects provided herein, said plurality of $C_{2+}$ alkanes are each directed into said cracking unit at different locations. In some embodiments of aspects provided herein, said cracking unit generates $C_{2+}$ alkene from $C_{2+}$ alkane with the aid of heat generated in said OCM reaction. In some embodiments of aspects provided herein, said generating of (d) is adiabatic. In some embodiments of aspects provided herein, said hydrocarbon-containing stream is directed through said cracking unit at a residence time that is less than or equal to 1 second. In some embodiments of aspects provided herein, said residence time is less than or equal to 500 milliseconds. In some embodiments of aspects provided herein, said temperature profile is from about 750° C. to 950° C. In some embodiments of aspects provided herein, said cracking unit has an inlet and an outlet downstream of said inlet, where said hydrocarbon-containing stream is directed from said inlet to said outlet, and wherein said inlet is at a temperature from about 880° C. to 950° C. and said outlet is at a temperature from about 750° C. to 880° C. In some embodiments of aspects provided herein, said ratio is greater than 1. In some embodiments of aspects provided herein, said ratio is greater than 3. In some embodiments of aspects provided herein, said ratio is greater than 5.

An aspect of the present disclosure provides a method for producing at least one $C_{2+}$ alkene, comprising: (a) directing methane and an oxidizing agent into a reactor comprising a catalyst unit and a cracking unit downstream of said catalyst unit, wherein said catalyst unit comprises an oxidative coupling of methane (OCM) catalyst that facilitates an OCM reaction, and wherein said cracking unit generates $C_{2+}$ alkene from $C_{2+}$ alkane; (b) reacting said methane and oxidizing agent with the aid of said OCM catalyst to generate at least one OCM product comprising at least one $C_{2+}$ compound; (c) providing at least one OCM product in a hydrocarbon-containing stream that is directed through said cracking unit from an inlet to an outlet at a residence time that is less than 500 milliseconds at a reactor diameter of at least about 12 inches, wherein said inlet is at a temperature from about 800° C. to 950° C. and said outlet is at a temperature from about 700° C. to 950° C., and wherein said hydrocarbon-containing stream comprises at least one $C_{2+}$ alkane; and (d) in said cracking unit, cracking said at least one $C_{2+}$ alkane to provide said at least one $C_{2+}$ alkene in a product stream that is directed out of said reactor.

In some embodiments of aspects provided herein, said OCM catalyst is a nanowire catalyst. In some embodiments of aspects provided herein, said oxidizing agent is $O_2$. In some embodiments of aspects provided herein, said at least one $C_{2+}$ compound comprises said $C_{2+}$ alkane. In some embodiments of aspects provided herein, in (c), said $C_{2+}$ alkane is provided from a source external to said reactor. In some embodiments of aspects provided herein, said source is a natural gas liquids source. In some embodiments of aspects provided herein, said at least one $C_{2+}$ alkane comprises a plurality of $C_{2+}$ alkanes. In some embodiments of aspects provided herein, said plurality of $C_{2+}$ alkanes are each directed into said cracking unit at different locations. In some embodiments of aspects provided herein, said different locations are located sequentially along said cracking unit's length based on a carbon number of said plurality of $C_{2+}$ alkanes directed thereto. In some embodiments of aspects provided herein, said cracking unit generates $C_{2+}$ alkene from $C_{2+}$ alkane with the aid of heat generated in said OCM reaction. In some embodiments of aspects provided herein, said residence time is less than or equal to 200 milliseconds. In some embodiments of aspects provided herein, said catalyst unit comprises a packed bed catalyst. In some embodiments of aspects provided herein, said diameter is greater than or equal to about 10 feet. In some embodiments of aspects provided herein, said diameter is greater than or equal to about 15 feet.

An aspect of the present disclosure provides an oxidative coupling of methane (OCM) system, comprising: (a) a catalyst unit comprising an OCM catalyst that facilitates the reaction of methane and an oxidizing agent in an OCM reaction to generate an OCM product comprising at least one $C_{2+}$ compound; (b) a cracking unit downstream of said catalyst unit, wherein said cracking unit accepts said OCM product in a hydrocarbon-containing stream that is directed from an inlet to an outlet of said cracking unit, and wherein said cracking unit generates at least one $C_{2+}$ alkene from at least one $C_{2+}$ alkane in said hydrocarbon-containing stream; and (c) one or more inputs to said cracking unit, wherein a given input among said one or more inputs is in fluid communication with said hydrocarbon-containing stream, and wherein said given input provides one or more $C_{2+}$ alkanes to said cracking unit.

In some embodiments of aspects provided herein, said catalyst unit comprises a packed bed. In some embodiments of aspects provided herein, said one or more inputs comprise a plurality of inputs. In some embodiments of aspects provided herein, said plurality of inputs comprises a first input for a first alkane and a second input for a second alkane, wherein said first alkane has fewer carbon atoms than said second alkane, and wherein said first input is closer to said inlet than said second input. In some embodiments of aspects provided herein, said one or more alkanes are selected from the group consisting of ethane, propane, butane, pentane and hexane. In some embodiments of aspects provided herein, said cracking unit is sized to provide a hydrocarbon-containing stream having a residence time that is less than 500 milliseconds. In some embodiments of aspects provided herein, the system further comprises a computer system that is programmed to regulate (i) a residence time of said hydrocarbon-containing stream in said cracking unit and (ii) a temperature profile of said cracking unit to yield a product stream from said cracking unit with a $C_{2+}$ alkene to $C_{2+}$ alkane ratio that is greater than 1.

An aspect of the present disclosure provides a composition produced from an oxidative coupling of methane (OCM) process, the composition comprising ethylene and at least one of: (a) an acetone content that is greater than zero and less than or equal to about 100 parts-per-million (ppm); (b) a carbon dioxide ($CO_2$) content that is greater than zero and less than or equal to about 100 ppm; (c) a carbon monoxide (CO) content that is greater than zero and less than or equal to about 100 ppm; (d) an acetylene content that is greater than zero and less than or equal to about 2000 ppm; (e) a butene content that is greater than zero and less than or equal to about 200 ppm; and (f) relative to an ethylene concentration of said composition, a propylene content equal to or greater than about 0.2%.

In some embodiments of aspects provided herein, said composition has an acetone content that is less than or equal to about 100 ppm, 50 ppm, 10 ppm, 5 ppm, 1 ppm, 100 parts-per-billion (ppb), 50 ppb, 10 ppb, 5 ppb, or 1 ppb. In some embodiments of aspects provided herein, said composition has a carbon dioxide ($CO_2$) content that is less than or equal to about 100 ppm, 50 ppm, 10 ppm, 5 ppm, 1 ppm, 100 ppb, 50 ppb, 10 ppb, 5 ppb, or 1 ppb. In some embodiments of aspects provided herein, said composition has a carbon monoxide (CO) content that is less than or equal to about 100 ppm, 50 ppm, 10 ppm, 5 ppm, 1 ppm, 100 ppb, 50 ppb, 10 ppb, 5 ppb, or 1 ppb. In some embodiments of aspects provided herein, said composition has an acetylene content that is less than or equal to about 2000 ppm, 1000 ppm, 900 ppm, 800 ppm, 700 ppm, 600 ppm, 200 ppm, or 100 ppm. In some embodiments of aspects provided herein, said composition has a butene content that is less than or equal to about 200 ppm, 100 ppm, 50 ppm, or 10 ppm. In some embodiments of aspects provided herein, said composition has a propylene content that is greater than or equal to about 0.3%, 0.4%, 0.6%, 0.8%, 1%, 2%, 3%, 4%, 5%, 6%, 7%, 8%, or 9% relative to an ethylene content of said composition. In some embodiments of aspects provided herein, said composition has at least two of (a)-(f). In some embodiments of aspects provided herein, said composition has at least three of (a)-(f). In some embodiments of aspects provided herein, said composition has at least four of (a)-(f). In some embodiments of aspects provided herein, said composition has at least five of (a)-(f). In some embodiments of aspects provided herein, said composition has all of (a)-(f).

An aspect of the present disclosure provides a method, comprising: (a) providing a reactor comprising (i) an OCM section comprising an OCM catalyst that facilitates the formation of OCM products from methane and an oxidizing agent, and (ii) a post-bed cracking section located downstream of said OCM catalyst section that facilitates cracking of OCM products, wherein said OCM section and said post-bed cracking section are integrated in said reactor; (b) directing said methane and said oxidizing agent to said OCM section; (c) conducting OCM in said OCM section to generate said OCM products; and (d) cracking at least a portion of said OCM products in said post-bed cracking section.

In some embodiments of aspects provided herein, the method further comprises (i) adding external ethane to said post-bed cracking section from a source other than said OCM products, and (ii) conducting cracking on said external ethane in said post-bed cracking section. In some embodiments of aspects provided herein, prior to said adding, said external ethane is preheated to at least about 550° C. in the presence of steam. In some embodiments of aspects provided herein, prior to said adding, said external ethane is preheated to at least about 550° C. in the presence of $CO_2$. In some embodiments of aspects provided herein, the method further comprises: adding external propane to said post-bed cracking section from a source other than said OCM products; and conducting cracking on said external propane in said post-bed cracking section. In some embodiments of aspects provided herein, prior to said adding, said external propane is preheated to at least about 550° C. in the presence of steam. In some embodiments of aspects provided herein, prior to said adding, said external propane is preheated to at least about 550° C. in the presence of $CO_2$. In some embodiments of aspects provided herein, the method further comprises: adding external ethane from a source other than said OCM products to said post-bed cracking section at a first location; adding external propane from a source other than said OCM products to said post-bed cracking section at a second location located downstream relative to said first location; and conducting cracking on said external ethane and said external propane in said post-bed cracking section. In some embodiments of aspects provided herein, prior to said adding, said external ethane or said external propane is preheated to at least about 550° C. in the presence of steam. In some embodiments of aspects provided herein, prior to said adding, said external ethane or said external propane is preheated to at least about 550° C. in the presence of $CO_2$. In some embodiments of aspects provided herein, energy from said OCM products is used in said cracking. In some embodiments of aspects provided herein, said OCM products comprise steam. In some embodiments of aspects provided herein, outlet temperature from said OCM catalyst section is greater than or equal to about 700° C. In some embodiments of aspects provided herein, outlet temperature from said OCM catalyst section is greater than or equal to about 700° C. and less than or equal to about 950° C. In some embodiments of aspects provided herein, residence time in said post-bed cracking section is less than or equal to about 200 milliseconds (ms). In some embodiments of aspects provided herein, residence time in said post-bed cracking section is less than or equal to about 100 ms. In some embodiments of aspects provided herein, residence time in said post-bed cracking section is less than or equal to about 50 ms. In some embodiments of aspects provided herein, said reactor comprises a fixed bed reactor. In some embodiments of aspects provided herein, said reactor comprises a fluidized bed reactor. In some embodiments of aspects provided herein, said reactor comprises a tubular reactor. In some embodiments of aspects provided herein, said tubular reactor comprises a molten salt heat exchange medium. In some embodiments of aspects provided herein, said tubular reactor comprises a first reactor section and a second reactor section downstream of said first reactor section, said first reactor section being operated isothermally and said second reactor section being operated adiabatically. In some embodiments of aspects provided herein, said OCM catalyst section comprises a section of catalytically inert material. In some embodiments of aspects provided herein, said section of catalytically inert material comprises catalytically inert particles that are different in size from OCM catalyst particles in said OCM catalyst section. In some embodiments of aspects provided herein, residence time in said post-bed cracking section is at least about 10 times shorter than residence time in said OCM catalyst section.

An aspect of the present disclosure provides an oxidative coupling of methane (OCM) system, comprising: (a) a feed stream comprising methane; (b) a first OCM reactor supplied by said feed stream, wherein said first OCM reactor comprises an OCM catalyst that reacts a portion of said methane in said feed stream with an oxidizing agent to generate a first OCM product stream; and (c) a second OCM reactor downstream of said first OCM reactor which receives said first OCM product stream from said first OCM reactor, wherein said second OCM reactor is supplied by said feed stream via a bypass of said first OCM reactor and said second OCM reactor comprises an OCM catalyst that generates a second OCM product stream from at least a portion of said methane in said feed stream.

In some embodiments of aspects provided herein, the system further comprises a mixing zone downstream of said first OCM reactor, wherein said mixing zone (i) receives said first OCM product stream from said first OCM reactor and said portion of said methane from said feed stream, and (ii) mixes at least a portion of said first OCM product stream with said portion of said methane from said feed stream.

An aspect of the present disclosure provides a method of chemical looping for an oxidative coupling of methane (OCM) system, comprising: (a) oxidizing a reduced oxygen carrier in a first catalyst bed, thereby producing an oxidized oxygen carrier; (b) transferring said oxidized oxygen carrier to a second catalyst bed; and (c) conducting OCM in said second catalyst bed, wherein said oxidized oxygen carrier provides oxygen for said OCM, thereby producing an OCM product.

In some embodiments of aspects provided herein, said second catalyst bed is substantially free of molecular oxygen. In some embodiments of aspects provided herein, said second catalyst bed is free of molecular oxygen. In some embodiments of aspects provided herein, said second catalyst bed is substantially free of $N_2$. In some embodiments of aspects provided herein, said second catalyst bed is free of $N_2$. In some embodiments of aspects provided herein, said OCM product is substantially free of $N_2$. In some embodiments of aspects provided herein, said OCM product is free of $N_2$. In some embodiments of aspects provided herein, said reduced oxygen carrier or said oxidized oxygen carrier comprises material selected from the group consisting of: $Ni_2O_3$, $Al_2O_3$, $CeO_2$, $MnO_2$, $SiO_2$, perovskite, La-based material, mixed oxide, or combinations thereof.

An aspect of the present disclosure provides a method for the oxidative coupling of methane (OCM) in a reactor to generate hydrocarbon compounds containing at least two carbon atoms ($C_{2+}$ compounds), comprising: (a) mixing a first gas stream comprising methane with a second gas stream comprising oxygen to form a third gas stream comprising methane and oxygen; (b) performing an OCM reaction in a first section of said reactor using said third gas stream to produce a first product stream comprising one or more $C_{2+}$ compounds; and (c) performing an OCM reaction in a second section of said reactor using a fourth gas stream comprising methane in the presence of an oxygen regenerated catalyst to produce a second product stream comprising one or more $C_{2+}$ compounds.

In some embodiments of aspects provided herein, said first section includes an OCM catalyst and said second section includes an oxygen-rich OCM catalyst. In some embodiments of aspects provided herein, said second section does not include an external oxygen source directly coupled to said second section. In some embodiments of aspects provided herein, a source of oxygen for OCM in said second section is from said oxygen regenerated catalyst.

An aspect of the present disclosure provides a reactor system for performing oxidative coupling of methane (OCM) to generate hydrocarbon compounds containing at least two carbon atoms ($C_{2+}$ compounds), comprising a catalyst that performs an OCM reaction to produce a product stream comprising one or more $C_{2+}$ compounds, wherein said catalyst is supported on beta-SiC.

An aspect of the present disclosure provides a reactor system for performing oxidative coupling of methane (OCM) to generate hydrocarbon compounds containing at least two carbon atoms ($C_{2+}$ compounds), comprising a catalyst bed having an OCM catalyst that performs an OCM reaction to produce a product stream comprising one or more $C_{2+}$ compounds, wherein the concentration of said OCM catalyst varies by at least 5% across said catalyst bed.

In some embodiments of aspects provided herein, said concentration of said OCM catalyst varies by at least 10% across said catalyst bed. In some embodiments of aspects provided herein, said concentration of said OCM catalyst varies by at least 20% across said catalyst bed. In some embodiments of aspects provided herein, said concentration of said OCM catalyst varies by at least 50% across said catalyst bed.

An aspect of the present disclosure provides a reactor system for performing oxidative coupling of methane (OCM) to generate hydrocarbon compounds containing at least two carbon atoms ($C_{2+}$ compounds), comprising a tubular reactor including an OCM catalyst bed that contains an OCM catalyst that performs an OCM reaction to produce a product stream comprising one or more $C_{2+}$ compounds, wherein said catalyst bed has a composition gradient that decreases radially from a center to a perimeter of said bed.

An aspect of the present disclosure provides a method for the oxidative coupling of methane (OCM) in a reactor having an OCM catalyst bed to generate hydrocarbon compounds containing at least two carbon atoms ($C_{2+}$ compounds), comprising: (a) mixing a first gas stream comprising methane with a second gas stream comprising oxygen to form a third gas stream comprising methane and oxygen, wherein the linear velocity of said third gas stream through said OCM catalyst bed is less than or equal to about 0.5 meters per second (m/s); and (b) performing an oxidative coupling of methane (OCM) reaction using said third gas stream to produce a product stream comprising one or more $C_{2+}$ compounds.

In some embodiments of aspects provided herein, the linear velocity of said third gas stream through said OCM catalyst bed is less than or equal to about 0.3 meters per second (m/s). In some embodiments of aspects provided herein, the linear velocity of said third gas stream through said OCM catalyst bed is less than or equal to about 0.1 meters per second (m/s).

An aspect of the present disclosure provides a method for the oxidative coupling of methane (OCM) in a reactor to generate hydrocarbon compounds containing at least two carbon atoms ($C_{2+}$ compounds), comprising: (a) mixing a first gas stream comprising methane with a second gas stream comprising oxygen to form a third gas stream comprising methane and oxygen; (b) performing an OCM reaction in said reactor using said third gas stream to produce a product stream comprising one or more $C_{2+}$ compounds; and (c) alternately and sequentially switching an injection location of said third stream into said reactor between a first injection location and a second injection location.

An aspect of the present disclosure provides a reactor system for performing oxidative coupling of methane (OCM) in reactor to generate hydrocarbon compounds containing at least two carbon atoms ($C_{2+}$ compounds), comprising: (a) an OCM catalyst bed containing an OCM catalyst that performs an OCM reaction using methane and oxygen to produce a product stream comprising one or more $C_{2+}$ compounds; (b) an inlet manifold in said OCM catalyst bed that includes a plurality of tubes, wherein said inlet manifold directs a gas stream comprising said methane and oxygen into said OCM catalyst bed; and (c) an outlet manifold in said OCM catalyst bed that includes a plurality of tubes, wherein said outlet manifold directs said product stream from said OCM catalyst bed, wherein said inlet manifold and said outlet manifold are positioned in an interdigitated sandwich configuration.

An aspect of the present disclosure provides a reactor system for performing oxidative coupling of methane (OCM) to generate hydrocarbon compounds containing at least two carbon atoms ($C_{2+}$ compounds), comprising: (a) an OCM reactor having a reactor inlet, a catalyst bed and a reactor outlet, wherein said reactor inlet directs methane and oxygen to said catalyst bed to perform an OCM reaction in the presence of an OCM catalyst to yield a product stream comprising one or more $C_{2+}$ compounds, which product stream is directed out of said catalyst bed via said reactor outlet; and (b) a heat exchanger located in said reactor upstream of said reactor outlet, wherein said heat exchanger is in thermal communication with said product stream.

In some embodiments of aspects provided herein, said heat exchanger is in thermal communication with said catalyst bed and/or said reactor outlet.

An aspect of the present disclosure provides a method for the oxidative coupling of methane to generate hydrocarbon compounds containing at least two carbon atoms ($C_{2+}$ compounds) in a reactor, comprising: (a) mixing a first gas stream comprising methane with a second gas stream comprising oxygen to form a third gas stream comprising methane and oxygen; (b) performing an oxidative coupling of methane (OCM) reaction using said third gas stream and an OCM catalyst bed to produce a product stream comprising one or more $C_{2+}$ compounds; and (c) injecting a fourth stream comprising hydrocarbons into a catalytically inert region of said OCM catalyst bed.

An aspect of the present disclosure provides a method, comprising: (a) providing a reactor comprising (i) an OCM section comprising an OCM catalyst that facilitates the formation of OCM products from methane and an oxidizing agent, and (ii) a post-bed cracking section located downstream of said OCM catalyst section that facilitates cracking of at least a portion of said OCM products, wherein said OCM section and said post-bed cracking section are integrated in said reactor; (b) directing said methane and said oxidizing agent to said OCM section; (c) conducting OCM in said OCM section to generate said OCM products; (d) mixing said OCM products with a $CO_2$ stream to produce a cracking stream; and (e) cracking at least a portion of said OCM products in said cracking stream in said post-bed cracking section.

An aspect of the present disclosure provides a method, comprising: (a) providing a reactor comprising (i) an OCM section comprising an OCM catalyst that facilitates the formation of OCM products from methane and an oxidizing agent, said OCM section comprising an isothermal subsection and an adiabatic subsection, and (ii) a post-bed cracking section located downstream of said OCM catalyst section that facilitates cracking of at least a portion of said OCM products, wherein said OCM section and said post-bed cracking section are integrated in said reactor; (b) directing said methane and said oxidizing agent to said OCM section; (c) conducting OCM in said OCM section to generate said OCM products; and (d) cracking at least a portion of said OCM products in said post-bed cracking section.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGS." herein), of which:

DETAILED DESCRIPTION

Figure 1:
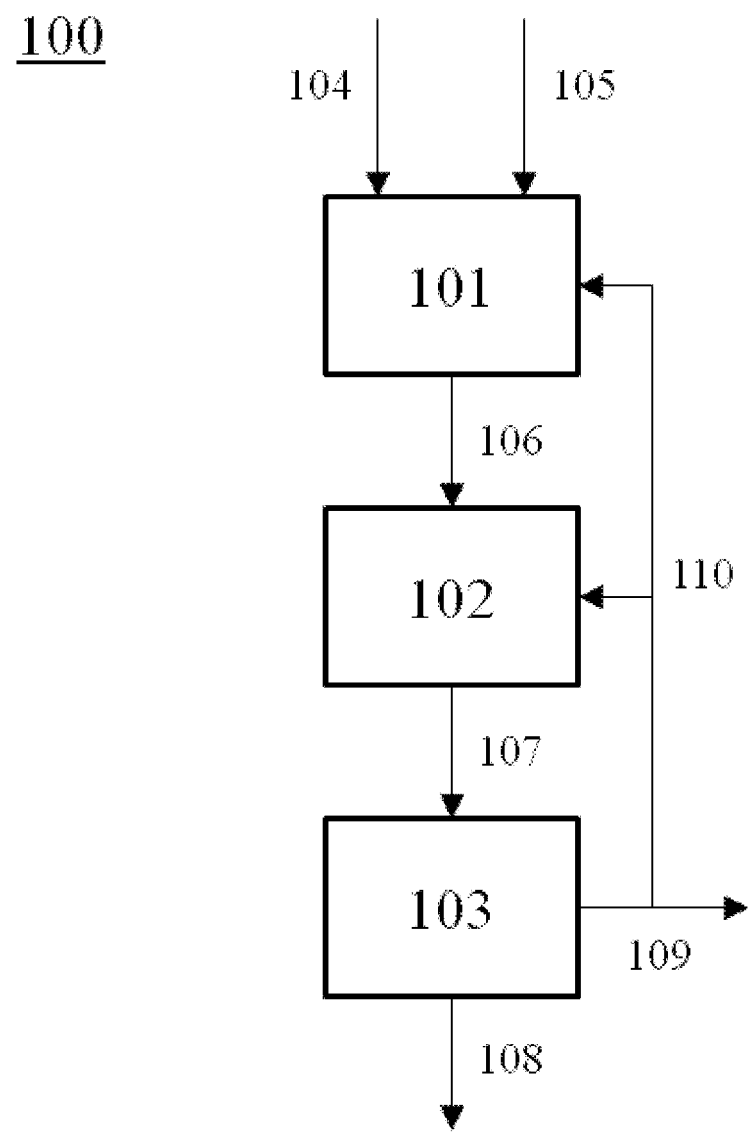
FIG. 1 schematically illustrates a system for the oxidative coupling of methane (OCM)

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "OCM process," as used herein, generally refers to a process that employs or substantially employs an oxidative coupling of methane (OCM) reaction. An OCM reaction can include the oxidation of methane to a hydrocarbon and water, and involves an exothermic reaction. In an OCM reaction, methane can be partially oxidized to one or more $C_{2+}$ compounds, such as ethylene. In an example, an OCM reaction is $2CH_4+O_2 \rightarrow C_2H_4+2H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butane, and the like.

The term "non-OCM process," as used herein, generally refers to a process that does not employ or substantially employ an oxidative coupling of methane reaction. Examples of processes that may be non-OCM processes include non-OCM hydrocarbon processes, such as, for example, non-OCM processes employed in hydrocarbon processing in oil refineries, a natural gas liquids separations processes, steam cracking of ethane, Fischer-Tropsch processes, and the like.

The terms "$C_{2+}$" and "$C_{2+}$ compound," as used herein, generally refer to a compound comprising two or more carbon atoms, e.g., $C_2$, $C_3$ etc. $C_{2+}$ compounds include, without limitation, alkanes, alkene, alkynes, aldehydes, ketones, aromatics esters and carboxylic acids containing two or more carbon atoms. Examples of $C_{2+}$ compounds include ethane, ethene, ethyne, propane, propene and propyne, etc.

The term "non-$C_{2+}$ impurities," as used herein, generally refers to material that does not include $C_{2+}$ compounds. Examples of non-$C_{2+}$ impurities, which may be found in certain OCM reaction product streams, include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "methane conversion," as used herein, generally refers to the percentage or fraction of methane introduced into the reaction that is converted to a product other than methane.

The term "$C_{2+}$ selectivity," as used herein, generally refers to the percentage of all carbon containing products of an oxidative coupling of methane ("OCM") reaction that are the desired or otherwise preferable $C_{2+}$ products, e.g., ethane, ethylene, propane, propylene, etc. Although primarily stated as $C_{2+}$ selectivity, it will be appreciated that selectivity may be stated in terms of any of the desired products, e.g., just $C_2$, or just $C_2$ and $C_3$.

The term "$C_{2+}$ yield," as used herein, generally refers to the amount of carbon that is incorporated into a $C_{2+}$ product as a percentage of the amount of carbon introduced into a reactor in the form of methane. This may generally be calculated as the product of the conversion and the selectivity divided by the number of carbon atoms in the desired product. $C_{2+}$ yield is typically additive of the yield of the different $C_{2+}$ components included in the $C_{2+}$ components identified, e.g., ethane yield+ethylene yield+propane yield+propylene yield etc.).

The term "airfoil" (or "aerofoil" or "airfoil section"), as used herein, generally refers to the cross-sectional shape of a blade. A blade may have one or more airfoils. In an example, a blade has a cross-section that is constant along a span of the blade, and the blade has one airfoil. In another example, a blade has a cross-section that varies along a span of the blade, and the blade has a plurality of airfoils.

The term "auto-ignition" or "autoignition," as used herein in the context of temperature, generally refers to the lowest temperature at which a substance, given sufficient time, will spontaneously ignite without an external source of ignition, such as a flame or spark. Use of the term "auto-ignites" with reference to oxygen refers to the amount of oxygen that reacts with (e.g., combustion reaction) any or all hydrocarbons that are mixed with oxygen (e.g., methane).

The term "substantially equivalent," as used herein in the context of methane concentration, generally means that the methane concentration is within approximately plus or minus 80%, 70%, 60%, 50%, 40%, or 30%, and preferably within plus or minus 20%, 10%, or even 5% of the methane concentration typically passed into an existing fractionation train of a gas facility or cracker facility.

OCM Processes

In some OCM processes, methane reacts with oxygen over a suitable catalyst to generate ethylene, e.g., $2CH_4+O_2 \rightarrow C_2H_4+2H_2O$ (See, e.g., Zhang, Q., Journal of Natural Gas Chem., 12:81, 2003; Olah, G. "Hydrocarbon Chemistry", Ed. 2, John Wiley & Sons (2003)). This reaction is exothermic ($\Delta H=-67$ kcals/mole) and has typically been shown to occur at very high temperatures (>700° C.). Although the detailed reaction mechanism is not fully characterized, experimental evidence suggests that free radical chemistry is involved. (Lunsford, J. Chem. Soc., Chem. Comm., 1991; H. Lunsford, Angew. Chem., Int. Ed. Engl., 34:970, 1995). In the reaction, methane ($CH_4$) is activated on the catalyst surface, forming methyl radicals which then couple in the gas phase to form ethane ($C_2H_6$), followed by dehydrogenation to ethylene ($C_2H_4$). Several catalysts have shown activity for OCM, including various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and combinations thereof, on various supports.

A number of doping elements have also proven to be useful in combination with the above catalysts.

Since the OCM reaction was first reported over thirty years ago, it has been the target of intense scientific and commercial interest, but the fundamental limitations of the conventional approach to C—H bond activation appear to limit the yield of this attractive reaction under practical operating conditions. Specifically, numerous publications from industrial and academic labs have consistently demonstrated characteristic performance of high selectivity at low conversion of methane, or low selectivity at high conversion (J. A. Labinger, *Cat. Lett.*, 1:371, 1988). Limited by this conversion/selectivity threshold, no OCM catalyst has been able to exceed 20-25% combined $C_2$ yield (i.e. ethane and ethylene), and more importantly, all such reported yields operate at extremely high temperatures (>800 C) and/or low pressures (<1 barg). Catalysts and processes have been described for use in performing OCM in the production of ethylene from methane at substantially more practicable temperatures, pressures and catalyst activities. These are described in commonly owned Published U.S. Patent Application Nos. 2012/0041246, 2013/0023079, 2013/165728, and U.S. patent application Ser. Nos. 13/936,783 and 13/936,870 (both filed Jul. 8, 2013), the full disclosures of each of these is incorporated herein by reference in its entirety for all purposes.

A wide set of competitive reactions can occur simultaneously or substantially simultaneously with the OCM reaction, including total combustion of both methane and all partial oxidation products. An OCM process can provide $C_{2+}$ compounds as well as non-$C_{2+}$ impurities. Natural gas can be used to provide methane, in some cases combined with a recycle stream from downstream separation units. Air, enriched air, or pure oxygen can be used to supply the oxygen required for the OCM reaction. Oxygen can be extracted from air, for example, in a cryogenic air separation unit.

To carry out an OCM reaction in conjunction with preferred catalytic systems, the methane and oxygen containing gases generally need to be brought up to appropriate reaction temperatures, e.g., typically in excess of 450° C. for preferred catalytic OCM processes, before being introduced to the catalyst, in order to allow initiation of the OCM reaction. Once that reaction begins or "lights off", then the heat of the reaction is typically sufficient to maintain the reactor temperature at appropriate levels. Additionally, these processes may operate at a pressure above atmospheric pressure, such as in the range of about 1 to 30 bars (absolute).

Providing OCM reactants at the above-described elevated temperatures and pressures presents a number of challenges and process costs. For example, as will be appreciated, heating a mixed gas of methane and oxygen can present numerous challenges. In particular, mixtures of methane and oxygen, at temperatures in excess of about 450° C. and a pressure above atmospheric, can be in the auto-ignition zone, i.e., given sufficient time, the mixture can spontaneously combust without the need of any ignition source. Additionally, the provision of thermal energy to heat the reactants prior to entering a catalytic reactor can have substantial costs in terms of energy input to the process.

At least some component of the auto-ignition risk is alleviated by pre-heating the methane containing gas and oxygen containing gas components to reaction temperature separately. While this avoids autoignition in the heated separate gas streams, in some cases, the OCM process necessarily requires the mixing of these two gas streams prior to carrying out the OCM reaction, at which point, the auto-ignition risk resurfaces. Minimizing the residence time of these mixed, heated gases prior to contact with the catalyst bed within the reactor is desired in order to reduce or eliminate the possibility of auto-ignition of the reactant gases, and the consequent negative implications of combustion. Accordingly, in at least one aspect, the present invention provides improved gas mixing devices systems and methods for complete, rapid and efficient mixing of gas streams so that the mixed streams can be more rapidly introduced to the catalyst bed.

The present disclosure provides processes, devices, methods and systems that address these challenges and costs by allowing for the pre-conditioning of reactant gases prior to their introduction into a catalytic reactor or reactor bed, in a safe and efficient manner. Such pre-conditioning can include (i) mixing of reactant streams, such as a methane-containing stream and a stream of an oxidizing agent (e.g., oxygen) in or prior an OCM reactor or prior to directing the streams to the OCM reactor, (ii) heating or pre-heating the methane-containing stream and/or the stream of the oxidizing agent using, for example, heat from the OCM reactor, or (iii) a combination of mixing and pre-heating.

Mixing Devices, Systems and Methods

In an aspect of the present disclosure, pre-conditioning of OCM reactant streams is achieved by mixing using mixer devices, systems and methods for OCM processes. Such devices or systems can overcome the limitations above by i) mixing the methane-containing and oxygen-containing streams with the required degrees of uniformity in terms of temperature, composition and velocity; and ii) mixing the methane-containing and oxygen-containing streams substantially completely, rapidly and efficiently in order to minimize the residence time of the heated mixed gases before they can be contacted with and reacted in the catalyst bed, which will preferably be less than, and more preferably, substantially less than the amount of time for autoignition of the mixed heated gases to occur.

Required composition uniformity can be such that the deviation of the most oxygen-rich and oxygen-poor post-mixing areas in terms of $CH_4/O_2$ ratio is less than 50%, 40%, 30%, 20%, 15%, 10%, 5%, 4%, 3%, 2%, or 1% compared to a perfectly mixed stream. Required temperature uniformity can be such that the deviation of the hottest and coldest post-mixing zones from the temperature of the ideally mixed stream is less than about 30° C., 20° C., 10° C., or 5° C. Required velocity uniformity can be such that the deviation in flow of the post-mixing areas with the largest and smallest flow from the flow of the ideally mixed stream is less than 50%, 40%, 30%, 20%, 15%, 10%, 5%, 4%, 3%, 2%, or 1%. Any larger deviations of these variables from the average may cause the catalytic bed located downstream of the mixer to perform with a reduced efficiency. Mixers of the present disclosure can aid in achieving a desired degree of compositional, pressure, temperature and/or flow uniformity in a time period lower than the auto-ignition delay time, such as within a time period from about 5 milliseconds (ms) to 200 ms and/or a range of flow rates from about 1 Million standard cubic feet per day (MMSCFD) to 2,000 MMSCFD. In some embodiments, the auto-ignition delay time is from about 10 milliseconds (ms) to 1000 ms, or 20 ms to 500 ms, at a pressure from about 1 bar (absolute) and 100 bars, or 1 bar to 30 bars, and a temperature from about 300° C. to 900° C., or 400° C. and 750° C.

If any portion of the mixed stream is allowed to spend longer than the auto-ignition delay time in the mixing zone before coming in contact with a catalyst in the OCM reactor, this particular portion can auto-ignite and propagate combustion throughout the entire stream. In some cases, 100% of the stream spends less than the auto-ignition time, which may require the mixer to be characterized by a substantially narrow distribution of residence times and the absence of a right tail in the distribution curve beyond the auto-ignition threshold. Such a mixer can provide a non-symmetric distribution of residence times.

An aspect of the present disclosure provides an oxidative coupling of methane process comprising a mixing member or device (or mixer) in fluid communication with an OCM reactor. The mixer is configured to mix a stream comprising methane and a stream comprising oxygen to yield a stream comprising methane and oxygen, which is subsequently directed to the OCM reactor to yield products comprising hydrocarbon compounds. The hydrocarbon compounds can subsequently undergo separation into various streams, some of which can be recycled to the mixer and/or the OCM reactor.

The hydrocarbon compounds can include compounds with two or more carbon atoms (also "$C_{2+}$ compounds" herein). The hydrocarbon compounds can include $C_{2+}$ compounds at a concentration (e.g., mole % or volume %) of at least about 5%, 10%, 20%, 30%, 40%, 50%, 60%, 70%, 80%, 90%, 95%, or 99%. In some situations, the hydrocarbon compounds substantially or exclusively include $C_{2+}$ compounds, such as, for example, $C_{2+}$ compounds at a concentration of least about 60%, 70%, 80%, 90%, 95%, 99%, or 99.9%.

Mixing can be employed in a mixer fluidically coupled to an OCM reactor. The mixer can be integrated with the OCM reactor, or be a standalone unit. In some examples, the mixer is upstream of the OCM reactor. In other examples, the mixer is at least partly or substantially integrated with the OCM reactor. For example, the mixer can be at least partly or substantially immersed in a reactor bed of the OCM reactor. The reactor bed can be a fluidized bed.

Systems and methods of the present disclosure can maximize the efficiency of an OCM reaction and reduce, if not eliminate, undesired reactions.

Fluid properties can be selected such that methane and an oxidizing agent (e.g., $O_2$) do not auto-ignite at a location that is before the catalyst of the OCM reactor. For instance, a stream comprising methane and oxygen can have a composition that is selected such that at most 5%, 4%, 3%, 2%, 1%, 0.1%, or 0.01% of the oxygen in the mixed gas stream auto-ignites. The fluid properties include the period of time in which methane is in contact with oxygen (or another oxidizing agent). The residence time can be minimized so as to preclude auto-ignition. In some cases, the stream comprising methane and oxygen can have a substantially non-symmetric distribution of residence (or delay) times along a direction of flow of said third stream. The residence (or delay) time is the period in which a stream comprising methane and oxygen does not auto-ignite. In some examples, the distribution of residence times is skewed towards shorter residence times, such as from about 5 ms to 50 ms. Auto-ignition delay time may be primarily a function of temperature and pressure and, secondarily, of composition. In some cases, the higher the pressure or the temperature, the shorter the auto-ignition delay time. Similarly, the closer the composition to the stoichiometry required for combustion, the shorter the auto-ignition delay time. Diagrams based on empirical data and thermodynamic correlations may be used to determine i) the auto-ignition region (i.e., the threshold values of temperature, pressure and composition above or below which auto-ignition may occur); and ii) the auto-ignition delay time inside the auto-ignition region. Once the auto-ignition delay time is determined for the desired or otherwise predetermined operating conditions, the mixer may be designed such that 100% of the mixed stream spends less than the auto-ignition time in the mixer itself prior to contacting the OCM catalyst.

During mixing, flow separation may cause a portion of the flow to spend a substantially long period of time in a limited region due to either the gas continuously recirculating in that region or being stagnant. In at least some cases, flow separation causes this portion of the flow to spend more time than the auto-ignition time prior to contact with the catalyst, thus leading to auto-ignition and propagation of the combustion to the adjacent regions, and eventually, to the entire stream.

Mixers of the present disclosure may be operated in a manner that drastically reduces, if not eliminates, flow separation. In some situations, fluid properties (e.g., flow regimes) and/or mixer geometries are selected such that upon mixing a stream comprising methane with a stream comprising oxygen in a mixer flow separation does not occur between the mixer and the first gas stream, the second gas stream, and/or the third gas stream.

FIG. 1 shows an OCM system 100 comprising a mixer 101, an OCM reactor 102 downstream of the mixer 101, and a separation unit 103 downstream of the OCM reactor 102. The arrows indicate the direction of fluid flow. A first fluid stream ("stream") 104 comprising methane ($CH_4$) and a second fluid stream 105 comprising oxygen ($O_2$) are directed into the mixer 101, where they are mixed to form a third mixed gas stream 106 that is directed into the OCM reactor 102. The second fluid stream 105 may comprise $CH_4$ (e.g., natural gas) and $O_2$ mixed and maintained at a temperature below the auto-ignition temperature. In some cases, diluting pure $O_2$ with methane may be desirable to enable relatively simpler material of construction for the mixer compared to situations in which pure $O_2$ is used. In situations where pure $O_2$ is used, materials such as Hastelloy X, Hastelloy G, Nimonic 90, and others can be used as they are high temperature stable and resist metal ignition in oxygen environments. Other materials can be used in the case of oxygen diluted with methane. In the OCM reactor 102, methane and oxygen react in the presence of a catalyst provided within reactor 102, to form $C_{2+}$ compounds, which are included in a fourth stream 107. The fourth stream 107 can include other species, such as non-$C_{2+}$ impurities like Ar, $H_2$, CO, $CO_2$, $H_2O$, $N_2$, $NO_2$ and $CH_4$. The fourth stream 107 is then optionally directed to other unit operations for processing the outlet gas stream 107, such as separation unit 103, used for separation of at least some, all, or substantially all of the $C_{2+}$ compounds from other components in the fourth stream 107 to yield a fifth stream 108 and a sixth stream 109. The fifth stream 108 can include $C_{2+}$ compounds at a concentration (e.g., mole % or volume %) that is at least 10%, 20%, 30%, 40%, 50%, 60%, 70%, 80%, 90%, 95%, or 99%, and the sixth stream 109 can include $C_{2+}$ compounds at a concentration that is less than about 99%, 95%, 90%, 80%, 70%, 60%, 50%, 40%, 30%, 20%, or 10%. The concentration of $C_{2+}$ compounds in the fifth stream 108 can be higher than the concentration of $C_{2+}$ compounds in the sixth stream 109. The sixth stream 109 can include other species, such as Ar, $H_2$, CO, $CO_2$, $H_2O$, $N_2$, $NO_2$ and $CH_4$. At least some, all or substantially all of $CH_4$ and/or $O_2$ in the sixth stream 109 may optionally be recycled to the mixer 101 and/or the OCM reactor 102 in a seventh stream 110. Although illustrated in FIG. 1 as a separate unit operation, the mixer component of the system may be integrated into one or more unit operations of an overall OCM process system. For example, in preferred aspects, mixer 101 is an integrated portion of reactor 102, positioned immediately adjacent to the catalyst bed within the reactor 102, so that the mixed gas stream 106 may be more rapidly introduced to the reactor's catalyst bed, in order to minimize the residence time of mixed stream 106.

Methane in the first fluid stream 104 can be provided from any of a variety of methane sources, including, e.g., a natural gas source (e.g., natural gas reservoir) or other petrochemical source, or in some cases recycled from product streams. Methane in the first fluid stream may be provided from an upstream non-OCM process.

The product stream 108 can be directed to one or more storage units, such as $C_{2+}$ storage. In some cases, the product stream can be directed to a non-OCM process.

Fluid properties (e.g., flow regimes) may be selected such that optimum mixing is achieved. Fluid properties can be selected from one or more of flow rate, temperature, pressure, and concentration. Fluid properties can be selected to achieve a given (i) temperature variation in the third stream 106, (ii) variation of concentration of methane to the concentration of oxygen in the third stream 106, and/or (iii) variation of the flow rate of the third stream 106. Any one, two or all three of (i)-(iii) can be selected. In some cases, the temperature variation of the third stream 106 is less than about 100° C., 50° C., 40° C., 30° C., 20° C., 10° C., 5° C., or 1° C. The variation of the concentration of methane to the concentration of oxygen ($CH_4/O_2$) in the third stream 106 can be less than about 50%, 40%, 30%, 20%, 15%, 10%, 5%, 4%, 3%, 2%, or 1% compared to a perfectly mixed (or ideal) stream. The variation of the flow rate of the third stream 106 can be less than about 50%, 40%, 30%, 20%, 15%, 10%, 5%, 4%, 3%, 2%, or 1%. Such variations can be as compared to a perfectly mixed or thermally equilibrated stream and may be taken along a direction that is orthogonal to the direction of flow. Variations can be measured at the exit plane of 106, for example.

The mixer 101 can mix the first stream 104 and the second stream 105 to generate a stream characterized by uniform or substantially uniform composition, temperature, pressure and velocity profiles across a cross section of a mixing zone of the mixer 101 or reactor 102 (e.g., along a direction that is orthogonal to the direction of flow). Uniformity can be described in terms of deviation of the extremes from an average profile. For example, if the various streams possess different temperatures, the resulting profile of the mixed stream can show a maximum deviation of +/−1 to 20° C. between the hottest and coldest areas compared to the ideal (e.g., perfectly mixed) stream. Similarly, if the various streams possess different compositions, the resulting profile of the mixed stream may show a maximum deviation of +/−0.1 to 20 mole % of all reacting compounds compared to the composition of the ideal stream. Similar metrics can be used for velocity and pressure profiles.

In some cases, the system 100 can include at least 1, 2, 3, 4, 5, 6, 7, 8, 9, or 10 separation units. In the illustrated example, the system 100 includes one separation unit 103. The separation unit 103 can be, for example, a distillation column, scrubber, or absorber. If the system 100 includes multiple separation units 103, the separation units 103 can be in series and/or in parallel.

The system 100 can include any number of mixers and OCM reactors. The system 100 can include at least 1, 2, 3, 4, 5, 6, 7, 8, 9, or 10 mixers 101. The system 100 can include at least 1, 2, 3, 4, 5, 6, 7, 8, 9, or 10 reactors 102. The mixers 101 can be in series and/or in parallel. The reactors 102 can be in series and/or in parallel.

Although described for illustration of preferred aspects as gas streams passing into, through and out of the reactor systems in FIG. 1, it will be appreciated that the streams 104, 105, 106, 107, 108, 109 and 110 can be gaseous streams, liquid streams, or a combination of gaseous and liquid streams. In some examples, the streams 104 and 105 are gaseous streams, and the stream 108 and 109 are liquid streams. In some examples, the streams 104, 105, and 109 are gaseous streams, and the stream 108 is a liquid stream.

In some cases, the system 100 includes multiple OCM reactors 102. The OCM reactors 102 can be the same, similar or dissimilar reactors or reactor types arranged in series or parallel processing trains.

The OCM reactor 102 can include any vessel, device, system or structure capable of converting at least a portion of the third stream 106 into one or more $C_{2+}$ compounds using an OCM process. The OCM reactor 102 can include a fixed bed reactor where the combined methane/oxygen gas mixture is passed through a structured bed, a fluidized bed reactor where the combined methane/oxygen mixture is used to fluidize a solid catalyst bed, and/or a membrane type reactor where the combined methane/oxygen mixture passes through an inorganic catalytic membrane.

The OCM reactor 102 can include a catalyst that facilitates an OCM process. The catalyst may include a compound including at least one of an alkali metal, an alkaline earth metal, a transition metal, and a rare-earth metal. The catalyst may be in the form of a honeycomb, packed bed, or fluidized bed.

Although other OCM catalysts can be disposed in at least a portion of the OCM reactors 102, in some preferred embodiments, at least a portion of the OCM catalyst in at least a portion of the OCM reactor 102 can include one or more OCM catalysts and/or nanostructure-based OCM catalyst compositions, forms and formulations described in, for example, U.S. Patent Publication Nos. 2012/0041246, 2013/0023709, 2013/0158322, 2013/0165728, and pending U.S. application Ser. No. 13/901,309 (filed May 23, 2013) and 61/794,486 (filed Mar. 15, 2013), each of which is entirely incorporated herein by reference. Using one or more nanostructure-based OCM catalysts within the OCM reactor 102, the selectivity of the catalyst in converting methane to desirable $C_{2+}$ compounds can be about 10% or greater; about 20% or greater; about 30% or greater; about 40% or greater; about 50% or greater; about 60% or greater; about 65% or greater; about 70% or greater; about 75% or greater; about 80% or greater; or about 90% or greater.

In the OCM reactor 102, methane and $O_2$ are converted to $C_{2+}$ compounds through an OCM reaction. The OCM reaction (e.g., $2CH_4+O_2 \rightarrow C_2H_4+2H_2O$) is exothermic ($\Delta H=-67$ kcals/mole) and may require substantially high temperatures (e.g., temperature greater than 700° C.). As a consequence, the OCM reactor 102 can be sized, configured, and/or selected based upon the need to dissipate the heat generated by the OCM reaction. In some embodiments, multiple, tubular, fixed bed reactors can be arranged in parallel to facilitate heat removal. At least a portion of the heat generated within the OCM reactor 102 can be recovered, for example the heat can be used to generate high temperature and/or pressure steam. Where co-located with processes requiring a heat input, at least a portion of the heat generated within the OCM reactor 102 may be transferred, for example, using a heat transfer fluid, to the co-located processes. Where no additional use exists for the heat generated within the OCM reactor 102, the heat can be released to the environment, for example, using a cooling tower or similar evaporative cooling device. OCM reactor systems useful in the context of the present invention may include those described in, for example, U.S. patent application Ser. No. 13/900,898 (filed May 23, 2013), which is incorporated herein by reference in its entirety for all purposes.

As described above, in certain aspects, a mixer device or system is provided coupled to or integrated with an OCM reactor or reactor system. Such mixers are described in greater detail below.

In some embodiments, two or more different reactant streams are mixed rapidly and sufficiently for carrying out a reaction involving the two or more streams. In some cases, mixing will be substantially completely within a rapid timeframe within the mixer systems and devices described herein.

In some cases, two or more gaseous streams can be mixed in a mixer within a narrow window of time targeted to be less than the time in which autoignition may occur at the temperatures and pressures of the mixed gas streams. Such narrow window of time can be selected such that the streams are mixed before any OCM reaction has commenced. In some embodiments, the mixing time is no longer than the maximum residence time before auto-ignition occurs. The mixing time can be less than 99%, 95%, 90%, 80%, 70%, 60% or even less than 50% of the maximum residence time. Each and all portions of the mixed stream can spend nearly the requisite amount of time in a mixing zone of a mixer or reactor that is configured to effect mixing. If the reacting mixture spends more time, then undesired reactions, sometimes irreversible, may take place, which may generate undesired products and possibly impede or prevent the formation of the desired products. Such undesired reactions may generate a greater proportion of non-$C_{2+}$ impurities than $C_{2+}$ compounds, which may not be desirable.

In some situations, in order for the optimal residence time to be achieved by each portion of the mixing stream, the distribution of the residence times in the mixing zone can be substantially narrow so as to reduce the possibility for even a small portion of the stream to spend less or more than the allowed time in the mixing area. Such phenomenon can occur if recirculation and/or stagnant areas are formed due to the design of the mixer itself. For example, if the mixing device is a perforated cylinder located in the mainstream of the larger gaseous stream, the cylinder itself can produce significant recirculation zones in the areas immediately downstream, thus generating a wide right tail in the statistical distribution of residence times. Systems and methods of the present disclosure can advantageously avoid such problems.

The present disclosure provides systems and methods for mixing reactant species (e.g., methane and $O_2$) prior to or during reaction to form $C_{2+}$ compounds, such as by an OCM reaction. In some examples, i) two or more gaseous streams are mixed together within a certain time frame and with a given (e.g., minimum) degree of uniformity, and ii) the resulting mixed stream affords a limited overall residence time and a narrow distribution of residence times before operating conditions of the stream are significantly affected by undesired chemical reactions. Prior to or during mixing, reactant species may be preheated.

Figure 2A:
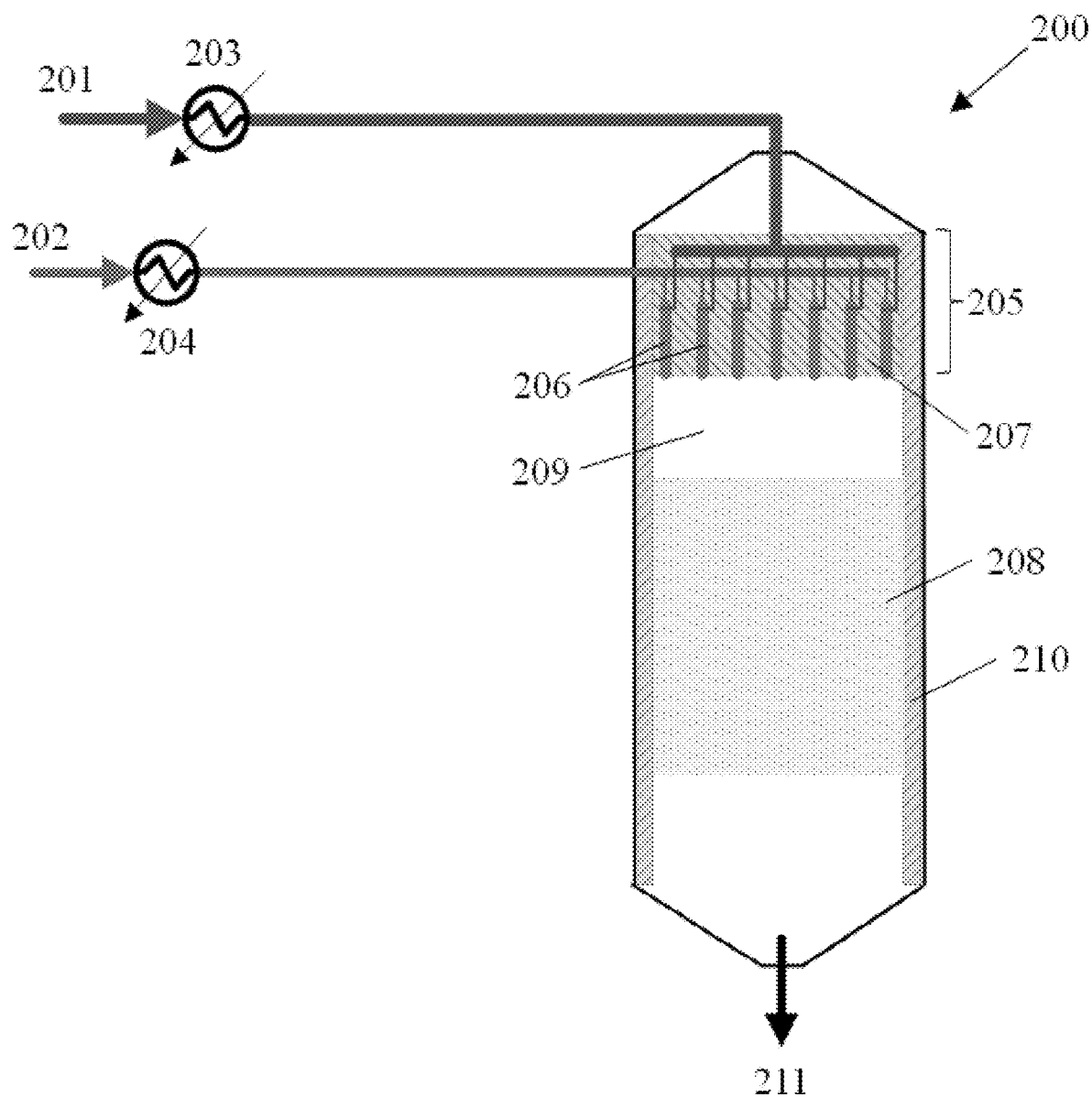
FIG. 2A shows an OCM system comprising methane and oxygen containing gas streams.

A mixer can be integrated with an OCM reactor or separate from the OCM reactor, such as a standalone mixer. FIG. 2A shows an OCM system 200 comprising a methane stream 201 and an air stream (comprising $O_2$) 202 that are each directed through heat exchangers 203 and 204, where each of the streams 201 and 202 is preheated. Next, the streams 201 and 202 are directed to a mixer 205 comprising a plurality of mixing nozzles 206. The nozzles 206 can be in two-dimensional array or in concentric circles, for example. The nozzles can each have the shape of an airfoil, as described elsewhere herein. Void space 207 between the nozzles 206 can be filled with a packing material (e.g., silica) to aid in preventing recirculation of the mixed gas.

The system 200 further comprises a catalyst bed 208 downstream of the mixer 205. The catalyst bed 208 can include an OCM catalyst, as described elsewhere herein. A void space 209 between the mixer 205 and catalyst bed 208 can be unfilled, or filled with an inert medium, such as, for example, aluminum oxide (e.g., alumina) or silicon oxide (e.g., silica) beads. In some cases, the void space can be filled with a material that increases the auto ignition delay time (AIDT), for example by changing the heat capacity of the media and/or interacting with the initial stage of combustion chemistry by scavenging highly reactive species that can act as combustion initiators. Suitable materials can include zirconia beads, ceramic foams, metal foams, or metal or ceramic honeycomb structures. The use of materials that increase the AIDT can be advantageous at elevated pressures (e.g., above about 3, 5, 10, 15, 20, 25, 30, 35, or 40 barg). The system 200 can include a reactor liner 210 that can insulate the system 200 from the external environment. The liner 210 can thermally insulate the mixer 205 and catalyst bed 208 from the external environment.

In each nozzle 206 of the mixer 205, methane and air (including oxygen) can be mixed to form a mixed stream that is directed to the catalyst bed 208. In the catalyst bed 208, methane and oxygen react to form $C_{2+}$ compounds in an OCM process. The $C_{2+}$ compounds along with other compounds, such as unreacted methane and oxygen, are directed out of the system 200 in a product stream 211.

Figure 2B:
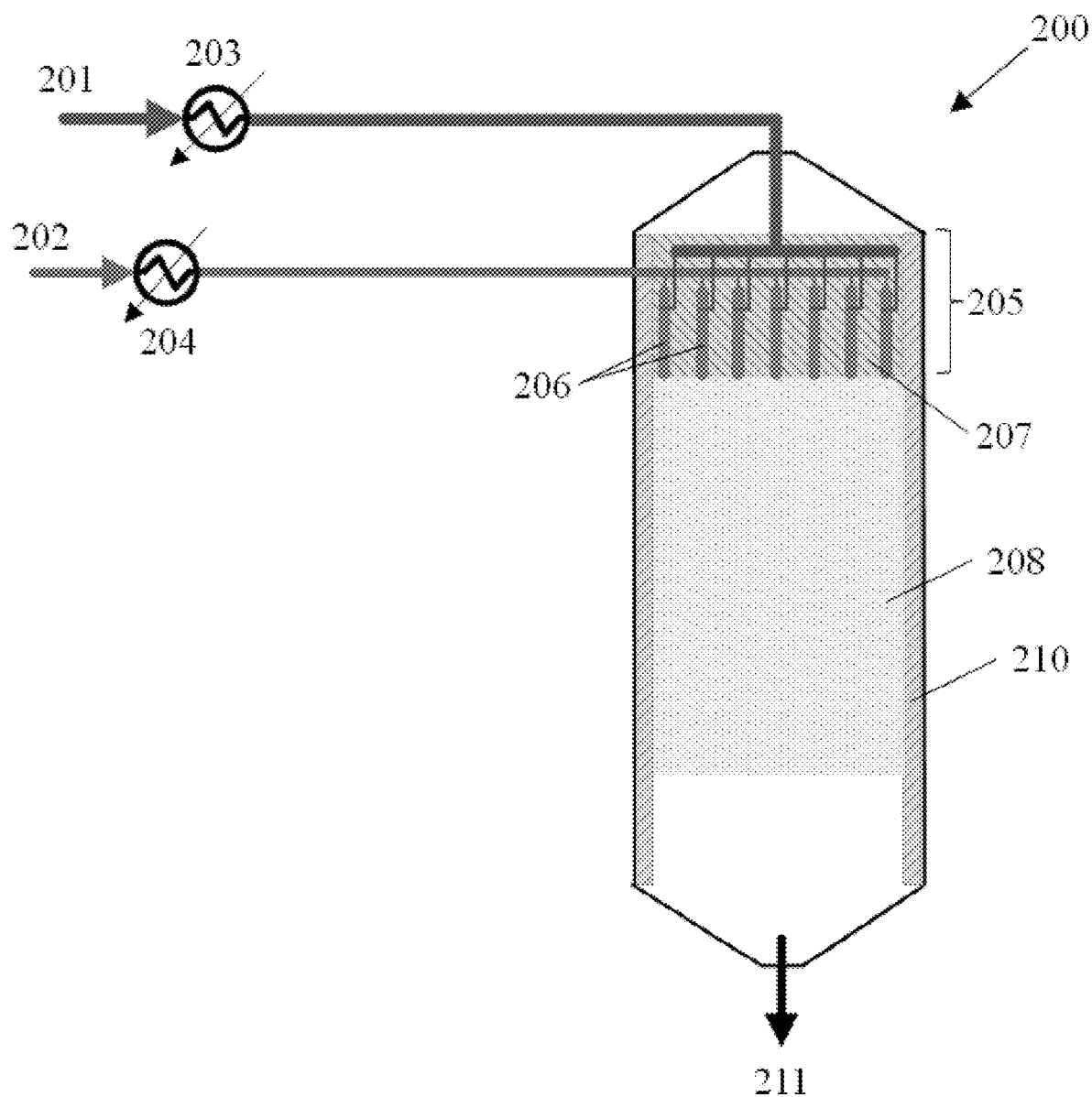
FIG. 2B shows the OCM system of FIG. 2A with a catalyst adjacent to a mixer.

With reference to FIG. 2B, as an alternative, the void space 209 can be precluded and the catalyst bed 208 can be directly adjacent to (and in some cases in contact with) the mixer. The nozzles 206 can each optionally be positioned above, immediately adjacent, or in some cases even extend into the catalyst bed 208. In such a case, an individual nozzle 206 can be surrounded by catalyst material. In some cases, at least 1%, 2%, 3%, 4%, 5%, 6%, 7%, 8%, 9%, 10%, 20%, 30%, 40%, or 50% of the length of an individual nozzle 206 can extend into the catalyst bed 208.

In certain examples, oxygen containing gas, e.g., air, can be introduced into the nozzle 206 at the top of the nozzle 206, and methane can be introduced into the nozzle 206 along the side of the nozzle 206, as shown. As an alternative example, methane can be introduced into a nozzle 206 at the top of the nozzle 206, and oxygen containing gas can be introduced into the nozzle 206 along the side of the nozzle 206. The location of entry along a side of the nozzle 206 can be varied to provide optimal desired mixing, and selected to provide a given mixed gas distribution.

In some situations, the OCM system 200 is operated at a reactor inlet temperature of less than about 800° C., less than about 700° C., less than about 600° C., less than about 500° C., or less than about 400° C. In some embodiments, the OCM system 200 is operated at a reactor inlet temperature of at least about 800° C., at least about 700° C., at least about 600° C., at least about 500° C., or at least about 400° C.

In some embodiments, the OCM system 200 is operated at an inlet pressure less than about 30 bar (gauge), less than about 20 bar, less than about 10 bar, less than about 9 bar, less than about 8 bar, less than about 7 bar, less than about 6 bar, less than about 5 bar, less than about 4 bar, less than about 3 bar, or less than about 2 bar. In some cases, the OCM system 200 is operated at an inlet pressure greater than about 30 bar (gauge), greater than about 20 bar, greater than about 10 bar, greater than about 9 bar, greater than about 8 bar, greater than about 7 bar, greater than about 6 bar, greater than about 5 bar, greater than about 4 bar, greater than about 3 bar, or greater than about 2 bar.

In some situations, the OCM system 200 is operated at and a methane to oxygen ratio that is at least about 1, at least about 2, at least about 3, at least about 4, at least about 5, at least about 6, at least about 7, at least about 8, at least about 9, or at least about 10.

The OCM catalyst can be operated at a peak bed temperature that is less than about 1100° C., less than about 1000° C., less than about 900° C., less than about 800° C., or less than about 700° C. The OCM catalyst can be operated at a peak bed temperature that is greater than about 1100° C., greater than about 1000° C., greater than about 900° C., greater than about 800° C., or greater than about 700° C. The OCM catalyst temperature may be lower at lower methane to oxygen ratios. The temperature change across the catalyst bed (e.g., from inlet to outlet) can scale with the methane to oxygen ratio. In some cases, a lower methane to oxygen ration can effect a larger temperature change across the catalyst bed.

Figure 3A:
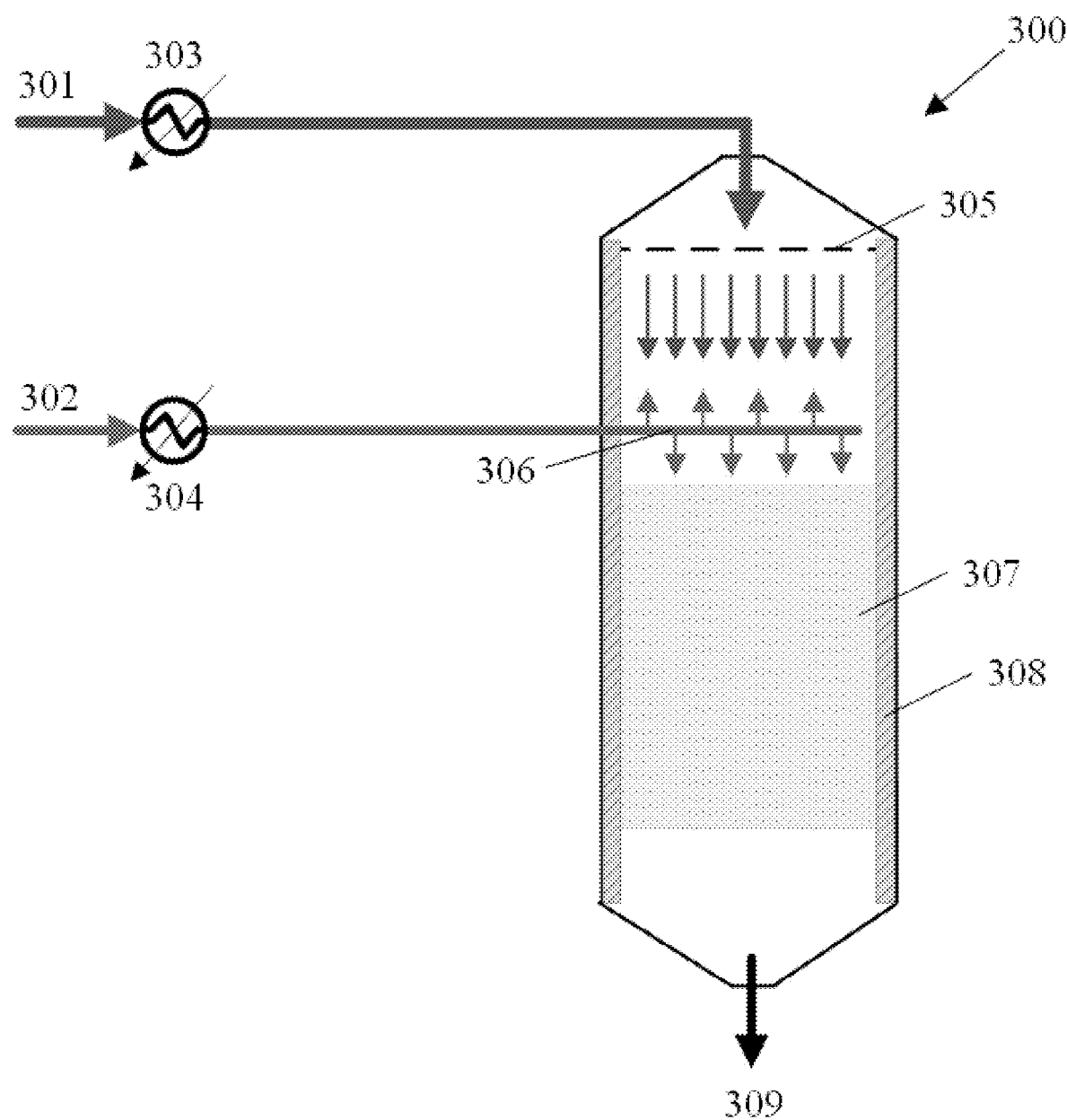
FIG. 3A shows an OCM system comprising a methane and oxygen containing gas stream, a distributor and catalyst bed.

FIG. 3A shows an OCM system 300 comprising a methane stream 301 and an air stream (comprising $O_2$) 302 that are each directed through heat exchangers 303 and 304, respectively, where each of the streams 301 and 302 is preheated. In an example, the methane stream 301 is preheated to a temperature between about 450° C. and 650° C., and the air stream is preheated to a temperature between about 450° C. and about 650° C. Next, the methane stream 301 is directed to a mixer of the OCM system 300. The mixer includes a feed flow distributor 305. The feed flow distributor 305 can be, for example, in the form of a showerhead, which can include a plurality of concentric holes. The feed flow distributor 305 can provide a uniform flow of methane. The air stream 302 is directed into the OCM system 300 to an air distributor 306, which provides streams of air upward towards the feed flow distributor and downward towards a catalyst bed 307. The catalyst bed 307 can include an OCM catalyst, as described elsewhere herein. As used throughout, references to "air", "air streams", and the like should be understood to include enriched air, oxygen, or any other oxidant that can be used to carry out an OCM reaction. Air is but one example of an oxygen source for OCM. When $O_2$ is used as the oxidant, the air stream (i.e., $O_2$) can be pre-heated to between about 150° C. and 350° C., or between about 200° C. and 250° C., inlet temperature.

The air distributor 306 can be a hollow device that includes a chamber in fluid communication with a plurality of fluid flow paths that lead from the chamber to a location external to the air distributor 306. In an example, the air distributor is a hollow tube that includes a plurality of holes along a length of the tube. In another example, the air distributor is a hollow plate (e.g., circular plate) with a plurality of holes. In either example, some of the holes can point towards the feed flow distributor 305 and other holes can point towards the catalyst bed 307.

The system 300 can include a reactor liner 308 that can insulate the system 300 from the external environment. The liner 308 can thermally insulate the distributors 305 and 306, and catalyst bed 307, from the external environment.

In the catalyst bed 307, methane and oxygen react to form $C_{2+}$ compounds in an OCM process. The $C_{2+}$ compounds along with other compounds, such as unreacted methane and oxygen, are directed out of the system 300 in a product stream 309.

Figure 3B:
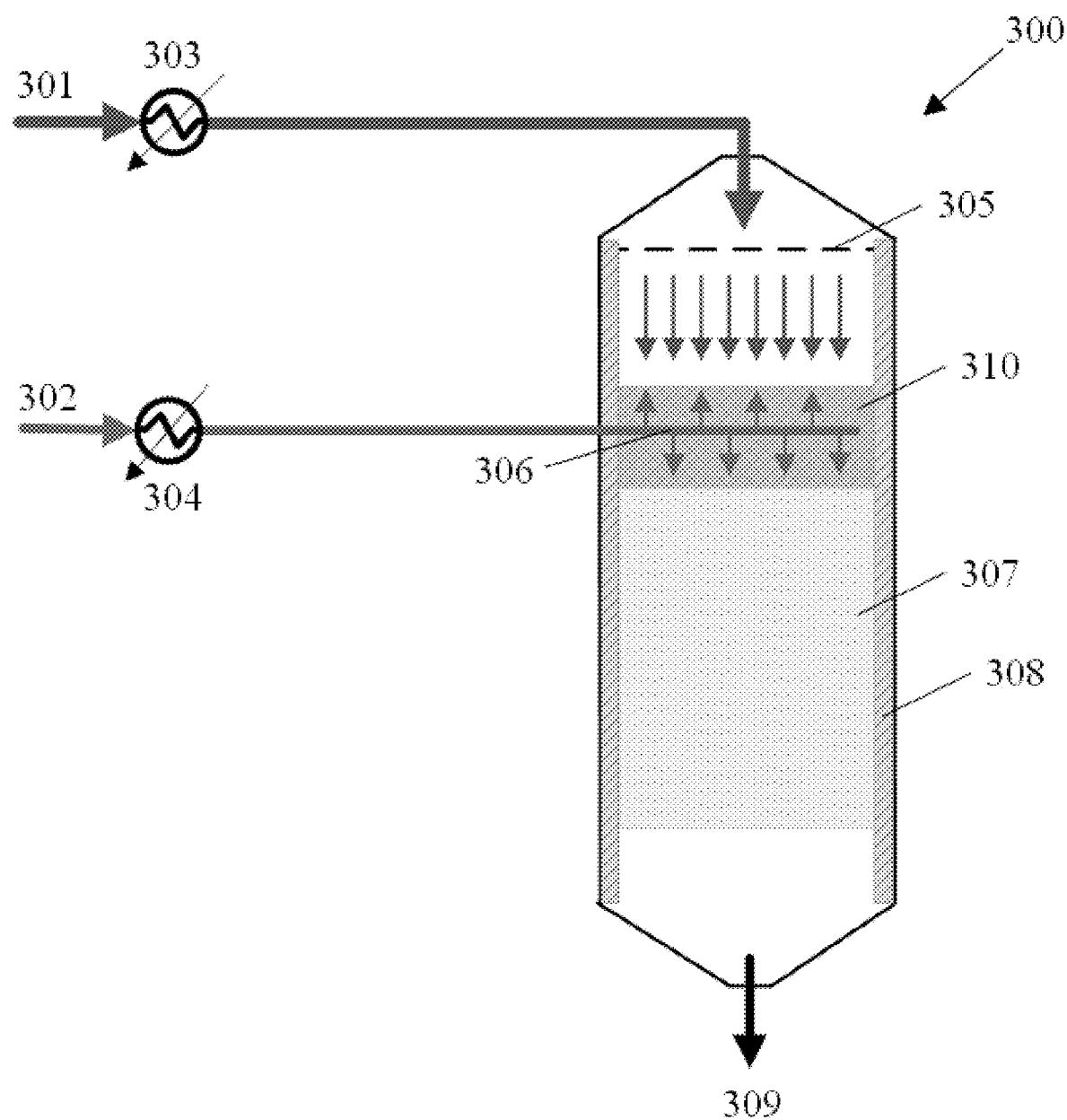
FIG. 3B shows the OCM system of FIG. 3A with the distributor situated in an inert packing medium.
Figure 3C:
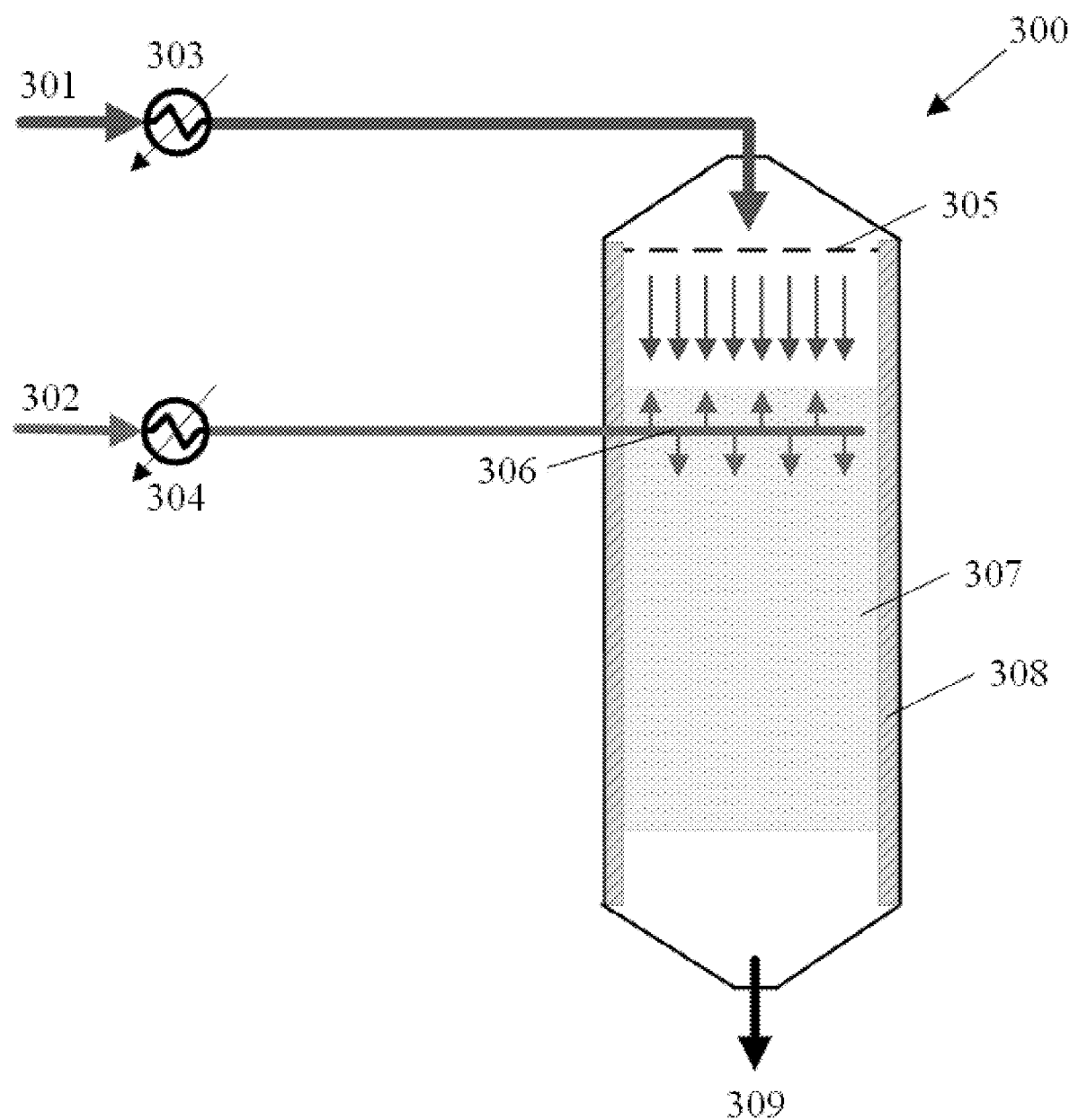
FIG. 3C shows the OCM system in which the distributor is situated in the catalyst bed.

In the example of FIG. 3A, the air distributor 306 is disposed at a location between the feed flow distributor 305 and the catalyst bed 307. As an alternative, the air distributor 306 can be disposed in an inert packing medium or the catalyst bed 307. In FIG. 3B, the air distributor 306 is situated in an inert packing medium 310 that is situated between the feed flow distributor 305 and the catalyst bed 307. The inert packing medium 310 can include, for example, aluminum oxide (e.g., alumina) or silicon oxide (e.g., silica) beads. In FIG. 3C, the air distributor 306 is situated in the catalyst bed 307. In the illustrated example, the air distributor 306 is situated in the catalyst bed 307 at a location that is at or adjacent to the point at which methane enters the catalyst bed. However, other locations may be employed. For example, the air distributor 306 can be situated at a location that is at or at least about 5%, 10%, 20%, 30%, 40%, 50%, 60%, 70%, 80%, or 90% of the length (i.e., from top to bottom in the plane of the figure) of the catalyst bed 307.

Figure 4A:
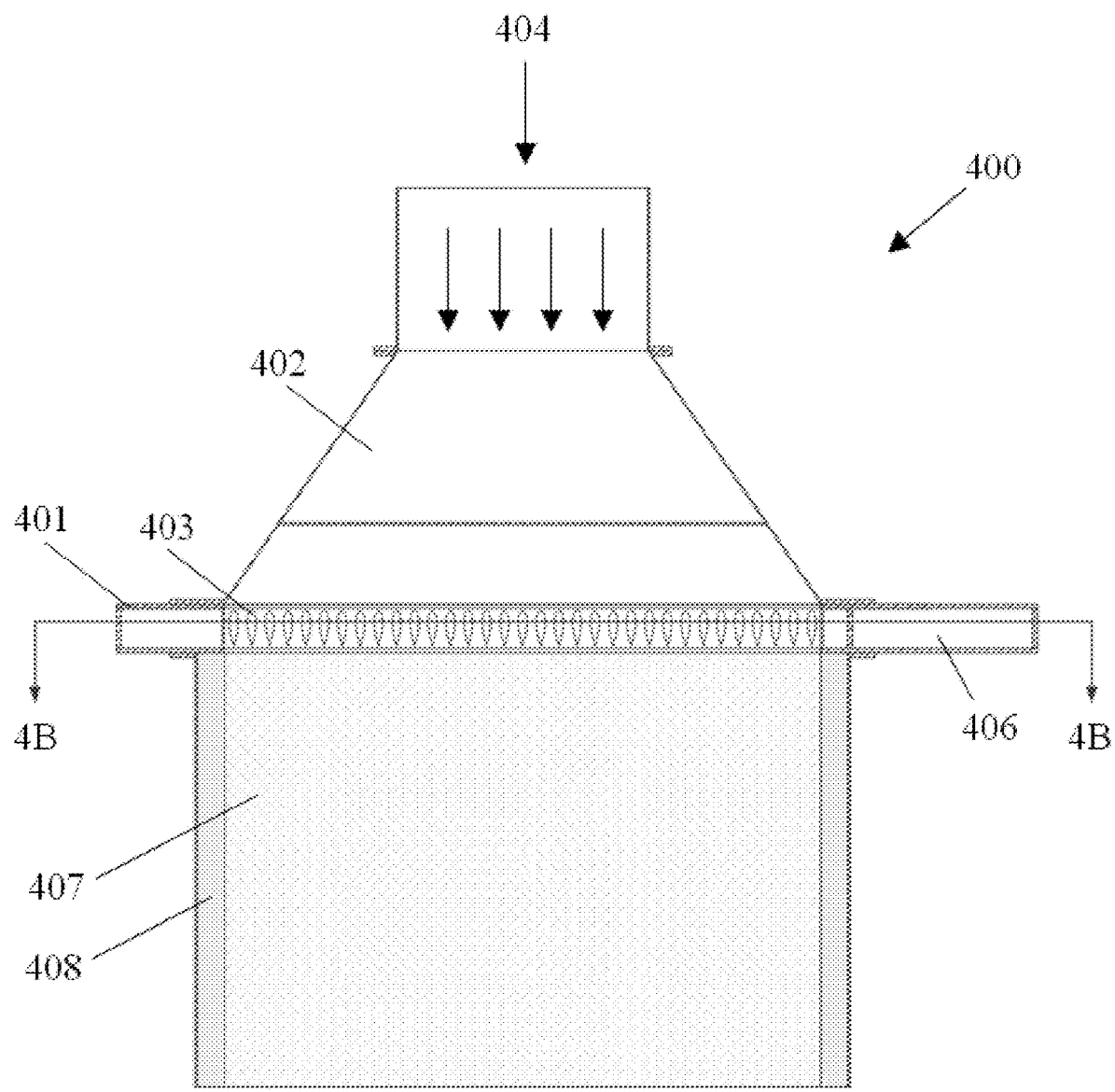
FIGS. 4A and 4B are schematic side and cross-sectional side views, respectively, of an OCM reactor designed with an airfoil-shaped mixer.
Figure 4B:
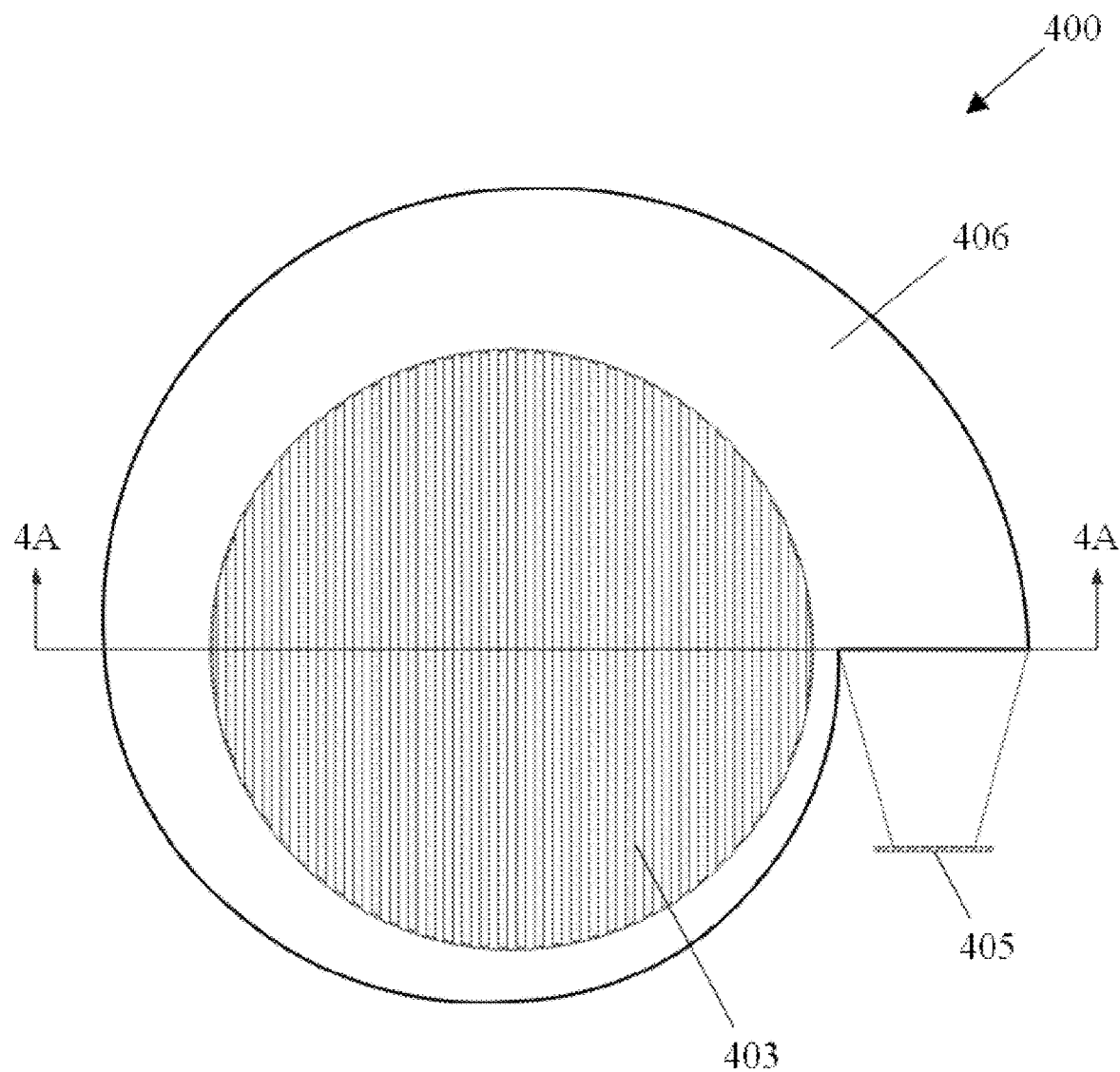

In some embodiments, mixers include one or more airfoils. FIGS. 4A and 4B show an OCM system 400 comprising a mixer (or injector) 401 and a gas distribution manifold 402 adjacent to the mixer 401. FIG. 4B schematically illustrates a cross-section of the system 400, taken along line 4B-4B in FIG. 4A. The mixer 401 comprises a plurality of ribs 403 that are airfoils. An upstream portion of each of the ribs 403 has a larger cross-section than a downstream portion of each of the ribs 403. The ribs 403 can be hollow.

In some embodiments, a mixer is capable of mixing a first gas (e.g., $CH_4$) and a second gas (e.g., $O_2$) within about 1000 ms, 500 ms, 400 ms, 300 ms, 200 ms, 100 ms, 50 ms, or 10 ms. The mixer can include a plurality of manifolds, such as airfoil-shaped manifolds, distributed across a fluid flow path.

In FIGS. 4A and 4B, a first fluid stream is directed into the gas distribution manifold 402 at a first inlet 404. A second fluid stream is directed into the mixer 401 at a second inlet 405 (along the direction of the arrows (i.e., upstream do downstream), at which point the second fluid stream is directed to along a fluid flow path 406 to the ribs 403. The fluid flow path 406 can be a chamber that is in fluid communication with the inlet 405 and the ribs 403. In some examples, the first fluid stream comprises a hydrocarbon (e.g., methane) and the second fluid stream comprises an oxidizing agent. In an example, the second fluid stream is air and the oxidizing agent is $O_2$.

The system 400 further comprises an OCM reactor 407 downstream of the mixer 401. The ribs 403 are situated along a fluid flow path that leads from the inlet 404 to the OCM reactor 407. During use, the first fluid stream enters the system 400 at the inlet 404 and is directed to the gas distribution manifold 402. The second fluid stream enters the system 400 at the inlet 405 and is directed along the fluid flow path 406 to the ribs 403. As the second fluid stream is directed along the fluid flow path, heat from the OCM reactor 407 can heat the second fluid stream. The heated fluid stream enters the ribs 403 and is directed out of the ribs to mix with the first fluid stream that is directed towards the OCM reactor 407 from the gas distribution manifold 402.

The mixer 401 can be close coupled with the OCM reactor 407. In some cases, the OCM reactor 407 includes a catalyst that is included in a space between the ribs 403. The OCM reactor 407 can have various shapes and sizes. The OCM reactor 407 can have a cross-section that is circular, oval, triangular, square, rectangular, pentagonal, hexagonal or any partial shape and/or combination thereof. In an example, the OCM reactor 407 is cylindrical in shape. In some examples, the OCM reactor 407 has a diameter between about 1 foot and 100 feet, or 5 feet and 50 feet, or 10 feet and 20 feet. In an example, the OCM reactor 407 has a diameter that is about 12 feet.

The OCM reactor 407 can include a liner 408 that can be formed of a refractory material. Examples of refractory materials include the oxides of aluminum (e.g., alumina), silicon (e.g., silica), zirconium (e.g., zirconia) and magnesium (e.g., magnesia), calcium (e.g., lime) and combinations thereof. Other examples of refractory materials include binary compounds, such as tungsten carbide, boron nitride, silicon carbide or hafnium carbide, and ternary compounds, such as tantalum hafnium carbide. Refractory material can be coated and/or doped with rare earth elements or oxides, or other basic alkaline earth and/or alkali metals. This may aid in preventing coking. OCM catalyst nanowires may also be used to coat refractory material to prevent coking. The liner 408 can have a thickness from about 0.5 inches and 24 inches, or 1 inch and 12 inches, or 3 inches and 9 inches. In an example, the liner 408 has a thickness of about 6 inches.

The inlets 404 and 405 can have various shapes and sizes. The inlet 405 can have cross-section that is circular, oval, triangular, square, rectangular, pentagonal, hexagonal or any partial shape and/or combination thereof. In some examples, the inlet 404 has a diameter between about 10 inches and 100 inches, or 20 inches and 80 inches, or 40 inches and 60 inches. In an example, the inlet 404 has a diameter that is about 56 inches. In some examples, the inlet 405 has a diameter between about 1 inch and 50 inches, or 10 inches and 30 inches, or 15 inches and 20 inches. In an example, the inlet 405 has a diameter that is about 18 inches.

Each of the ribs 403 can be an airfoil mixer that is configured to bring the second fluid stream in contact with the first fluid stream. This can provide for uniform mixing. Each of the ribs 403 can include one or more openings that are in fluid communication with a fluid flow path leading from the inlet 404 to the OCM reactor 407. In some examples, each of the ribs 403 has an opening on a top or bottom portion of a rib (with respect to the plane of the figure) and/or on opposing side portions—i.e., along a direction that is orthogonal to the direction of fluid flow from the inlet 404 to the OCM reactor 407. By introducing the second fluid stream to the first fluid stream prior to the OCM reactor 407, the ribs can enable mixing of the first and second fluid streams prior to an OCM reaction in the OCM reactor 407.

In some cases, the point along a given rib 403 at which the second fluid stream is introduced to the first fluid stream, as well as the fluid properties of the respective streams (e.g., pressure, flow rate and/or temperature), is selected such that the auto-ignition (e.g., automatic combustion or partial combustion of methane) prior to the OCM reactor 407 is minimized, if not eliminated. This can help ensure that reaction between a hydrocarbon (e.g., methane) and an oxidizing agent (e.g., oxygen) occurs in the OCM reactor 407 to yield $C_{2+}$ compounds, and helps reduce, if not eliminate, unwanted reactions, such as the partial or complete combustion of the hydrocarbon. In some examples, the second stream is introduced to the first stream at the top of each of the ribs 403.

Figure 5:
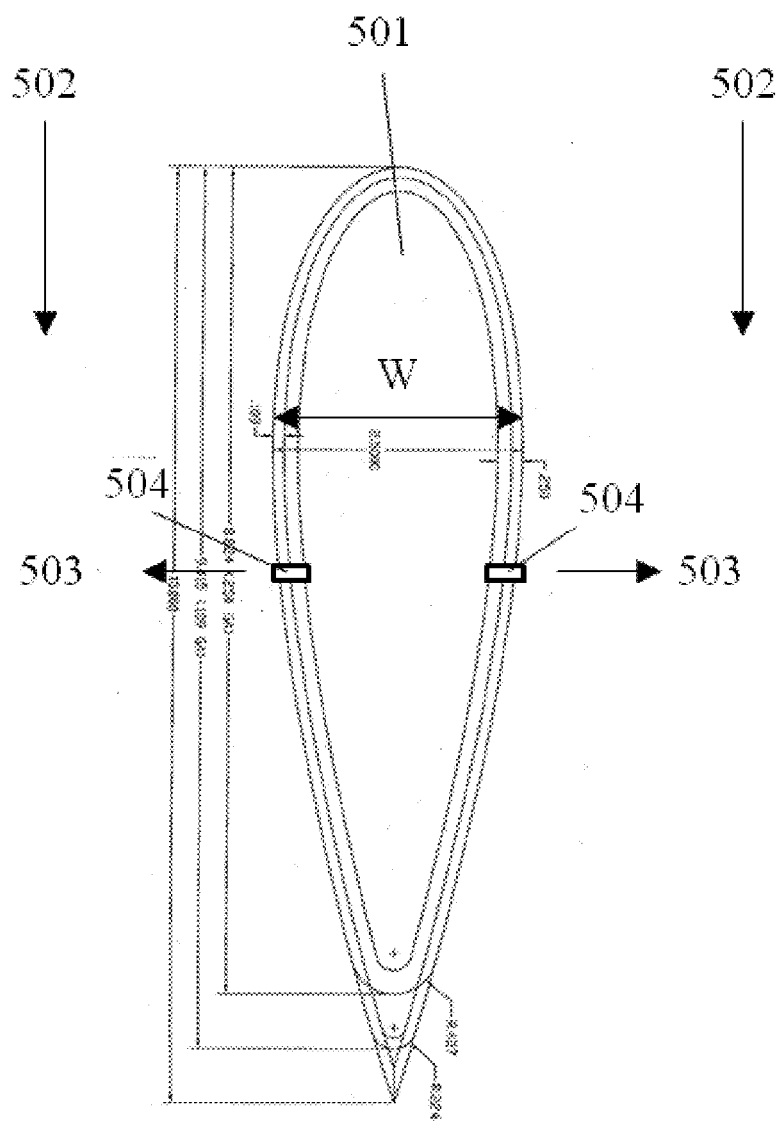
FIG. 5 schematically illustrates a blade that may be employed for use as a rib of a mixer.

A rib can be a blade that is in the shape of an airfoil. FIG. 5 shows a blade 501 that may be employed for use as a rib. In some examples, the blade can have a width (the widest portion, 'W') from about 0.5 inches to 10 inches, and a length from about 0.5 ft. to 10 ft. The blade 501 can be part of a mixer upstream of an OCM reactor. The mixer can be integrated with the OCM reactor. The mixer and OCM reactor can be integrated with a heat exchanger (see below). During operation of an OCM system having the blade 501, a first fluid stream is directed along a fluid flow path 502. The first fluid stream can include a hydrocarbon, such as methane. A second fluid stream 503 is directed out of the blade 501 through openings 504 on opposing sides of the surfaces of the blade 501. The openings 504 can be holes or slits, for example. The second fluid stream 503 can include an oxidizing agent, such as oxygen (O2). In an example, the second fluid stream 503 includes air. The second fluid stream can include a mixture of oxygen and methane.

The openings 504 can be on the sides of the blade 501. As an alternative or in addition to, the openings 504 can be on a top and bottom portion of the blade (with respect to the plane of the figure). The blade 501 can have at least 1, 2, 3, 4, 5, 6, 7, 8, 9, 10, 20, 30, 40, 50, or 100 openings, which can have various sizes and configurations. For example, the openings 504 can be holes or slits. The openings can be disposed side-by-side along the length of the blade 501 (i.e., along an axis orthogonal to the width of the blade ('W') and in the plane of the figure), or side by side along a thickness of the blade 501 (i.e., along an axis orthogonal to the width of the blade and orthogonal to the plane of the figure).

The mixer can provide rapid and complete mixing of two or more gas streams. Additionally, the airfoil shape can help minimize, if not eliminate, stagnant or re-circulation zones in a mixing zone downstream of the mixer. This allows for every portion of the mixed stream to spend the same amount of time within the mixing zone, thus leading to a very narrow and controlled distribution of the residence times in the mixing zone itself.

Figure 6:
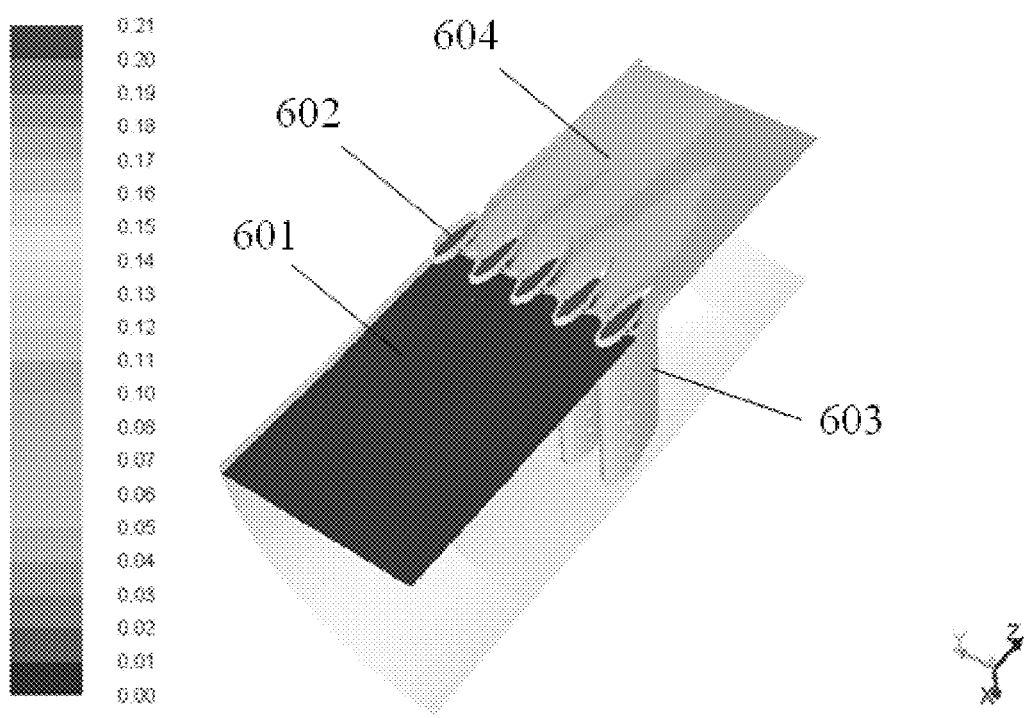
FIG. 6 is a plot from a computational fluid dynamics (CFD) analysis of an airfoil-shaped mixer in fluid communication with an OCM reactor.

FIG. 6 is a plot from a computational fluid dynamics (CFD) analysis of an airfoil-shaped mixer in fluid communication with an OCM reactor. A first gas stream 601 is a methane-containing stream (0% oxygen). A second gas stream 602 is an air stream containing about 21% oxygen ($O_2$). The second gas stream 602 is provided to the first gas stream via airfoil-shaped blades 603. A third gas stream 604 is a mixed stream comprising methane from the first gas stream 601 and oxygen from the second gas stream 602. Use of the airfoil-shaped blades 603 advantageously provides for the absence of stagnant (or re-circulating) zones in the third gas stream 604 downstream of the blades 603. The flow profile in the third gas stream 604 also displays compositional uniformity immediately after the blades 603.

The present disclosure also provides a reactor system for performing oxidative coupling of methane to generate $C_{2+}$ compounds, comprising a mixer capable of mixing a first gas stream comprising methane with a second gas stream comprising oxygen to provide a third gas stream, and a catalyst that performs an OCM reaction using the third gas stream to produce a product stream comprising one or more $C_{2+}$ compounds. During reaction, the OCM reaction liberates heat. The system further comprises one or more flow reversal pipes in fluid communication with the mixer and at least partially surrounded by the catalyst. The flow reversal pipes comprise an inner pipe circumscribed by an outer pipe along at least a portion of the length of the inner pipe. The inner pipe is open at both ends and the outer pipe is closed at an end that is surrounded by the catalyst. The flow reversal pipes are configured to transfer heat from the catalyst to the second gas stream during flow along the inner pipe and/or a space between the inner pipe and outer pipe.

In some situations, the second gas stream (i) flows through the inner pipe into the catalyst along a first direction and (ii) flows in a space between the inner pipe and outer pipe out of the catalyst along a second direction that is substantially opposite to the first direction. As an alternative, the second gas stream (i) flows through a space between the inner pipe and outer pipe and into the catalyst along a first direction and (ii) flows in the inner pipe and out of the catalyst along a second direction that is substantially opposite to the first direction.

The use of airfoil-shaped manifolds can enable cross-mixing of one stream into another stream, which can aid in providing a high degree of uniformity in a substantially compact space. Spacing, size and number of the airfoil-shaped manifolds can be optimized on a case-by-case basis to produce the desired or otherwise predetermined uniformity at the outlet of the mixer while maintaining the height of the manifold within the maximum allowable height, to minimize the time spent by the mixed stream in the mixer zone.

In some cases, a flow distributor (e.g., a porous packed catalyst bed) is used in conjunction with the manifold to achieve no or limited flow recirculation as captured by negative velocities (e.g., against bulk of flow). The mixing device is not limited to the manifolds alone. In some cases, a flow straightener, an air distribution manifold, packing (e.g., touching the air foils underneath the manifold), and/or an expansion cone with a specified angle are used. In some cases, the manifold is closely coupled with a flow control element such as a metal or ceramic foam, a bed of packed particles or other porous media suppressing flow recirculation in a zone downstream of the manifold.

The present disclosure also provides for a reactor system using one or more bypass reactor channels or legs. A bypass channel or leg can bypass a section of a reactor or catalyst bed. Use of a bypass channel can allow a portion of a feed stream to bypass a section of a reactor or catalyst bed, rather than transiting the entire reactor or bed. A bypass channel can be internal to the reactor or catalyst bed. For example, a bypass channel can comprise a region of catalytically inert material within a catalyst bed. A bypass channel can be external to the reactor or catalyst bed. For example, a bypass can comprise a pipe or other conduit which directs a portion of feed stream into a catalyst bed at a point downstream of a section of the catalyst bed. Use of a bypass channel or leg can decrease the feed linear flow rate at the front end of the catalyst bed compared to the feed linear flow rate at the back of the catalyst bed. Light off temperature and inlet temperature under operating conditions can both be dependent on the linear flow rate through the catalyst. Using a bypass leg can result in a lower light off temperature. Using a bypass leg can result in a lower inlet temperature. Using a bypass leg can result in a lower extinction temperature. Lower inlet temperature can result in lower risk of premature, non-catalyzed feed reaction. Lower inlet temperature can result in greater conversion across a catalyst bed. Using a bypass leg can result in higher selectivity. Using a bypass leg can preserve a greater amount of higher hydrocarbons from a feed stream in a product stream. A reactor system can comprise 1, 2, 3, 4, 5, 6, 7, 8, 9, 10, or more bypass legs or channels. The reactor or catalyst bed can comprise a mixing section for mixing product from a first section of catalyst bed with feed material from a bypass. The mixing section can mix material from the initial section of the reactor or catalyst bed with feed material from the bypass channel. The effect of a bypass channel can be created by using multiple reactors with refractory lining between them to preserve the temperature rise from partial conversion of the feed in the first section.

A partial bypass leg can be employed for the use of wet natural gas. A reactor can comprise a first section of a reactor catalyst bed (e.g., OCM bed) and a second section of a reactor or catalyst bed (e.g., OCM bed). The reactor or catalyst bed can comprise a mixing section for mixing product from a first section of catalyst bed with feed material from a bypass. Prior to entering a reactor feed, a methane source stream (e.g., natural gas stream) can be dried in a dryer (e.g., pressure swing adsorption (PSA) dryer). The dryer can produce a dry methane source stream (e.g., natural gas stream) and a wet methane source stream (e.g., natural gas stream). Wet methane source can be fed into a reactor or catalyst bed via a bypass, bypassing a first section of the reactor bed. A wet methane source stream can comprise higher hydrocarbons. For example, at about a 15% to 30% methane rejection rate from a dryer, a wet methane source stream can comprise about five times higher concentration of higher hydrocarbons than the inlet methane source stream. Higher hydrocarbons in a wet methane source stream can bypass a portion of the reactor bed, being injected into a section of reactor where $O_2$ is reduced significantly and intermediate temperature is high, improving the reaction of such higher hydrocarbons. Such a process can be combined with a selective olefin removal sorption unit to close the loop and allow recycling of hydrocarbons. Such a process can be combined with in bed cracking with supplemental $O_2$.

As described in the present disclosure, a reactor with OCM feed flow splitting and a method for reaction of a fraction of the oxygen in an OCM reactor sub-section can be beneficial. For example, the reactors and methods described herein can aid in creating greater control of oxygen usage and temperature rise through the reactor. In particular, combining an OCM product stream with cooler unreacted feed can have several benefits.

A first benefit can be increasing the operating range of the reactor system for lower gas inlet temperatures. This can be achieved by using longer residence times and lower gas linear velocities in the OCM reactor subsection and processing a fraction of the oxygen before remixing its effluent to the remainder of the OCM reactor system feed. The reactor extinction temperature in the highly exothermic OCM reaction can be strongly depressed by increasing the reactor residence time and lowering gas linear velocities.

A reduced inlet gas temperature in adiabatic OCM reactor systems can be beneficial for increasing per pass conversion and reducing the likelihood of premature auto-ignition of the feed mixture. Prevention of auto-ignition can be more challenging with increased pressure of operation.

Another benefit of the reactors and methods described herein can be reducing exposure of higher hydrocarbons included in the OCM feed gas to intermediate reaction temperatures (e.g., in the range of 450° C. to 650° C.). At these intermediate operating temperatures, higher alkanes or alkenes can be (preferentially) combusted to $CO_2$ and water. However, at higher temperatures most of these desirable molecules are left intact.

Reducing combustion of desirable molecules in the feed can be important for multistage OCM reactor trains, as propylene and ethylene in the effluent of the upstream reactor(s) have to go through downstream reactors after being mixed with additional oxygen. Reducing combustion can also be desirable when processing wet natural gas feeds (e.g., natural gas having $C_{2+}$ compounds). Avoiding combustion at the inlet of the OCM catalyst bed can enable the use of the higher hydrocarbons in the feed for cracking downstream of the OCM bed.

If the bypass region of the reactor and the split reaction section of the reactor are in good thermal contact, there can be an additional benefit of controlling the catalyst temperature and improved catalyst life.

A reactor system can be designed to employ chemical looping. Chemical looping can comprise the transfer of material, such as catalyst bed material, from one catalyst bed to another. For example, a reactor system can comprise two reactor beds, wherein a bed material is oxidized in a first bed, then transferred to a second bed and used as an oxygen source for a reaction or other process, thereby becoming reduced and ready for oxidation in the first bed again. In this way, catalyst bed material can serve as an oxygen carrier. The steps of oxidation of bed material, transfer of bed material from a first bed to a second bed, reaction with reduction of bed material, and transfer of bed material from the second bed back to the first bed can be repeated as often or as frequently as needed. This design can be extended to systems comprising more than two beds, such as systems with 3, 4, 5, 6, 7, 8, 9, 10, or more beds. In some cases, oxygen provided by oxidized bed material can be the predominant source of oxygen for a reaction. In some cases, oxygen provided by oxidized bed material can be the sole source of oxygen for a reaction. Providing oxygen via an oxygen carrier rather than from molecular oxygen can result in reduced amounts of molecular oxygen present during a reaction, such as an OCM reaction. Reduced amounts of molecular oxygen can result in lower $CO_2$ yield from the reaction, as well as increased selectivity to $C_{2+}$ products. A reactor bed can comprise a fluidized bed. Oxygen carrier materials can comprise but are not limited to $Ni_2O_3$, $Al_2O_3$, $CeO_2$, $MnO_2$, $SiO_2$, perovskites, lanthanides, actinides, mixed oxides, and combinations thereof.

The present disclosure also provides for an integrated OCM fluid bed with partial reactive air separation. OCM can be used to consume oxygen (e.g., $O_2$) from air in one section of a reactor (e.g., a fluidized bed reactor), and O* regenerated catalyst can be reacted with natural gas or another methane source to produce olefins in a second section of a reactor. The reactor sections can be adjacent to each other. The reactor sections can be physically separated and have a means to move catalyst particles between sections. The bed material can have a fraction which moves counter to the gas flow. This movement can allow for carrying adsorbed species or chemical potential between reactor sections without mixing the reducing and oxidizing streams. Steam can be injected to reduce the $N_2$ content of a resulting OCM product stream. The pressure of outlet flows can be controlled to achieve a specific $N_2$ separation. Minimized gas linear velocity can be maintained in each reactor section to enable circulation of solid material. Different reactor sections can have different geometric parameters, such as tube diameter, which can be used to achieve a particular linear velocity profile.

A reactor system can comprise beta-SiC catalyst support. Beta-SiC can be used as a support for OCM catalyst formulations. Use of beta-SiC as a catalyst support can allow well-controlled heat transfer from catalyst active sites to lower hot spots on catalytic active sites. Use of beta-SiC as a catalyst support can improve catalyst life. Use of beta-SiC as a catalyst support can reduce or prevent loss of catalyst components into the gas phase. Use of beta-SiC as a catalyst support can allow use of smaller amounts of catalyst; for example, 25%-33% of OCM catalyst on beta-SiC can be sufficient for an OCM reaction. Beta-SiC catalyst supports can be stable to boiling in strong acids and bases, allowing recovery of catalyst components from the catalyst support. Active catalyst materials that may be deposited on beta-SiC catalyst supports may be as described herein, including materials described in, for example, U.S. Patent Application Nos. 2012/0041246, 2013/0023079, 2013/165728, and U.S. patent application Ser. Nos. 13/936,783 and 13/936,870 (both filed Jul. 8, 2013), each of which is entirely incorporated herein by reference.

A reactor system can employ a graded catalyst concentration throughout a catalyst bed. For example, the top of a catalyst bed can comprise a pure OCM catalyst composition while a portion of the outlet sections of the bed can comprise an impregnated SiC-based catalyst, a catalyst support with a lower concentration of OCM catalyst, or a SiC catalyst support without any supported catalyst. A graded catalyst concentration can result in less catalyst usage in a reactor bed. A graded catalyst concentration can enhance catalyst selectivity. A graded catalyst concentration can improve catalyst life. The catalyst concentration can vary (e.g., along the direction of fluid flow through the bed) by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 100%, 150%, 200%, 250%, 300%, 350%, 400%, 450%, 500%, 550%, 600%, 650%, 700%, 750%, 800%, 850%, 900%, 950%, or 1000% across the catalyst bed.

The present disclosure provides for a reactor system employing a tubular bed design. Large radial temperature gradients can be generated and maintained in a tubular reactor as cooling is limited by heat transport inside the tube. The temperature profile inside the tube can be driven by the non-linear increase in catalyst activity with temperature and the effect of local $O_2$ concentration. Use of a single catalyst charge can result in a single hot zone radially centered in or near the middle of the tube, with an increase in temperature followed by a drop in $O_2$ levels resulting in a drop in temperature.

A tubular bed reactor can comprise multiple zones. Active catalyst can be distributed in layers or zones separated by inert material (e.g., inert packing). Inert material can provide gas mixing. The reaction mixture can cool down between active zones, allowing use of a larger catalyst bed volume compared to a homogenous packing of active catalyst. Mixing can occur between zones, for example by a ceramic or ceramic-lined metal Sulzer mixer or by a tab mixer.

A tubular bed reactor can comprise semi-multistage adiabatic design. Large longitudinal temperature gradients can be generated through a reactor bed, with peak temperature capped by the adiabatic reaction temperature. Active catalyst can be distributed in layers or zones separated by inert material (e.g., inert packing). Inert material can provide gas mixing. The inlet temperature of each stage can be controlled to a low enough temperature to enable addition of supplemental air to continue the reaction. Air can be introduced in inert packing sections between catalytically active zones.

Inert packing sections can incorporate a solid core to improve heat transfer to the wall. Use of a solid core can promote a flatter temperature profile at the inlet of active catalyst zones. Tubular reactors can comprise a radial catalyst composition gradient. For example, the reactor tube can be packed with mostly inert material near the tube wall and with a charge of mostly active material in the tube center. A non-porous insulation liner can be used in place of an outer layer of inert packing. Radial tube composition gradients can promote bypass of material and extend the length of tube used to perform the reaction. Radial tube composition gradients can reduce the proportion of reaction occurring at intermediate temperatures. Radial packing can be achieved using a cylindrical guide to separate bed zones during packing. Different guide shapes can be used in different sections of the reactor tube. Different zone shapes can provide different flow resistances. Different flow resistances can equalize flow resistance through the reactor tube in the presence of a large radial temperature gradient. Flow can be fed down the center of the reactor tube and out through the perimeter space, or vice versa.

Figure 29A:
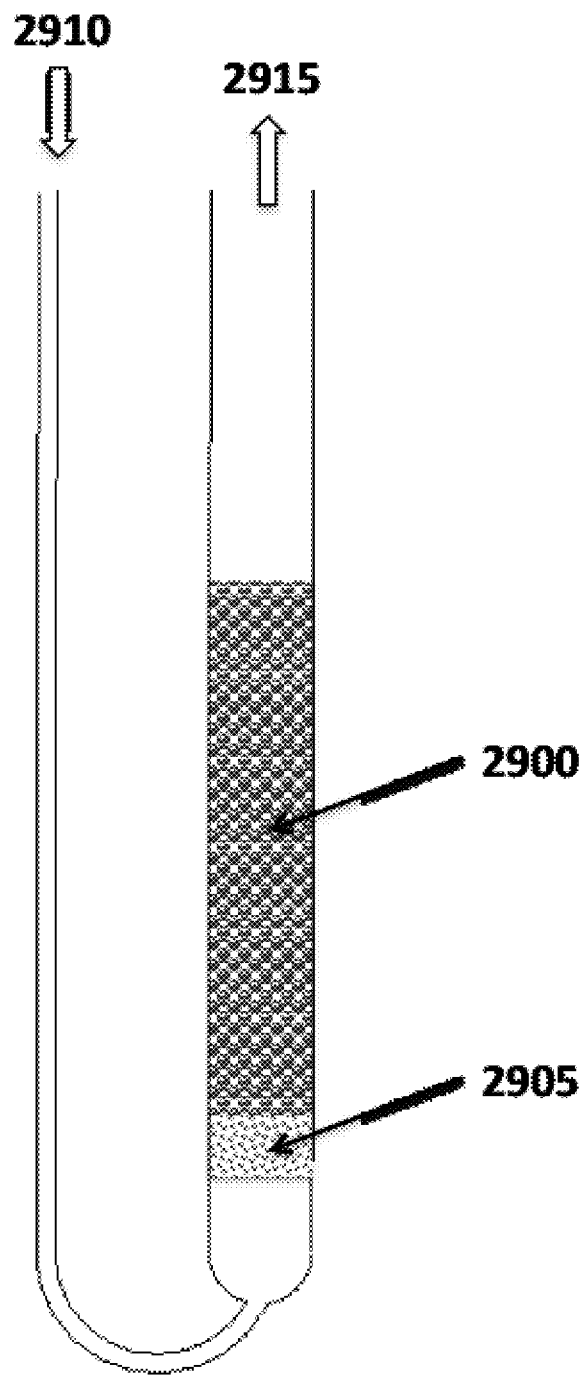
FIG. 29A-D show examples of catalyst packing geometries.

The catalyst can be organized or arranged in the reactor (i.e., packed) in various geometries that can lead to various advantages. FIG. 29A shows a standard bed packing geometry where a catalyst bed 2900 is packed over a layer of inert material 2905. Reactants flow into the reactor 2910 and are converted to products, which flow out of the reactor 2915. Alternate bed packing strategies are shown in FIG. 29B-29D.

Figure 29B:
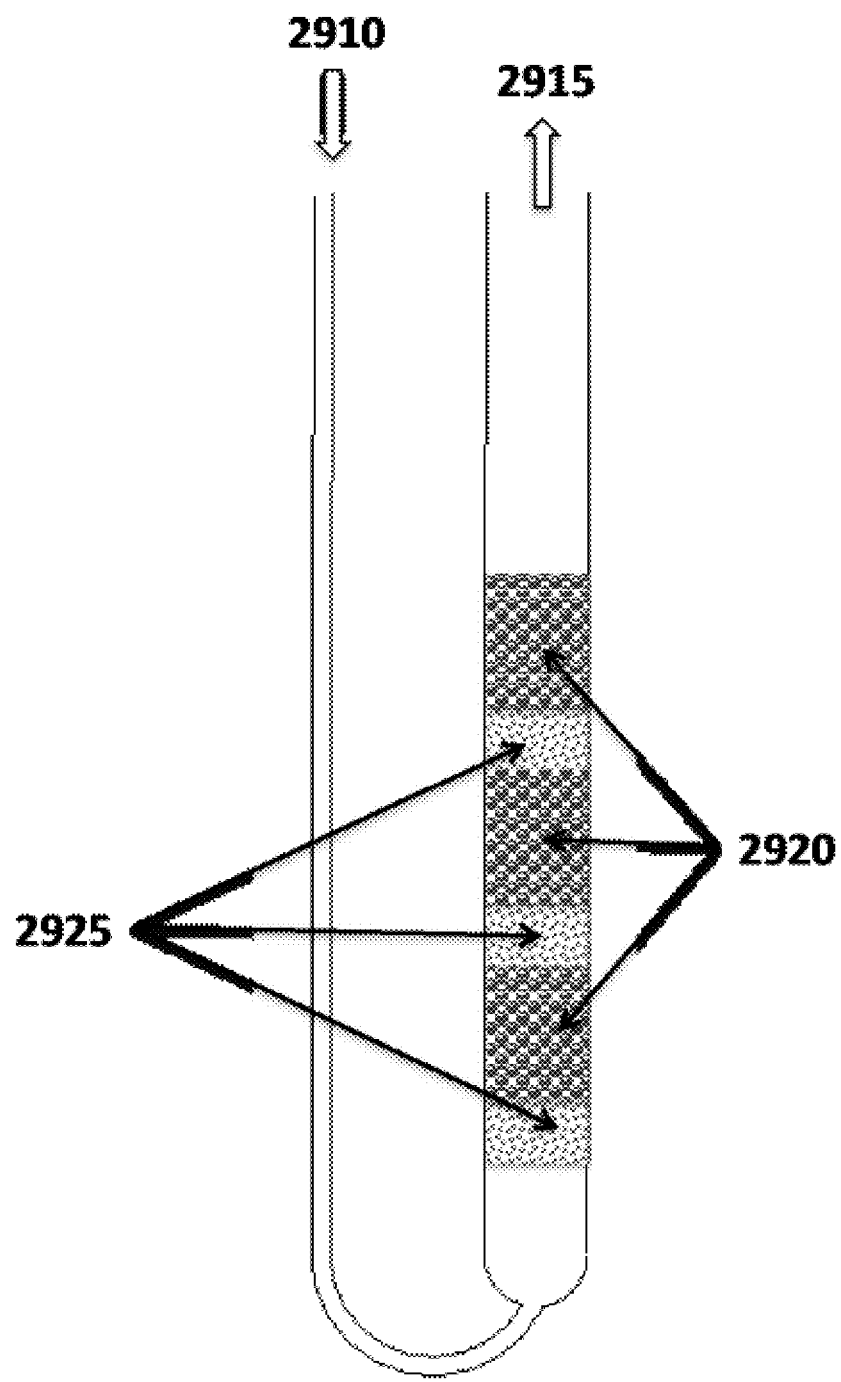

The bed packing in FIG. 29B uses a combination of catalytically active and catalytically inert packed materials to modulate the reactor temperature profile. Here, regions of catalyst 2920 are interspersed and alternated with regions of inert material 2925 in the packed bed. This configuration can be useful for moderating the temperature of the active catalyst bed by increasing the volume into which the reaction is carried out and heat produced. With this increase of volume, the surface area of the tube in contact with the (heat generating) reaction volume increases, enabling improved control of heat removal from the system. Using a band of catalytically inert packing as shown in FIG. 29B can be better than simply diluting the all catalyst bed with inert material (i.e., mixing the catalyst and the inert material) because a large radial gradient within the tube can be desirable to increase the average bed operating temperature. Addition of axial bands has minimal impact on the radial temperature gradient, while allowing to spread the heat released by the reaction axially.

Figure 29C:
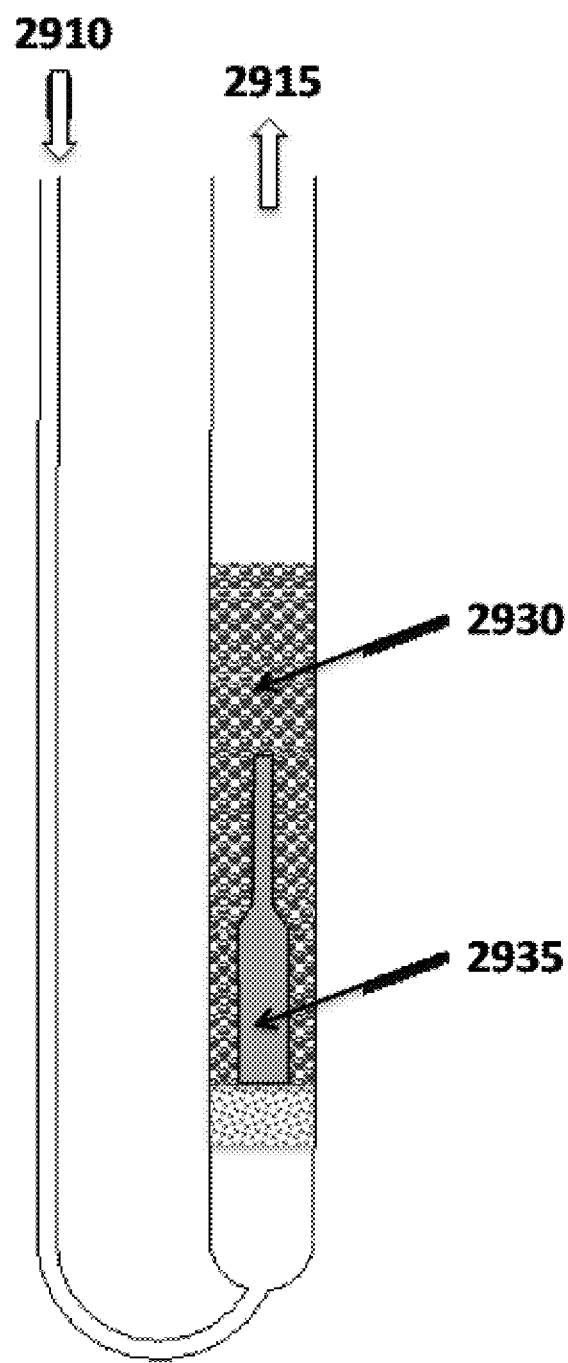

The bed packing in FIG. 29C uses a combination of a catalyst bed 2930 and an inert material 2935 that is essentially non-porous or has a high flow resistance. The catalyst bed can surround the inert material, which can be any shape, including wider nearer the entrance of the reactants and narrower nearer the exit of the products. This strategy creates an uneven distribution of catalyst and gas flow across the tube section. The geometry of FIG. 29C can be useful for moderating the temperature in the active catalyst bed by creating a gradient of gas linear velocity within the catalyst bed. The gradient has a higher gas flow rate at the inlet than at the outlet of the bed. This geometry also has increased heat exchange area as the volume of the reactor that is used is increased. The geometry of FIG. 29C can allow for flexibility in the design of the flow rate gradient from the inlet to the outlet of the tube. It can also be cost effective compared to varying the diameter of the metal tube by welding multiple tube sections together.

Figure 29D:
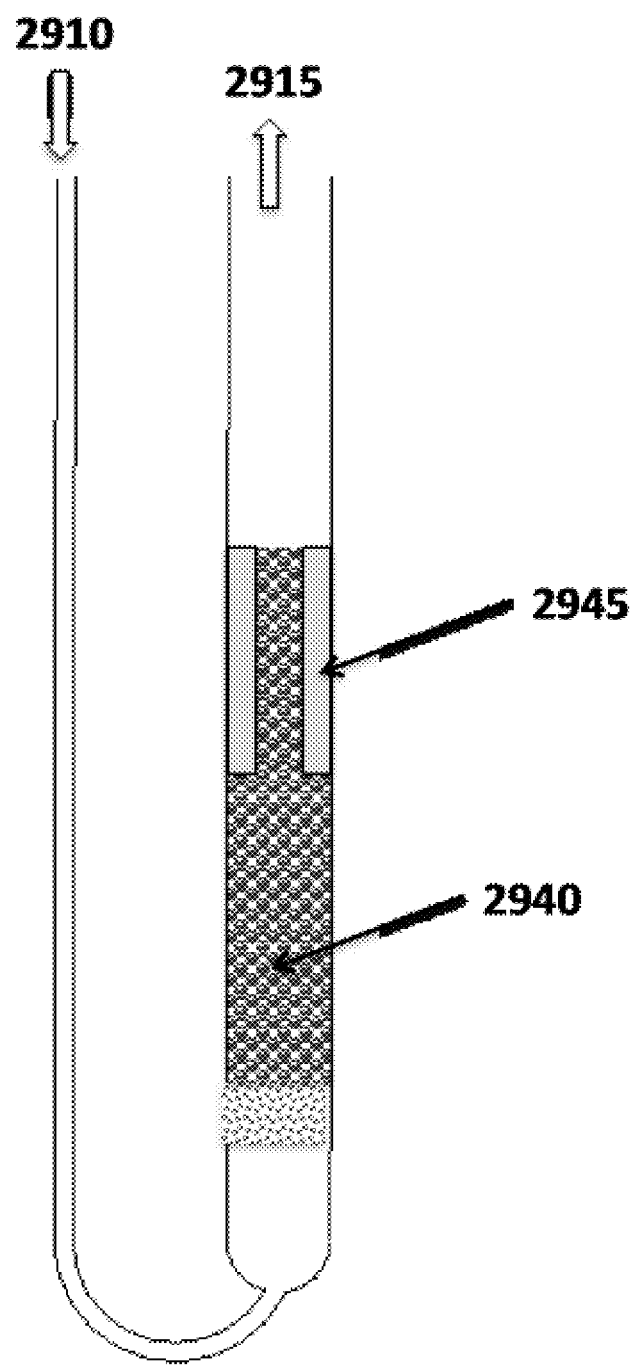

The bed packing shown in FIG. 29D uses a combination of a catalyst packed bed 2940 and a thermally insulating material 2945. This packing geometry can increase the residence time of the process gas at high temperature once the oxygen in the feed is depleted. This can be desirable because of the endothermic cracking of ethane to ethylene taking place in the back end of OCM reactor. Adding thermal insulation at a location where most of the oxygen is depleted increases the ethylene yield of the tubular reactor.

Pre-Heating Devices, Systems and Methods

Another aspect of the present disclosures provides heating devices, systems and methods. Such devices, systems and methods may be employed for use in pre-heating reactant streams prior to an OCM reaction. Pre-heating devices, systems and methods of the present disclosure can be used separately or in conjunction with other pre-conditioning approaches of the present disclosure, such as mixing. For example, a pre-heater can be integrated with a mixer. As another example, a pre-heater can be separate from a mixer and situated upstream or downstream of the mixer but situated prior to an OCM reactor.

In some embodiments, streams comprising an oxidizing agent (e.g., $O_2$, which may be provided by way of air) and/or methane are heated by reaction heat prior to being mixed. This can advantageously reduce the amount of reaction heat that is lost as waste heat, which can decrease the amount of energy that is used in external heat exchangers to pre-heat the streams.

For example, an air stream or methane stream can be heated by heat from an OCM reactor. As another example, a mixed stream comprising air and methane is heated by heat from an OCM reactor. The air and/or methane stream can be directed along a location that is in thermal communication with a catalyst bed to provide heat to the air and/or methane stream prior to mixing or an OCM reaction to generate $C_{2+}$ compounds. In some examples, the air and/or methane stream are directed to a heat exchanger that is integrated with the OCM reactor, where at least a portion of the heat from the OCM reaction is transferred to the air and/or methane stream.

In some embodiments, a system for performing an OCM reaction to generate $C_{2+}$ compounds comprises an OCM reactor comprising an OCM catalyst that facilitates the OCM reaction to generate the $C_{2+}$ compounds, and an injector comprising a fluid flow conduit that directs a first gas stream through at least a portion of the OCM reactor to one or more openings that are in fluid communication with the OCM reactor. The fluid flow conduit is in thermal communication with the OCM reactor, and the first gas stream comprises one of methane and an oxidizing agent. In some examples, the oxidizing agent includes oxygen ($O_2$). The system further comprises a gas distribution manifold comprising one or more openings that are in fluid communication with the one or more openings of the injector and the OCM reactor. The gas distribution manifold directs a second gas stream into the OCM reactor. The second gas stream comprises the other of methane and the oxidizing agent.

An OCM reactor can be integrated with a heat exchanger, which can enable reactant streams to be preheated by heat liberated from a reactor to optimize a downstream reaction, such as an OCM reaction. For example, a stream comprising an oxidizing agent (e.g., $O_2$), such as an air stream, can be heated with a stream comprising a hydrocarbon stream (e.g., methane) prior to mixing. The mixed stream can then be directed to the OCM reactor, as described above or elsewhere herein.

A mixture of methane and oxygen can be reactive above a given temperature. The auto-ignition temperature of methane in air is about 580° C. at atmospheric pressure. Under such conditions, bringing methane in contact with oxygen at such elevated temperature may lead to premature reaction, such as partial or complete combustion, leading to potentially undesirable products, such as CO and $CO_2$. However, it may not be desirable to decrease the temperature of a methane and/or $O_2$ stream (e.g., below the auto-ignition temperature) as this may decrease the overall conversion in an OCM process.

The present disclosure provides various approaches for reducing, if not eliminating the auto-ignition of methane. In some cases, the time that methane is in contact with $O_2$ is reduced while the temperature of the methane and/or $O_2$ streams is maintained at a requisite level to effect a given degree of conversion. The light off temperature for an OCM reaction can be a function of linear flow rate through the OCM reactor (e.g., catalyst bed). Similarly, minimal inlet temperature under operating conditions may be affected by the linear flow rate though the OCM reactor.

In some embodiments, an inlet section is used to process a fraction of the inlet gas feed (e.g., less than 33%) at reduced local flow rate and inject the reaction product in a second section of the OCM reactor where unreacted bypass feed will contact a hotter reacted product stream (e.g., stream containing $C_{2+}$ compounds), such as in a counter flow fashion. The hotter product stream can be used to promote the OCM reaction by increasing the OCM reactor temperature relative to the reactor feed inlet. In some examples, an artificially created bypass channel is provided through at least a portion of an OCM reactor, which can decrease the feed linear flow rate in the front end of the OCM reactor compared to the feed linear flow rate in the back of the OCM reactor.

Figure 7A:
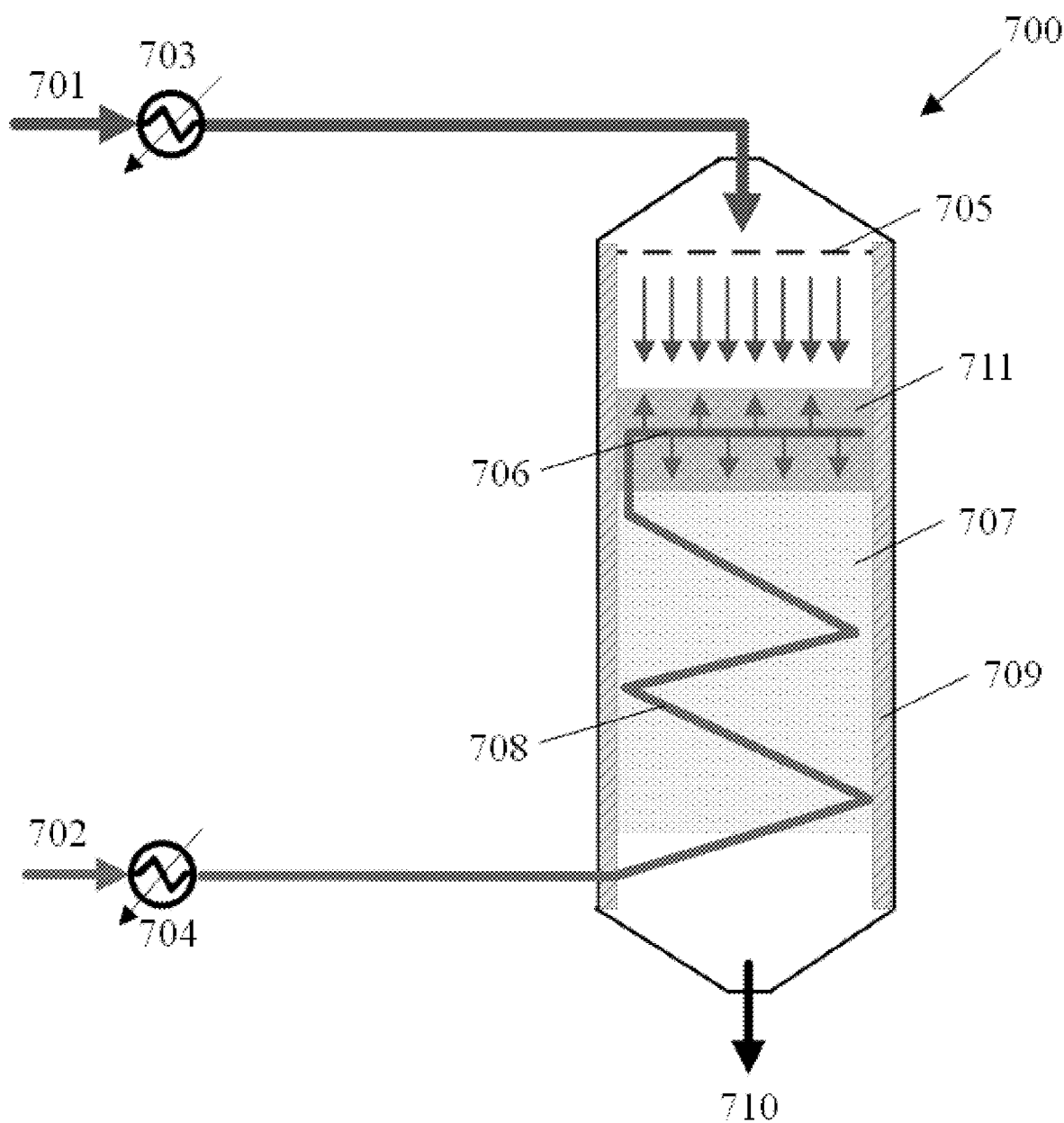
FIG. 7A shows an OCM system with a fluid flow conduit that is directed through an OCM catalyst bed and in fluid communication with a gas distributor.

OCM systems of the disclosure can be integrated with heat exchangers, which can enable heat liberated in an OCM reaction to be used to heat (or preheat) methane and/or an oxidizing agent (e.g., 0, which may be provided by air) prior to an OCM reaction. In some embodiments, heat generated from an OCM reaction is used to increase a reactor inlet gas temperature. FIG. 7A shows an OCM system 700 comprising a methane stream 701 and an air stream (comprising $O_2$) 702 that are each directed through heat exchangers 703 and 704, respectively, where each of the streams 701 and 702 is preheated. Next, the methane stream 701 is directed to a feed flow distributor 705 of the OCM system 700. The feed flow distributor 705 can be, for example, in the form of a showerhead, which can include a plurality of concentric holes. The feed flow distributor 705 can provide a uniform flow of methane. The air stream 702 is directed into the OCM system 700 to an air distributor 706, which provides streams of air upward towards the feed flow distributor and downward towards a catalyst bed 707. The catalyst bed 707 can include an OCM catalyst, as described elsewhere herein. The air stream 702 is directed to the air distributor 706 along a conduit 708 that includes a fluid flow that is in thermal communication with the catalyst bed 707. The conduit 708 can be a tube or channel that can be isolated from the catalyst bed 707. In some cases, multiple conduits 708 in fluid communication with the air distributor 706 can be used.

The dimensions of the conduit 708 can be selected to provide fluid flow properties that provide for preheating and provide flow characteristics that may be optimized for the OCM reaction. For instance, the length of the conduit 708 in the catalyst bed 707 can be selected such that the residence time of air (or other fluid) is sufficient to provide requisite preheating.

The air distributor 706 can be a hollow device that includes a chamber in fluid communication with a plurality of fluid flow paths that lead from the chamber to a location external to the air distributor 706. The air distributor 706 can be as described above or elsewhere herein, e.g., in the context of FIGS. 3A-3C.

The system 700 can include a reactor liner 709 that can insulate the system 700 from the external environment. The liner 709 can thermally insulate the distributors 705 and 706, and catalyst bed 707, from the external environment.

In the catalyst bed 707, methane and oxygen react to form $C_{2+}$ compounds in an OCM process. The $C_{2+}$ compounds along with other compounds, such as unreacted methane and oxygen, are directed out of the system 700 in a product stream 710.

Figure 7B:
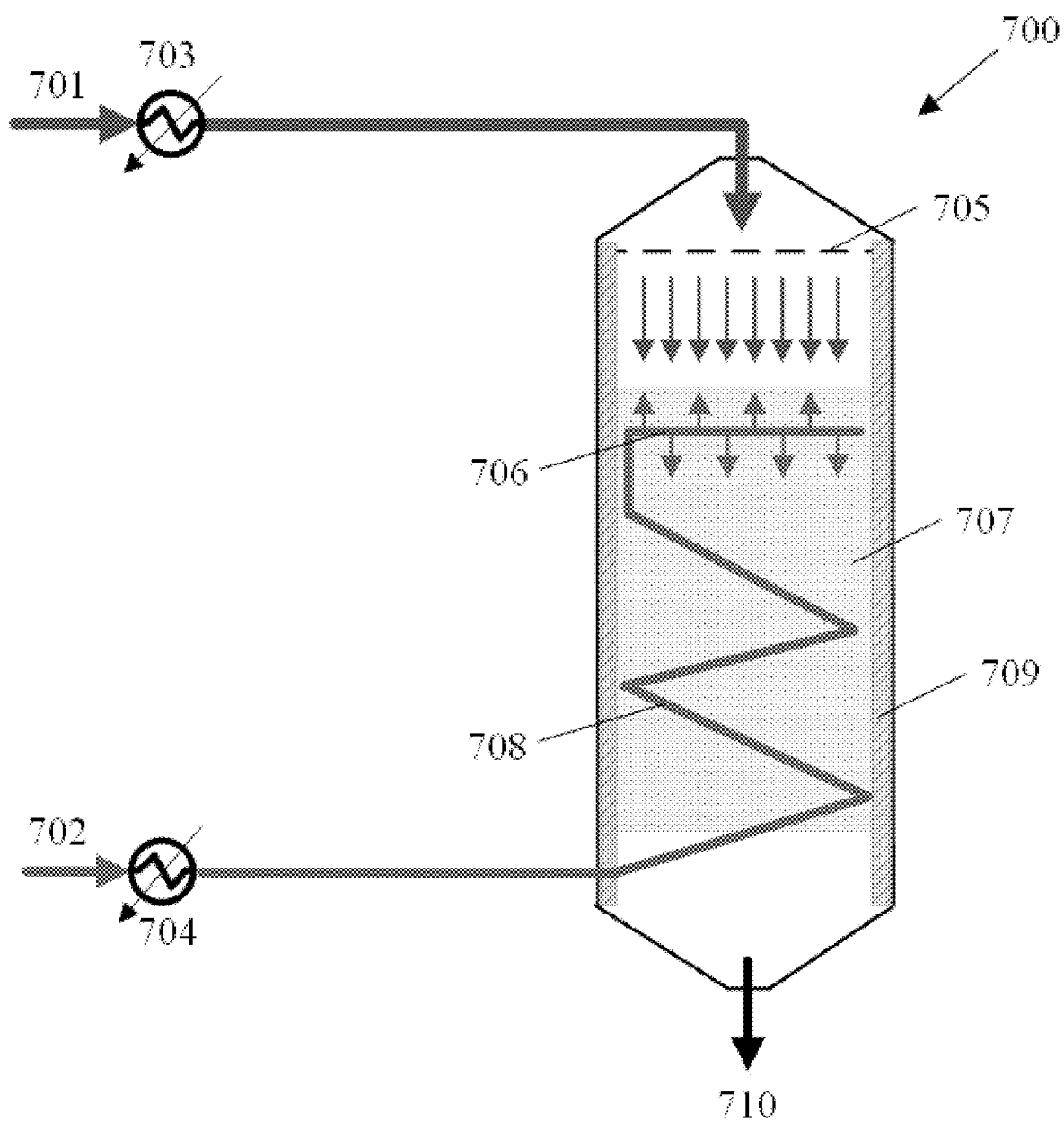
FIG. 7B shows the OCM system of FIG. 7A with the gas distributor situated in the catalyst bed.

In the example of FIG. 7A, the air distributor 706 is disposed in an inert packing medium 711. The inert packing medium 711 can include, for example, aluminum oxide (e.g., alumina) or silicon oxide (e.g., silica) beads. As an alternative, the air distributor 706 can be disposed at a location between the feed flow distributor 705 and the catalyst bed 707, or within the catalyst bed 707. In FIG. 7B, the air distributor 706 is situated in the catalyst bed 707. The air distributor 706 is situated in the catalyst bed 707 at a location that is at or adjacent to the point at which methane enters the catalyst bed. However, other locations may be employed. For example, the air distributor 706 can be situated at a location that is at or at least about 5%, 10%, 20%, 30%, 40%, 50%, 60%, 70%, 80%, or 90% of the length (i.e., from top to bottom in the plane of the figure) of the catalyst bed 707.

As another alternative, the air distributor 706 can be disposed at a location between the feed flow distributor 705 and the catalyst bed 707. For example, the air distributor 706 can be disposed in an unfilled space between the feed flow distributor 705 and the catalyst bed 707 (see, e.g., FIG. 3A and corresponding text).

During an example operation of the system 700, air is directed along the conduit 708 to the air distributor 706. As air moves along a portion of the conduit 708 that is situated in the catalyst bed 707, heat liberated by the OCM process is used to pre-heat the air.

As an alternative, methane can be directed through the conduit 708 to the distributor 706 such that methane is preheated. Air can be directed along the stream 701 to the feed flow distributor 705.

As another alternative, multiple conduits 708 may be provided for each of methane and air, and both methane and air are directed along separate conduits 708 through the catalyst bed 707 for heating prior to mixing. Methane and air can be mixed in a distributor, such as the distributor 706 that is in fluid communication with both conduits 708. In such a case, methane and oxygen in air may be heated to a temperature that is selected to provide a given conversion during an OCM reaction. Methane and oxygen may be precluded from contact until substantially close to the catalyst bed 707 so as to reduce, if not eliminate, auto-ignition of methane.

Figure 8:
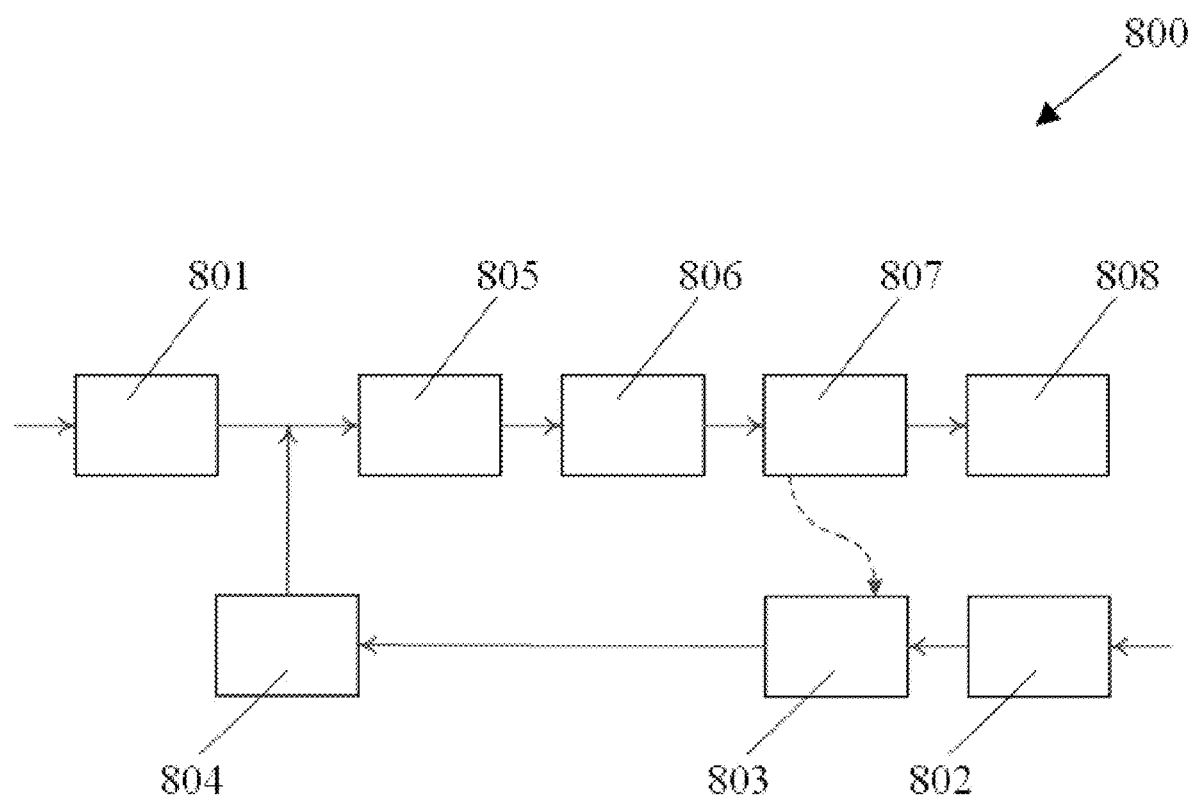
FIG. 8 shows an OCM system in which OCM reaction heat is used to heat inlet air.

FIG. 8 shows an OCM system 800 in which OCM reaction heat is used to preheat air. The OCM system 800 comprises a methane inlet 801 and air inlet 802. The methane inlet 801 has a temperature T1 and the air inlet 802 has a temperature T2. Air from the air inlet 802 is directed along a conduit 803 where it is preheated using reaction heat (kQ). The preheated air is then directed to an air distributor 804. Air from the air distributor 803 is mixed with methane from the methane inlet 801 to yield a mixed stream 805, which is directed to a catalyst bed 806. In some cases, methane from the methane inlet 801 is directed to a feed flow distributor (not shown), as described elsewhere herein. In the catalyst bed 806, methane and oxygen (in air) undergo an OCM reaction to yield $C_{2+}$ compounds and heat. In a heat exchanger 807, at least a portion (kQ) of the liberated heat is directed to preheat air in the conduit 803. Next, the products from the OCM process are directed out of the system 800 along an outlet 808. In some cases, the heat exchanger 807 is integrated with the catalyst bed 806 such that the catalyst bed exchanges thermal energy with the conduit 803 directly.

Figure 9:
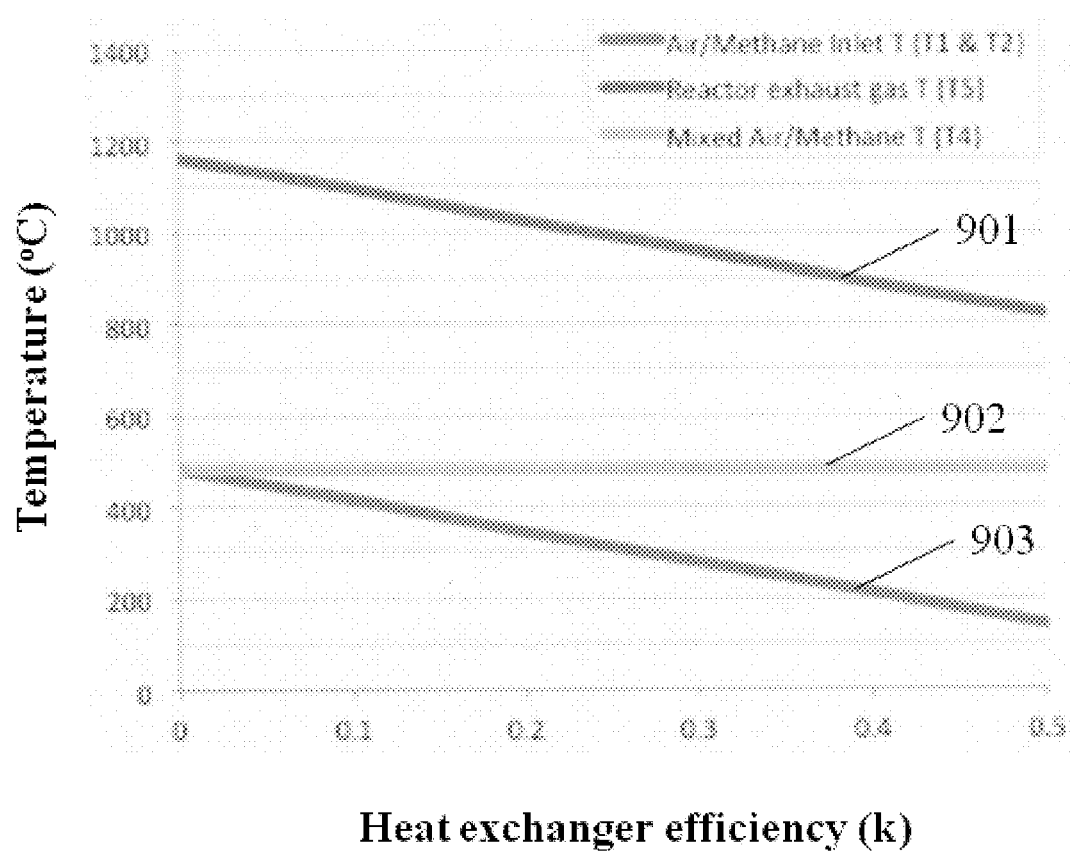
FIG. 9 is a graph of temperature (y-axis) as a function of heat exchanger efficiency (x-axis) for various elements the OCM system of FIG. 8.

FIG. 9 is a graph of temperature (y-axis, ° C.) as a function of heat exchanger efficiency (x-axis, k (unity)) for various elements the system 800. A first plot 901 shows temperature as a function of heat exchanger efficiency for the outlet 508. A second plot 902 shows temperature as a function of heat exchanger efficiency for the mixed stream 805. A third plot 903 shows temperature as a function of heat exchanger efficiency for the methane and air inlets 801 and 802, respectively.

In some cases, OCM reaction selectivity is maximized at high catalyst temperatures in the 850° C. to 950° C. range but begins to diminish at temperatures in excess of this "sweet spot" range. Under adiabatic reaction conditions, the peak catalyst temperature is proportional to the feed oxygen concentration since the reaction is operated under oxygen limiting conditions. Thus the peak catalyst temperature can be operated in a desired or otherwise predetermined temperature range to maximize selectivity by setting the feed $CH_4/O_2$ ratio. In any commercial reaction, the desire may be to maximize product yield. For the OCM reaction, yield is selectivity multiplied by the methane conversion. Higher methane conversions can result in higher yields provided that the OCM catalyst is operated such that the OCM reaction selectivity is optimized for given reaction conditions. The internal heat exchanger concept may be used to operate at higher methane conversions within at optimum selectivity. The plots show that a low efficiency heat exchanger (as may be integrated with an OCM reactor) may be employed for use in an OCM reaction. In this example, without internal heat exchange, the catalyst temperature reaches about 1200° C., a temperature far in excess of the optimum selectivity. Employing about 31% internal heat exchange (k=0.31), the catalyst temperature is reduced to about 950° C., a temperature at the edge of the optimum selectivity. Without internal heat exchange to remain within the optimum selectivity, the methane conversion is limited to about 10%, while with 31% internal heat exchange the methane conversion can be advantageously at about 15%, which an increase of about 50%.

Figure 10A:
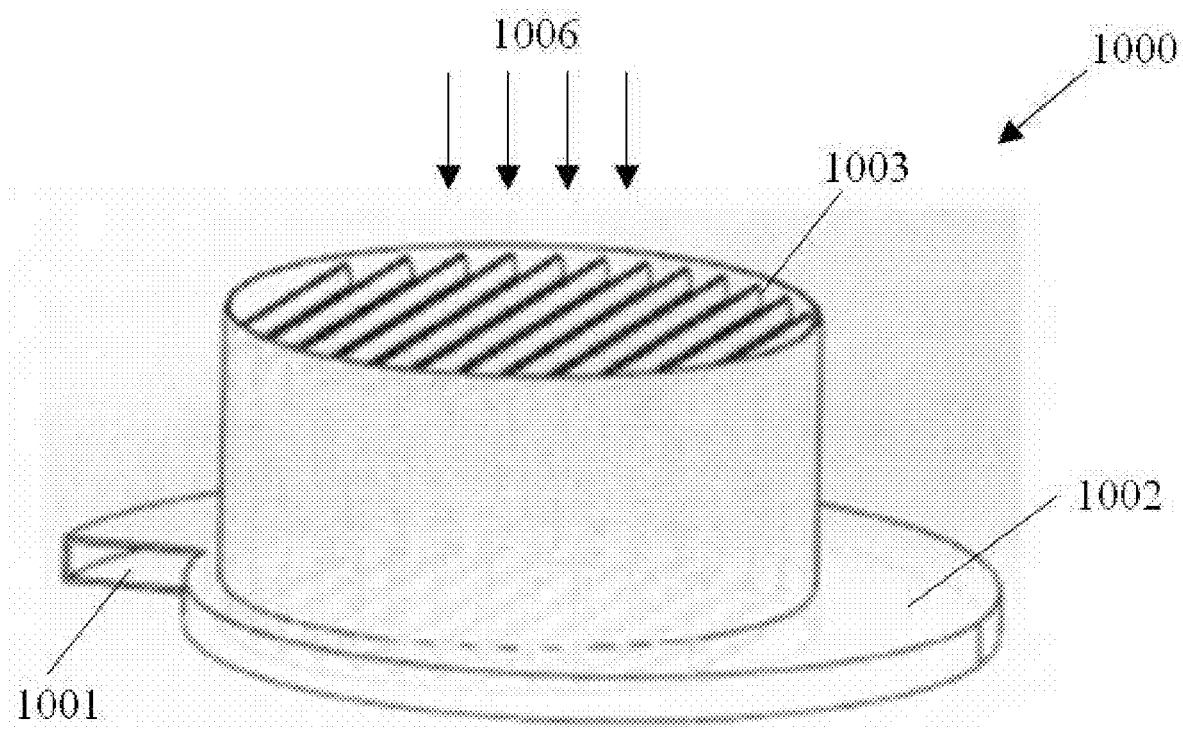
FIGS. 10A, 10B and 10C are isometric, side and cross-sectional side views, respectively, of an OCM system that is an integrated heat exchanger and gas injection system.
Figure 10B:
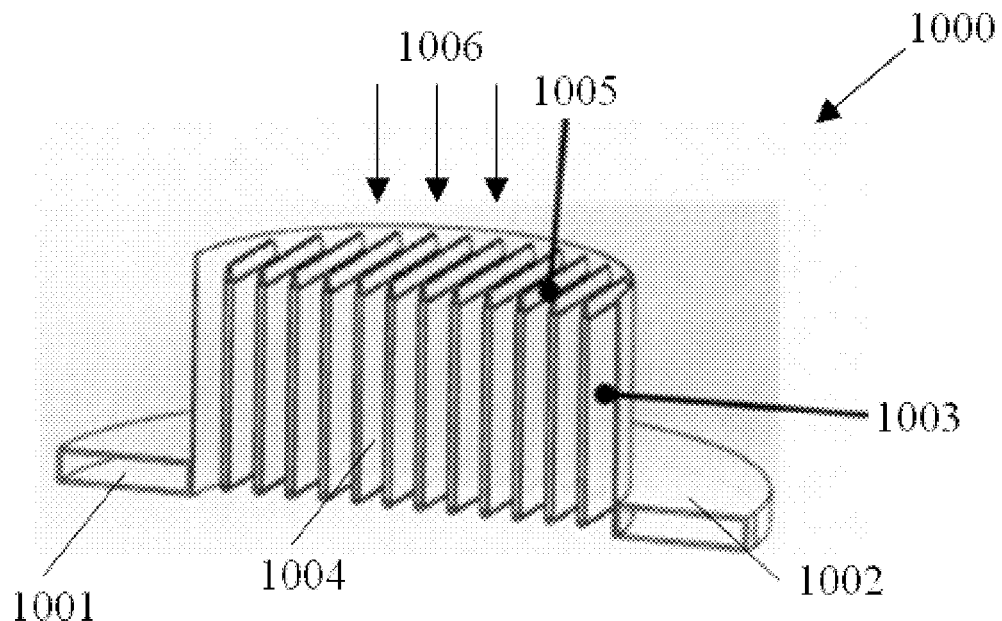
Figure 10C:
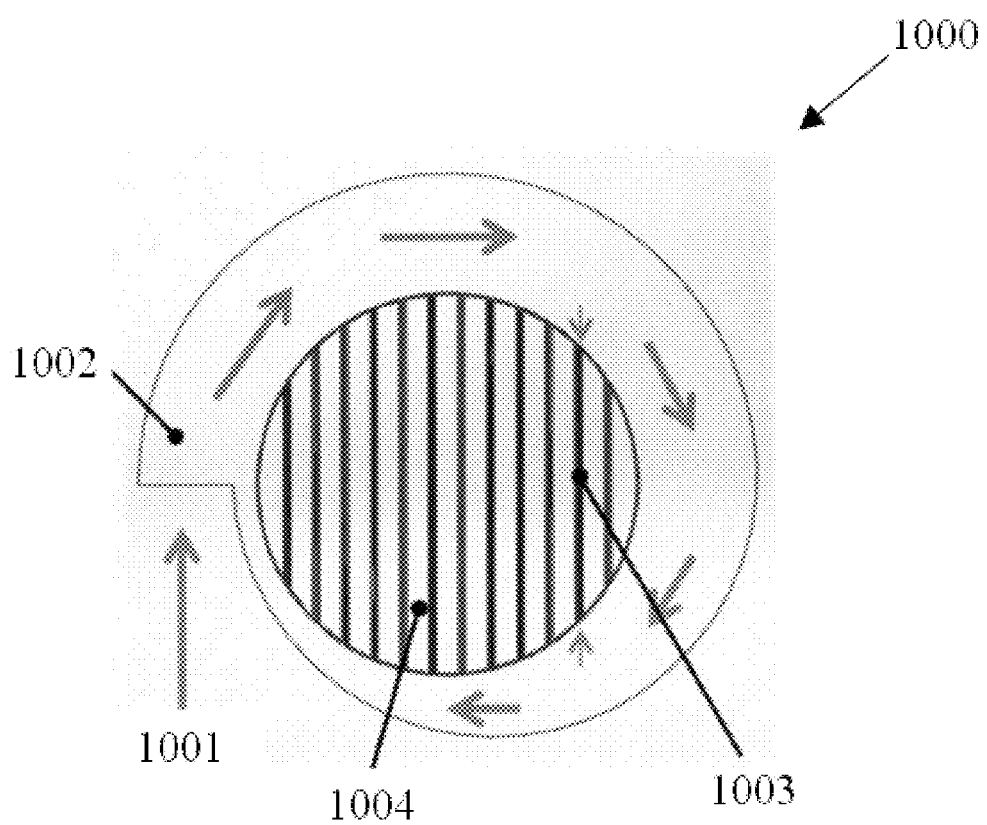

A heat exchanger can be integrated with a mixer and OCM reactor. FIGS. 10A, 10B and 10C are various views of an OCM system 1000 that is an integrated heat exchanger and gas injection system. FIG. 10A is an isometric view, FIG. 10B is a cross-sectional side view, and FIG. 10C is a top view of the system 1000. The system 1000 comprises a gas inlet 1001 that is in fluid communication with a fluid flow path 1002. The fluid flow path 1002 can include a chamber that is in fluid communication with the inlet 1001 and the ribs 1003. The system 1000 includes a plurality of ribs 1003. Each of the ribs 1003 is in fluid communication with the fluid flow path 1002 through one or more openings (e.g., holes or slits) at the ends of the ribs 1003. The ribs 1003 can each be hollow. In the illustrated example, spaces between the ribs 1003 are filled with an OCM catalyst.

A fluid (e.g., air) is directed into the system 1000 through the gas inlet 1001 and is directed through the fluid flow path 1002 (see, e.g., FIG. 10C). From the fluid flow path 1002, the fluid is directed to each rib 1003. The fluid is then directed to an end 1005 (see, e.g., FIG. 10B) of each of the ribs 1003, where it is ejected out of the ribs 1003 via one or more openings (e.g., holes or slits) at the end of the ribs 1003. At the end 1005, the fluid can mix with an additional fluid 1006 that is directed from a top portion of the system 1000.

In some examples, the fluid directed from the gas inlet 1001 through the fluid flow path 1002 includes an oxidizing agent, such as oxygen ($O_2$). The fluid can be air. The additional fluid 1006 can be methane. Fluid mixing can take place at the end 1005.

The ends 1005 are situated towards the top of the air foils. With such configuration, the fluid can be directed through the ribs 1003 along a direction that is substantially opposite to the direction of flow of the additional fluid 1006. As an alternative, or in addition to, the ribs 1003 can include openings situated along the sides or at the bottom of the ribs 1003 such that the fluid exits the ribs at the sides or at the bottom.

The ribs 1003 can have various shapes, such as airfoil shapes. The ribs 1003 can be formed of a ceramic or composite material, such as, for example, alumina, zirconia and/or silicon carbide. The ribs 1003 can be airfoils.

Figure 11A:
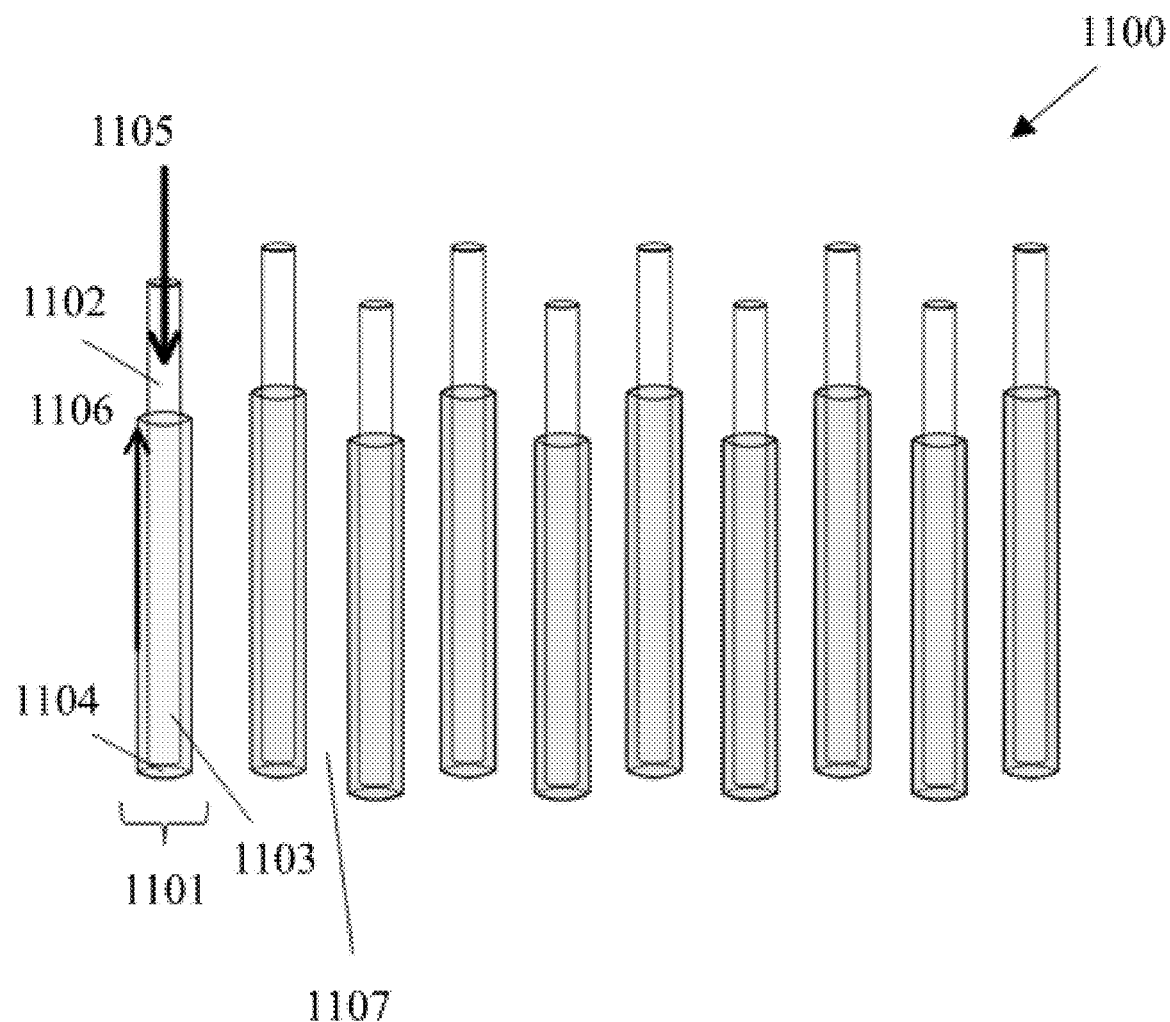
FIG. 11A shows an OCM reactor that is integrated with a heat exchanger.

FIG. 11A shows an OCM reactor that is integrated with a heat exchanger 1100. The heat exchanger 1100 comprises a plurality of flow reversal pipes (ten shown). An individual flow reversal pipe 1101 includes an inner tube 1102 circumscribed by an outer tube 1103. A bottom portion 1104 of the outer tube 1103 is closed. The pipe 1101 includes a fluid flow path between the inner tube 1102 and the outer tube 1103. The fluid flow leads from an inlet 1105 to the bottom portion 1104 and upward to an outlet 1106.

The heat exchanger 1100 includes a space 1107 between the pipes 1101 that is filled with an OCM catalyst (not shown). The space 1107 can be at least partially or complete shown). The space 1107 can be at least partially or completely filled with the OCM catalyst. For example, the space 1107 can be at least partially or completely filled with catalyst particles in a fluidized bed. The fluid flow path can be in thermal communication with the OCM catalyst such that heat liberated in an OCM reaction is directed to the fluid flow path and a fluid in the fluid flow path.

The inlet 1105 can be at or above the OCM catalyst, such as a catalyst bed of the OCM catalyst. As an alternative, the inlet 1105 can be external to the OCM catalyst.

The outlet 1106 can be in the OCM catalyst or above the OCM catalyst. In some situations, the outlet 1106 is within the OCM catalyst, such as a packed bed. In such a case, the fluid stream can exit the individual pipe 1101 in the OCM catalyst.

During use, a fluid stream (e.g., air or methane) is directed from the inlet 1105 through the fluid flow path between the inner 1102 tube and the outer tube 1103 to the outlet 1106. During an OCM reaction, heat may be generated, which can be directed to the fluid stream in the fluid flow path. The heat can be used to heat the fluid in the fluid stream. At the outlet 1106, the fluid can be brought in contact with another fluid (e.g., methane) in a fluid stream external to the individual pipe 1101 and mixed to provide a mixed stream, which can be directed to the OCM catalyst in the space 1107 to provide $C_{2+}$ compounds and heat.

The heat exchanger 1100 can include at least 1, 2, 3, 4, 5, 6, 7, 8, 9, 10, 15, 20, 30, 40, 50, 60, 70, 80, 90, 100, 200, 300, 400, 500, or 1000 pipes 1101, and in various arrangements. In some examples, the pipes 1101 are in a side by side arrangement, circumferential arrangement, or a combination of the two arrangements.

In some cases, by using an open tube inserted into a capped tube, fluid flow can be forced to reverse direction between the inlet 1105 and the outlet 1106. By inserting the flow reversal tube 1101 in an OCM catalyst comprising a packed bed, a pressure differential can be created under flow conditions that can provide the pressure drop to drive the fluid from the inlet 1105 to the outlet 1106.

In some situations, when a large rise in temperature is obtained through an OCM reaction, the temperature of the stream exiting the individual pipe 1101 can be significantly higher than the temperature of the stream entering the individual pipe 1101.

Figure 11B:
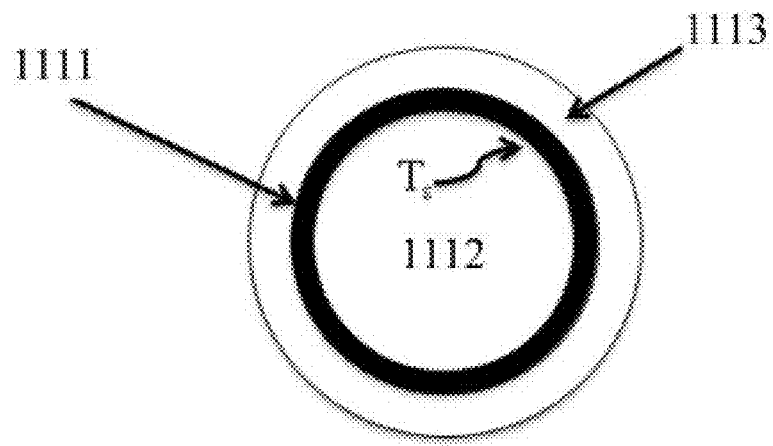
FIGS. 11B and 11C are schematic cross-sectional and side views, respectively, of an integrated OCM reactor and heating element.
Figure 11C:
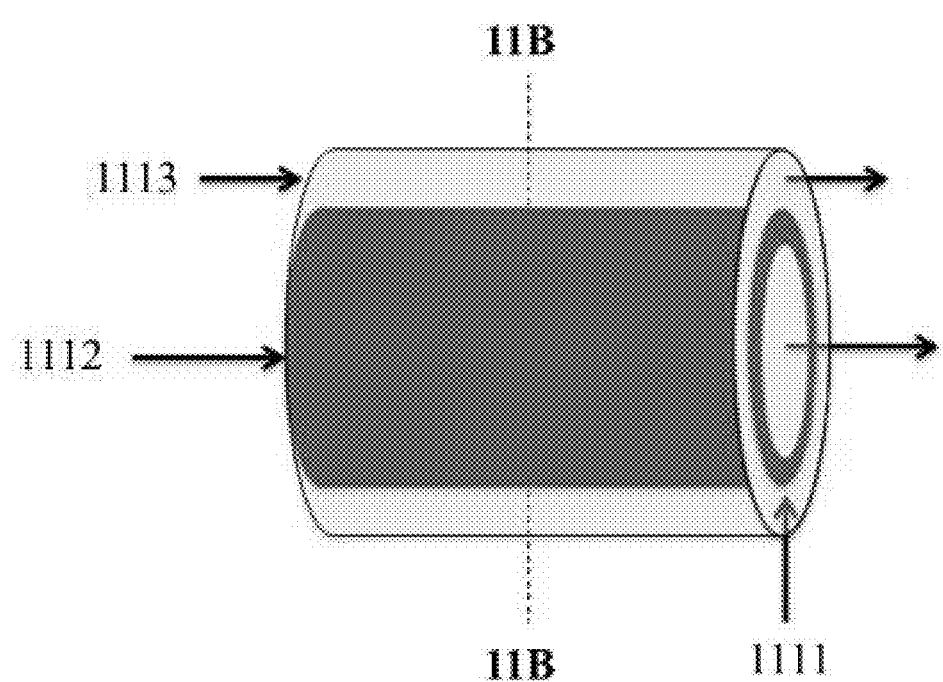

FIGS. 11B and 11C are schematic cross-sectional and side views, respectively, of an integrated OCM reactor and heating element. The heating element includes an OCM catalyst 1111 that is in between an inner fluid flow path 1112 and an outer fluid flow path 1113. The arrows indicate the direction of fluid flow. An OCM gas (e.g., methane and oxygen) can be directed along the inner fluid flow path 1112 to generate $C_{2+}$ compounds in an OCM process with the aid of an OCM catalyst 1111. A heating exchange fluid can be directed along the outer fluid flow path 1113 in a parallel flow (as illustrated) or cross-flow configuration with respect to fluid flow along the inner fluid flow path 1112. Heat generated during the OCM process can be transferred to the heat exchange fluid in the outer fluid flow path 1113. The heat exchange fluid can include one or more OCM gases (e.g., methane and $O_2$), products of the OCM reaction (e.g., $C_{2+}$ compounds), or a fluid that is configured to transfer energy to or remove energy from the OCM catalyst 1111. The OCM catalyst 1111 can be a standalone inner tube or a coating on a support material.

The surface of the OCM catalyst 1111 that is exposed to the inner fluid flow path 1112 can have a temperature that increases from an inlet (left portion) to an outlet (right portion) of the reactor of FIGS. 11B and 11C. The temperature of a heat exchange fluid flow through the outer fluid flow path 1113 can increase or decrease based on the direction of fluid flow. If the heat exchange fluid is flowing in parallel fashion with respect to fluid flow in the inner fluid flow path 1112, then the temperature of the heat exchange fluid can increase from inlet (left portion) to outlet (right portion).

Integrated heat exchangers of the disclosure enable the creation and maintenance of a hot spot within an OCM catalyst, allowing an OCM reactor to be operated with a reduced temperature inlet compared to cases in which an integrated heat exchanger is not used. In some implementations, the inlet gas is heated to the necessary temperature by a heat exchanger, which enables the OCM reaction in a fixed bed reactor. This temperature can be between 300° C.-550° C. This approach may be sensitive to the oxygen concentration in the feed and require substantially short residence times from the heater to the catalyst bed to prevent combustion, such as via auto-ignition. The heat exchanger capital cost may also be an issue. For example, the inlet temperature can be about 350° C. for a fluidized bed reactor (in some cases with relatively high reverse flow direction heat transfer), which can enable increased conversion in an adiabatic bed as well as minimizing the risk of premature ignition, especially when using pure $O_2$ as the oxidizing agent in the OCM reaction.

In some embodiments, a heating element is lined externally with an OCM catalyst (e.g., coated or a sleeve is placed over heater surface). The heating element can have a relatively low heat transfer efficiency so as to maintain a high skin (or boundary layer) temperature of the OCM catalyst that externally coats the heating element. As the inlet gas passes adjacent to the heating element, gas near the surface of the catalyst can be heated to a temperature that is at or near the skin temperature, which can initiate the OCM reaction and release heat that can mix with the bulk gas, uniformly heating the process gas stream. The skin temperature of the OCM-catalyst lined heating element can be sufficiently high so as to help ensure that the OCM reaction is highly selective (e.g., from about 750° C. to about 900° C.) for a desirable product (e.g., $C_{2+}$ compounds). In some cases, as the OCM reaction proceeds on the heating element surfaces, it produces heat that increases the inlet gas temp as well as produces desirable OCM reaction products (e.g., $C_{2+}$ compounds, water). This can be an approach to both reduce inlet heat exchanger capital costs as well as enable much higher single stage conversions, because the inlet $O_2$ (or other oxidizing agent) concentration can be sufficiently high to heat the inlet gas from low temperatures (e.g., 25° C.–300° C.) to the desired reactor inlet temperature (e.g., 400° C.–600° C.). For example, ~10% conversion of methane at a C2 selectivity approaching 60% heats the inlet gas from 200° C. to 500° C. An additional 10% conversion can be attained in the fixed bed portion of the reactor, for example, resulting in a much higher single stage conversion. Heat exchangers lined with OCM catalysts of the present disclosure can take advantage of the substantially rapid OCM reaction kinetics at temperatures in excess of 750° C., which may only require a limited number of catalyst coated heating elements to heat the inlet gas, while still maintaining a substantially short residence times to prevent combustion prior to the catalyst bed. The limited number of tubes and poor heat transfer to the gas stream may keep the heating duty of the inlet gas heat exchanger low, and the exit gas from the reactor can potentially be used as the heating medium. In such a case, at least an additional heater may be required to initiate the reaction.

Integrated heat exchangers of the present disclosure can be used to transfer heat to a gas stream undergoing a homogeneous endothermic reaction, such as alkane cracking into alkenes. For example, an OCM reactor may include a cracking unit downstream of a catalyst unit comprising an OCM catalyst. The cracking unit can be heated using heat generated in the catalyst unit in an OCM reaction.

Reactors of the present disclosure can be operated or designed to operate with reduced linear velocity. Reduced linear velocity operation can promote feed pre-heating. Reduced linear velocity operation can reduce axial convective heat transfer. Reduced linear velocity operation can move the peak bed temperature location toward the front end of the bed. Reaction heat can be used for stream preheating. Reduced linear velocity operation can result in reduced oxygen consumption in low selectivity regions. Reduced linear velocity operation can increase reaction selectivity across the reactor. A reactor can operate with reduced linear velocity in part of or in the entire reactor. For example, a reactor can comprise a low linear velocity region followed by a high linear velocity region. Linear velocity can be controlled between reactor regions by changing the reactor diameter or width. A reactor can comprise an annular reactor, wherein a feed stream enters the central region and flows from the central region to the outer region.

The linear velocity can be any suitably low value, such as about 3 meters per second (m/s), about 2.5 (m/s), about 2 (m/s), about 1.5 (m/s), about 1 (m/s), about 0.5 (m/s), about 0.4 (m/s), about 0.3 (m/s), about 0.2 (m/s), about 0.1 (m/s), or about 0.05 (m/s). In some cases, the linear velocity is equal to or less than about 3 meters per second (m/s), equal to or less than about 2.5 (m/s), equal to or less than about 2 (m/s), equal to or less than about 1.5 (m/s), equal to or less than about 1 (m/s), equal to or less than about 0.5 (m/s), equal to or less than about 0.4 (m/s), equal to or less than about 0.3 (m/s), equal to or less than about 0.2 (m/s), equal to or less than about 0.1 (m/s), or equal to or less than about 0.05 (m/s).

The present disclosure provides for tubular reactor systems. A tubular reactor can comprise a single stage. A tubular reactor can employ a heat removal medium, such as molten salt. A heat removal medium can be used for heat removal from a reactor bed. A heat removal medium can be used for preheating feed streams. Tubular reactor systems can be used for reactions including but not limited to oxidative coupling of methane (OCM) and oxidative dehydrogenation of ethane (ODH). Temperature control in a tubular reactor bed can be controlled by designing different bed properties in segments. Such bed segmentation to the temperature profile can be achieved by controlling the linear velocity of the reaction gas, for example by varying the tube diameter or by including non-reactive sleeves or inserts. Bed segmentation to control the temperature profile can be achieved by controlling the thermal conductivity of the bed, for example by controlling the catalyst form (e.g., shape, size, extrudates, rings, monoliths, foams) or by choice of catalyst support (e.g., alumina, SiC, silica, magnesia). Bed segmentation to control the temperature profile can be achieved by changing the thermal conductivity of the tube wall liner. Bed segmentation to control the temperature profile can be achieved by using multiple heat removal medium sections with varying levels of turbulence or temperatures.

The present disclosure provides for heat integration by flow reversal. Flow reversal can be alternating and sequential, including periodic flow reversal and non-periodic flow reversal. Flow reversal can occur with a period of about 1 nanosecond (ns), 10 ns, 100 ns, 1 millisecond (ms), 10 ms, 100 ms, 1 second, 10 seconds, 20 seconds, 30 seconds, 40 seconds, 50 seconds, 1 minute, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, or 24 hours. High reaction temperature can result in more efficient recovery of heat from exothermic reactions. A reactor system can be operated with periodically operated flow reversal to achieve heat integration. A reactor system can simulate a moving bed reactor to achieve heat integration. A fixed bed system can be employed with a moving high temperature front formed from exothermic reaction. Travelling temperature fronts in reversed flow and simulated moving bed reactors can give rise to unsteady state reactor systems, with product gas composition changing over time.

Flow reversal reactors can be useful in managing the heat of reaction of highly exothermic reactions. They can enable heat integration where the catalyst bed serves as the gas pre-heater and as the material carrying out the catalytic conversion and generating heat in the system. OCM is a very exothermic reaction and management of the heat of reaction can be a limiting factor in the operation of fix bed adiabatic reactors under steady state conditions.

Using periodic change of flow direction across the catalyst bed can permit the operation of the catalyst under unsteady conditions. For example, the inlet gas feed temperature can drop below the extinction temperature of the catalyst bed under the pressure. The ability of using part of the bed as a heat exchanger opens the operating window of the reactor system.

Figure 33:
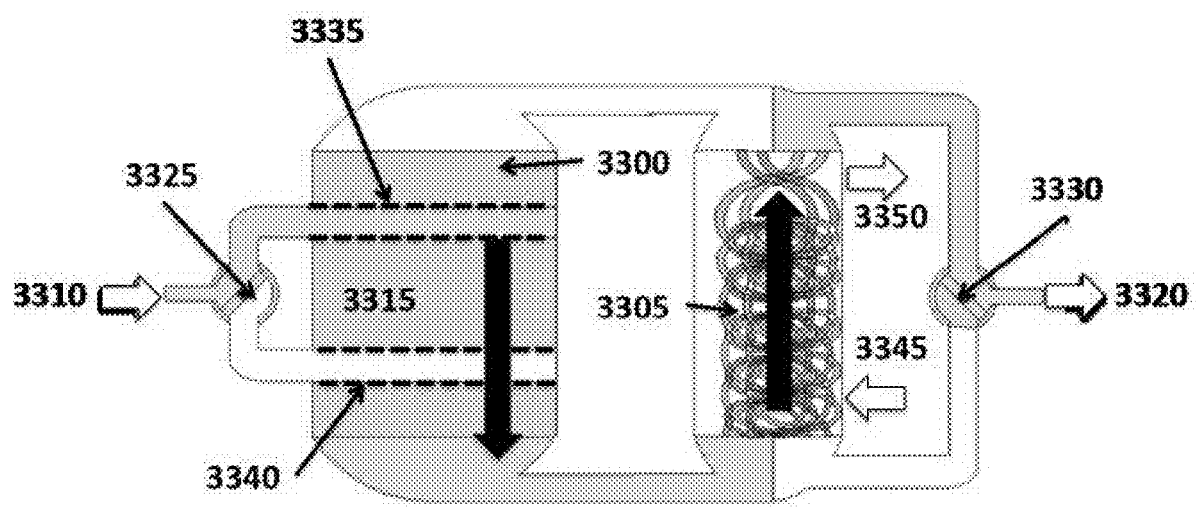
FIG. 33 shows an example of a reactor system for performing OCM with flow reversal.

FIG. 33 shows an example of a reactor system for flow reversal for OCM that includes a reactor 3300 and a heat exchanger 3305 (e.g., steam generator). FIG. 33 shows a white space representing a volume between the reactor and heat exchanger, i.e., the reactor and heat exchanger being separate vessels, however the reactor and heat exchanger can be regions within a single vessel. Reactants flow into 3310 the system and are converted to products over a catalyst bed 3315, which products flow out of the system 3320.

During normal operation, the valve switching the location of the feed injection 3325 in the catalyst bed is actuated at regular intervals. This interval can depend on the exothermicity of the reaction, the heat capacity of the catalyst bed and how far from the extinction temperature the feed conditions are. The period between flow reversals can be about 5 seconds (s), about 10 s, about 15 s, about 20 s, about 30 s, about 40 s, about 50 s, about 1 minute (min), about 2 min, about 3 min, about 5 min, about 10 min, about 20 min, about 30 min, about 40 min, about 50 min, about 60 min, about 90 min, about 120 min, or about 180 min. In some cases, the direction of flow is reversed after a period of time between about 20 seconds and about 20 minutes. The second valve selecting the exhaust flow path 3330 in the reactor may be activated simultaneously or with some delay.

As shown in FIG. 33, depending on the position of the injection valve 3325, the fluid (reactants and products) flows through the system in one of two directions. The fluid is shown as gray shading and the flow direction shown by dark black arrows. The valve can also be leaky such that at least some gas flows in both directions. The reactants can be injected into the system through a first path 3335 or a second path 3340. The reactant injection paths can be surrounded by the catalyst bed 3315. In some cases, the injection paths are the mixers described herein. The heat produced in the OCM reaction can convert water 3345 to steam 3350.

Injecting the reactants within the catalyst bed can minimize unconverted oxygen bypass when changing the flow direction, as the feed is always flowing across active catalyst bed. This can be important if very rapid switching is required (e.g., to prevent the hot spot in the reactor from exiting the mid-section). The splitting of the bed and the in-bed injection points also allow for imperfect seals in the three way valve used, as all gas going across this system can be processed and free from oxygen. This enables the use of rugged design valves and or extended number of cycle operating life.

In some cases, the product gas on the way to the product flow direction selector valve 3330 is cooled to avoid damaging the valve. A steam generating heat exchanger can be used minimizing the number of pieces of equipment 3305.

Figure 34:
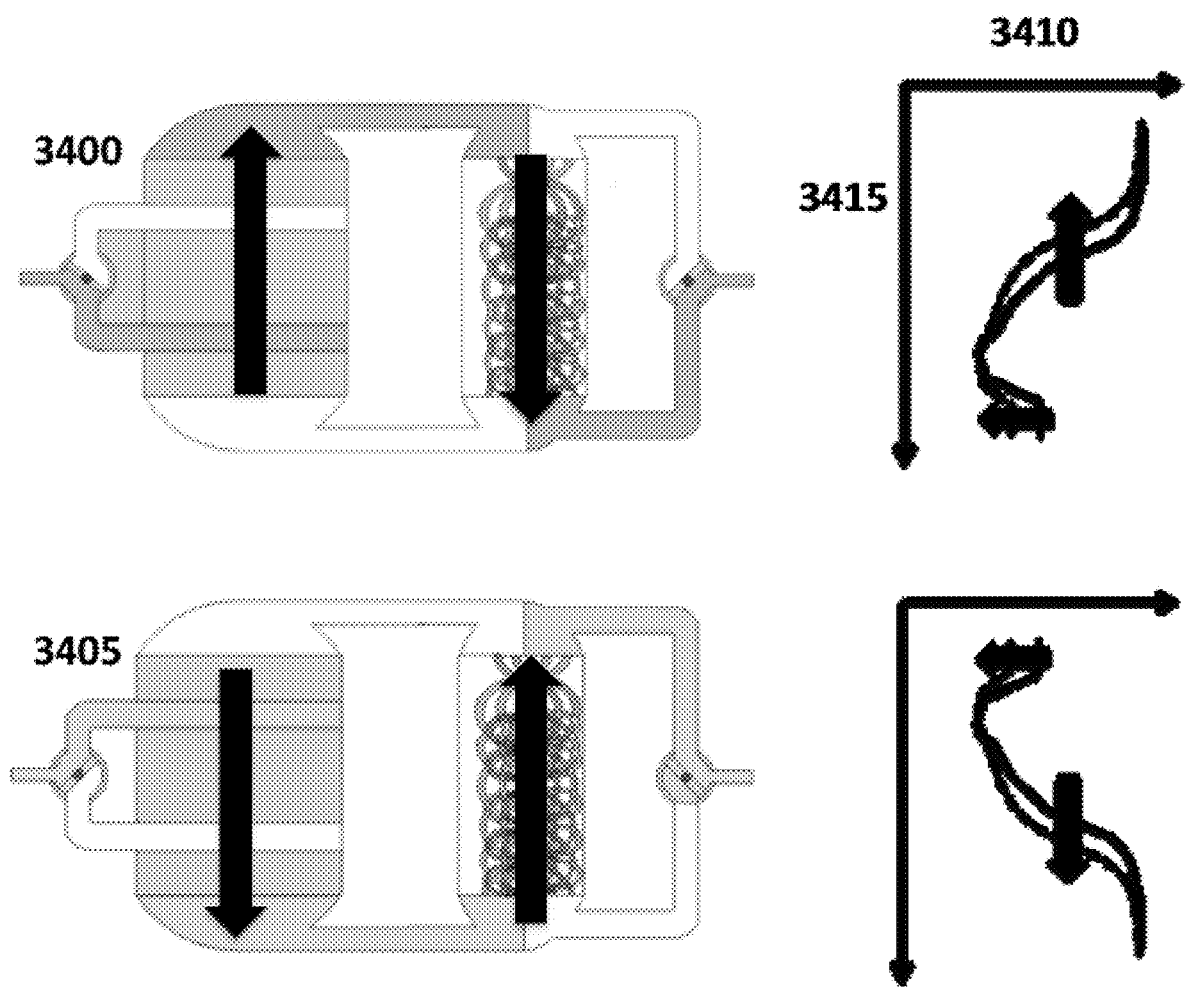
FIG. 34 shows an example of an expected temperature profile when performing the OCM reaction with flow reversal.

FIG. 34 shows the temperature profile through the catalyst bed (e.g., when the inlet gas temperature is too low to maintain a stable temperature profile through the reactor bed). The figures shows the system with fluid flowing through the system in a first direction 3400 and in a second direction 3405. The expected temperature profile is plotted to the right of each flow schematic with the temperature increasing from left to right 3410 as a function of the position in the catalyst bed from top to bottom 3415 (mirroring the schematic to the left). The cold front shifts towards the back of the bed in the flow direction. The bypass section of the bed slowly loses heat because no reaction is taking place there.

As the hottest spot in the bed is expected to be near the exit, when the flow direction is switched the hot spot will start migrating toward the other end of the reactor. By regularly reversing flow, the system can be maintain in a stable thermal oscillating mode. One benefit of using such a device and method can be an improved product yield compared to steady state operation. Another benefit can be access of operating pressures not attainable in steady fix bed operation (e.g., due to un-stability of the feed at elevated temperature and pressure). Lowering the inlet feed temperature can also improve the catalyst operating live. Furthermore, if the catalyst is susceptible to coking, changing the feed injection point can periodically de-coke the back of the catalyst bed.

Figure 12:
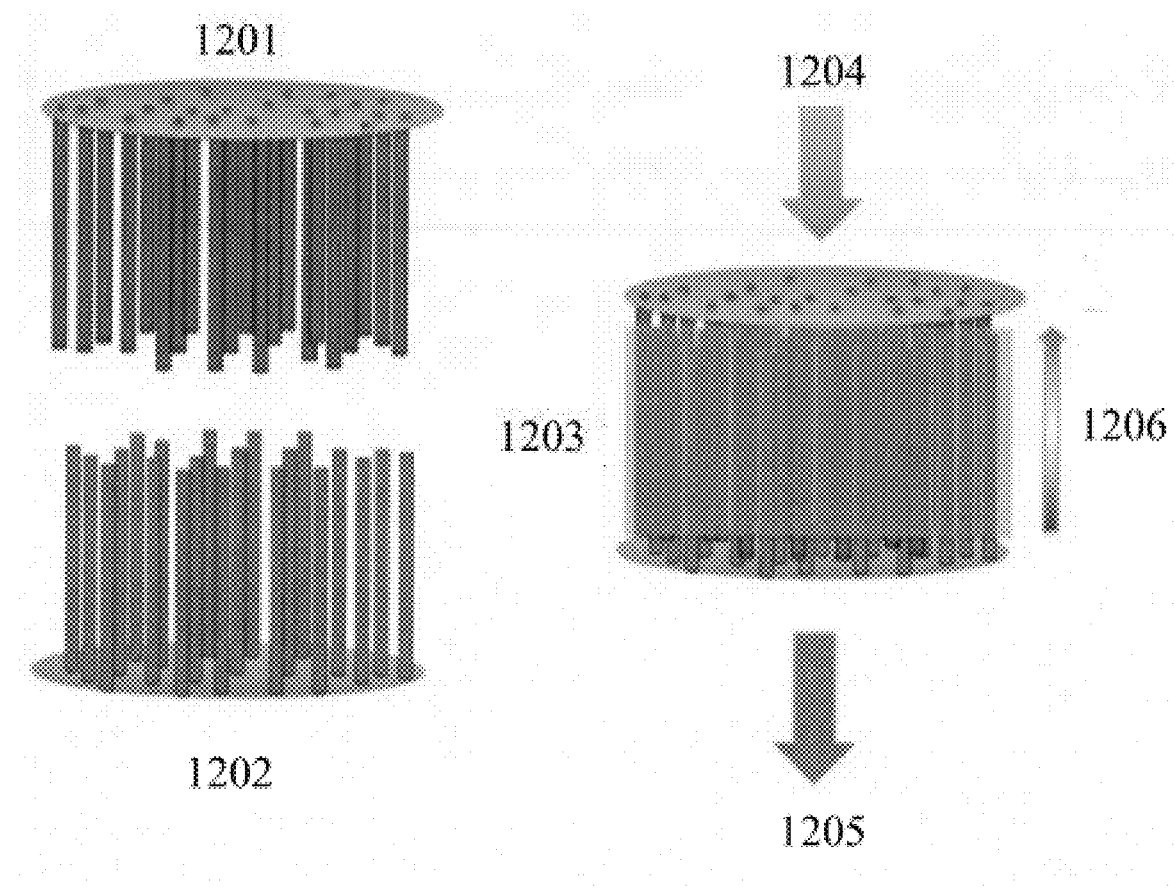
FIG. 12 shows a schematic of an OCM reactor with inlet and outlet manifolds.

A reactor system can comprise manifolds for a packed bed reactor with reverse flow. FIG. 12 shows an inlet manifold 1201 and an outlet manifold 1202. Each manifold can comprise a plurality of parallel tubes. Manifolds can be assembled into a sandwich configuration comprising a catalytic packed bed 1203. Manifolds, such as inlet and outlet manifolds, can be assembled with their tubes interdigitated with each other. Feed gas stream 1204 can be fed into the inlet manifold. Product gas stream 1205 can exit from the outlet manifold. A counter flow 1206 can be produced within the catalyst bed due to the manifold configuration. Manifolds and tubes can be made of materials including but not limited to one or more metals, dense ceramics (e.g., alumina), silicon carbide, and vitreous materials (e.g., quartz). A manifold can comprise at least about 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, or more tubes. The inlet manifold can comprise radiators mounted on the inlet side to promote heat exchange between the reactor product stream and the feed stream. Manifold reactor configurations can enable increased heat exchange between reactor inlet and reactor outlet streams. Manifold reactor configurations can enable operation at lower inlet temperatures. Manifold reactor configurations can allow operation to take advantage of the difference between light off temperature and extinction temperature in highly exothermic catalytic processes. This approach can reduce the number of heat exchanger stages needed to achieve a particular overall conversion or selectivity. This approach can improve catalyst life.

Methods for Improving Olefin Yield

An aspect of the present disclosure provides OCM systems and methods for increase the concentration of alkenes (or olefins) in $C_{2+}$ compounds outputted from an OCM reactor. This can advantageously provide $C_{2+}$ product stream that may be better suited for downstream uses, such as the commercial production of polymeric materials, as well as greater carbon efficiency of the overall process. In some embodiments, an OCM system provides improved alkene yield by alkane cracking in a catalyst unit or cracking unit. Such in situ cracking of alkanes can provide a product stream with hydrocarbon distributions tailored for various end uses.

Figure 13:
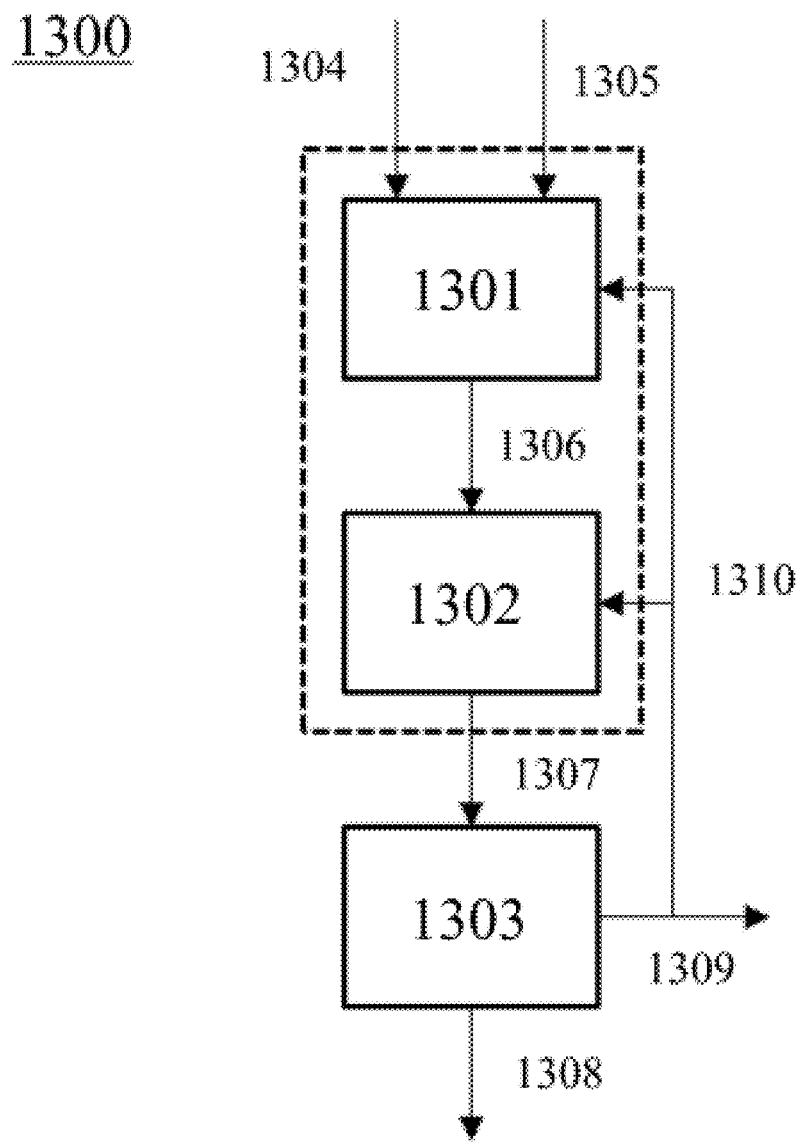
FIG. 13 schematically illustrates a system for the oxidative coupling of methane (OCM)

FIG. 13 shows an OCM system 1300 comprising an OCM reactor 1301, a cracking unit 1302 downstream of the OCM reactor 1301, and at least one separation unit 1303 downstream of the cracking unit 1302. The OCM reactor 1301 and cracking unit 1302 can be separate units or integrated as a single unit, as illustrated by the dashed box. The arrows indicate the direction of fluid flow from one unit to another. During use, a first fluid stream ("stream") 1304 comprising methane ($CH_4$) and a second fluid stream 1305 comprising an oxidizing agent (e.g., $O_2$) are directed into the OCM reactor 1301, where they react in the presence of a catalyst provided within reactor 1302 to form $C_{2+}$ compounds, which are included in a third stream 1306. The third stream 1306 can include other species, such as non-$C_{2+}$ impurities like Ar, $H_2$, CO, $CO_2$, $H_2O$, $N_2$, $NO_2$ and $CH_4$. The third stream 1306 comprises OCM products, which can include $C_{2+}$ compounds and non-$C_{2+}$ impurities.

Next, the third stream 1306 is directed to the cracking unit 1302. In the cracking unit 1302, alkanes in the $C_{2+}$ compounds can react to form $C_{2+}$ compounds with unsaturated moieties, which are outputted from the cracking unit 1302 in a forth stream 1307, such as carbon-carbon double bonds (e.g., ethylene and propylene). The fourth stream 1307 can then be directed to other unit operations for processing gases in the fourth stream 1307, such as the separation unit 1303 used for separation of at least some, all, or substantially all of the $C_{2+}$ compounds from other components in the fourth stream 1307 to yield a fifth stream 1308 and a sixth stream 1309. The streams 1308 and 1309 can each be directed to one or more storage units. The fifth stream 1308 can be directed to $C_{2+}$ storage or a non-OCM process.

Methane in the first fluid stream 1304 can be provided from any of a variety of methane sources, including, e.g., a natural gas source (e.g., natural gas reservoir) or other petrochemical source, or in some cases recycled from product streams. Methane in the first fluid stream may be provided from an upstream non-OCM process.

The fifth stream 1308 can include $C_{2+}$ (e.g., olefins) compounds at a concentration (e.g., mole % or volume %) that is at least about 10%, 20%, 30%, 40%, 50%, 60%, 70%, 80%, 90%, 95%, or 99%, and the sixth stream 1309 can include $C_{2+}$ compounds at a concentration that is less than about 99%, 95%, 90%, 80%, 70%, 60%, 50%, 40%, 30%, 20%, or 10%. The sixth stream 1309 can include methane at a concentration of at least about 10%, 20%, 30%, 40%, 50%, 60%, 70%, 80%, 90%, 95%, or 99%. The concentration of $C_{2+}$ compounds in the fifth stream 1308 can be higher than the concentration of $C_{2+}$ compounds in the sixth stream 1309. The sixth stream 1309 can include other species, such as Ar, $H_2$, CO, $CO_2$, $H_2O$, $N_2$, $NO_2$ and $CH_4$. At least some, all or substantially all of $CH_4$ and/or $O_2$ in the sixth stream 1309 may optionally be recycled to the OCM reactor 1301 and/or the cracking unit 1302 in a seventh stream 1310.

The at least one separation unit 1303 can include a plurality of separation units, such as at least 2, 3, 4, 5, 6, 7, 8, 9, 10, 20, 30, 40, or 50 separation units, at least some of which can be in series and/or parallel. In some examples, the at least one separation unit 1303 is a full separation train, in some cases including one or more distillation columns, scrubbers, etc. The at least one separation unit 1303 can include an olefin/alkane splitter and/or $CO_2$ separation unit. The seventh stream 1310 can include C1 (methane) recycle to the OCM reactor 1301 and/or the cracking unit 1302.

In some examples, at least about 1%, 2%, 3%, 4%, 5%, 10%, 20%, 30%, 40%, 50%, 60%, 70%, 80%, or 90% of the non-$C_{2+}$ components (e.g., $CH_4$ and/or $N_2$) of the fourth stream 1307 can be separated by the separation unit 1303 and directed along the sixth stream 1309. This can provide a fifth stream 1308 that has a higher concentration of $C_{2+}$ compounds, including olefins and higher molecular weight alkanes.

The system 1300 can include any number of OCM reactors 1301 and cracking units 1302. The system 1300 can include at least 1, 2, 3, 4, 5, 6, 7, 8, 9, or 10 OCM reactors 1301. The OCM reactors 1301 can be the same, similar or dissimilar reactors or reactor types arranged in series or parallel processing trains. The OCM reactors 1301 can be in series and/or in parallel. The system 1300 can include at least 1, 2, 3, 4, 5, 6, 7, 8, 9, or 10 cracking units 1302. The cracking units 1302 can be the same, similar or dissimilar reactors or reactor types arranged in series or parallel processing trains. The cracking units 1302 can be in series and/or in parallel. Alternatively, the reactor 1301 can be used as a cracking unit by periodically changing the feed of the reactor between OCM feed to a $C_{2+}$ alkane rich feed. In such a case, the heat capacity of a catalyst bed in the reactor 1301 can be used for alkane cracking.

The system 1300 can include at least 1, 2, 3, 4, 5, 6, 7, 8, 9, or 10 separation units. In the illustrated example, the system 1300 includes one separation unit 1303. The separation unit 1303 can be, for example, a distillation column, scrubber, or absorber. If the system 1300 includes multiple separation units 1303, the separation units 1303 can be in series and/or in parallel.

Although described for illustration of certain aspects as gas streams passing into, through and out of the reactor systems in FIG. 13, it will be appreciated that the streams 1304, 1305, 1306, 1307, 1308, 1309 and 1310 can be gaseous streams, liquid streams, or a combination of gaseous and liquid streams. In some examples, the streams 1304 and 1305 are gaseous streams, and the stream 1308 and 1309 are liquid streams.

In some examples, the separation unit 1303 can include more than two product streams. For example, olefins can be directed out of the separation unit 1303 along an olefin stream and ethane and propane can be directed out of the separation unit 1303 along another stream. The sixth stream 1309 may be dedicated to methane.

The OCM reactor 1301 can include any vessel, device, system or structure capable of converting at least a portion of the third stream 1306 into one or more $C_{2+}$ compounds using an OCM process. The OCM reactor 1301 can include an adiabatic fixed bed reactor where the combined methane/oxygen gas mixture is passed through a structured bed that can include an active temperature control component (e.g., molten salt cooling system or the like), an isothermal tubular fixed bed reactor where the combined methane/oxygen gas mixture is passed through a structured bed, an adiabatic radial fixed bed reactor where the combined methane/oxygen gas mixture is passed through a structured bed, a fluidized bed reactor where the combined methane/oxygen mixture is used to fluidize a solid catalyst bed, a honeycomb, and/or a membrane type reactor where the combined methane/oxygen mixture passes through an inorganic catalytic membrane. In some cases, a radial fixed bed reactor may be used as the heat loss in the collection volume is minimized when inward flow is used. The cracker section outer wall may be the diffuser of the OCM reactor.

The cracking unit 1302 can be a chamber or a plurality of chambers, such as a plurality of vessels or pipes. The cracking unit 1302 can include inlets for accepting compounds at various locations along the cracking unit 1302. The cracking unit 1302 can have a temperature profile across the cracking unit 1302 and along a direction of fluid flow leading from an inlet of the cracking unit 1302 to an outlet of the cracking unit 1302. In some examples, an upstream portion of the cracking unit 1302 is hotter than a downstream portion of the cracking unit 1302.

The system 1300 can include a mixer upstream of the OCM reactor 1301. The mixer can be employed for use in pre-conditioning OCM reactants, which can prevent the auto-ignition of the reactant gases prior to the OCM process in the OCM reactor 1301.

The cracking unit 1302 may be integrated into one or more unit operations of an overall OCM process system. For instance, although the OCM reactor 1301 and cracking unit 1302 are illustrated in FIG. 13 as separate unit operations, the cracking unit 1302 can be part of the OCM reactor 1301. In some cases, the cracking unit 1302 is positioned immediately adjacent to the catalyst bed within the reactor 1301, so that the $C_{2+}$ compounds may be more rapidly introduced to the cracking unit 1302 (see, e.g., FIGS. 15A and 15B). When integrating the OCM reactor 1301 with the cracking unit 1302, improved heat integration can be obtained by using a radial fixed bed reactor as illustrated in FIG. 15B.

Figure 14:
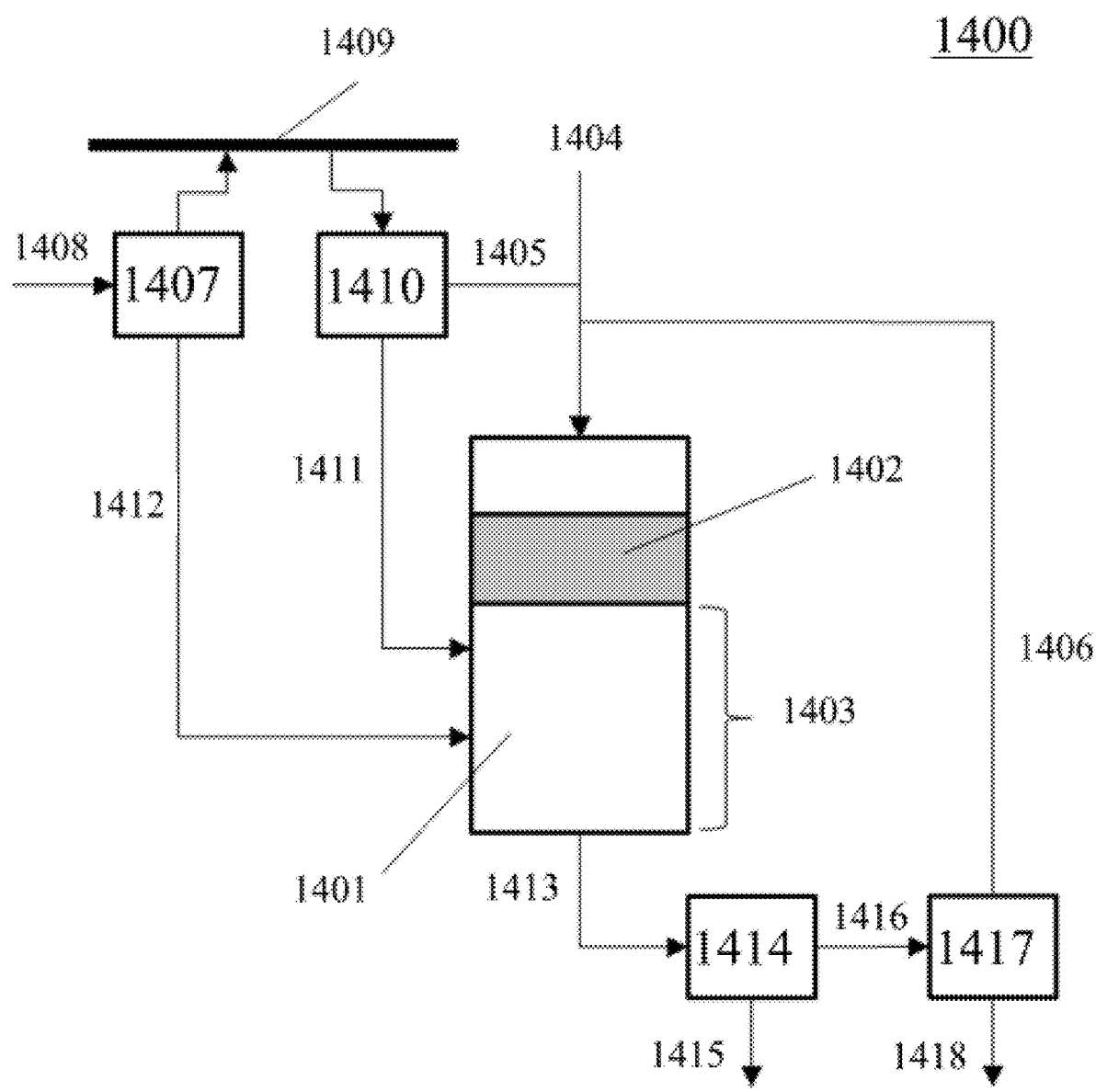
FIG. 14 shows a system comprising an OCM reactor with a catalyst unit and a cracking unit downstream of the catalyst unit.

FIG. 14 shows a system 1400 comprising an OCM reactor 1401 with a catalyst unit 1402 and a cracking unit 1403 downstream of the catalyst unit 1402. The catalyst unit 1402 can be a packed bed, for example. The system 1400 further comprises an oxidizing agent source 1404 directed into the reactor 1401. The oxidizing agent source 1404 can provide an oxidizing agent, such as $O_2$, which can be provided by way of air. Various hydrocarbon sources are directed into reactor 1401. In the illustrated example, a methane source 1405 and a hydrocarbon recycle 1406 are combined with the oxidizing agent source 1404. The methane source 1404 supplies methane and the hydrocarbon source 1405 supplies hydrocarbons, such as a portion of the $C_{2+}$ compounds generated by the OCM reactor 1401.

The cracking unit 1403 can include a heterogeneous catalyst that may be suitable for cracking alkanes to other types of hydrocarbons, such as alkenes. As an alternative, the cracking unit 1403 does not include a heterogeneous catalyst, but is configured to perform adiabatically using, for example, heat provided by steam that is generated in the OCM reaction in the catalyst unit 1402.

A natural gas plant 1407 supplies natural gas from a natural gas source 1408 to a natural gas pipeline 1409, which subsequently supplies natural gas to a separations unit 1410. The separations unit 1410 separates methane from other hydrocarbons (e.g., ethane, propane, butane, etc.) and supplies methane to the reactor 1401 in the methane source 1405. The other hydrocarbons, such as higher hydrocarbons (e.g., ethane), are supplied along stream 1411 to the reactor 1401. Other alkanes from the natural gas plant 1407 can be directed to the reactor 1401 along stream 1412.

As shown, the streams 1411 and 1412 are injected into the cracking unit 1403 at different points. As an alternative, or in addition to, the streams 1411 and 1412 can be injected into the reactor 1401 at the same point. In some situations, at least some of the streams 1411 and 1412 can be injected into the catalyst unit 1402.

In the OCM reactor 1401, methane and an oxidizing agent react to yield OCM products comprising C2+ compounds, which are directed along an OCM product stream 1413 to separations unit 1414. The separations unit 1414 separates at least a portion of the $C_{2+}$ compounds from lower molecular weight hydrocarbons (e.g., methane) and/or non-$C_{2+}$ impurities in the OCM product stream 1413. A $C_{2+}$ compound product stream 1415 is directed from the separations unit 1414 for downstream use, such as non-OCM processes or storage. Lower molecular weight hydrocarbons, such as methane, are directed along stream 1416 to a storage unit 1417, which can subsequently direct the lower molecular weight hydrocarbons to the reactor 1401 along the hydrocarbon recycle stream 1406. At least a portion of the lower molecular weight hydrocarbons can be purged from the storage unit 1417 via a purge 1418

In some instances, in the OCM reactor 1401 at least a portion of the methane can react with an oxidizing agent (e.g., oxygen) in the presence of the one or more catalysts to provide an OCM product stream comprising one or more $C_{2+}$ compounds, including at least ethane and ethylene. The hydrogen liberated during the conversion of methane to the one or more $C_{2+}$ compounds can combine with the oxygen to form water. Any oxygen present also can combine with at least a portion of the carbon present in the methane to form carbon dioxide. The overall conversion of methane and oxygen to one or more $C_{2+}$ compounds can be dependent upon at least catalyst composition, reactant concentration, and reaction temperature and pressure within the OCM reactor 1401, the thermal profile through the one or more catalysts in the OCM reactor 1401, the maximum temperature within the one or more catalysts, the maximum temperature rise within the one or more catalysts, or combinations thereof.

In addition to the one or more $C_{2+}$ compounds, the OCM product stream generated in the OCM reactor 1401 may also contain residual un-reacted methane, residual un-reacted oxygen, water, and carbon dioxide. Ethane can also be present in OCM product stream. The ethane concentration within the OCM product stream can be at least about 0.25 mol %; at least about 0.5 mol %; at least about 0.75 mol %; at least about 1 mol %; at least about 1.5 mol %; at least about 2 mol %; at least about 2.5 mol %; at least about 3 mol %; at least about 3.5 mol %; at least about 4 mol %; at least about 4.5 mol %; or at least about 5 mol %. Ethylene will also be present in the OCM product stream. The ethylene concentration within the OCM product stream can be at least about 0.25 mol %; at least about 0.5 mol %; at least about 0.75 mol %; at least about 1 mol %; at least about 1.5 mol %; at least about 2 mol %; at least about 2.5 mol %; at least about 3 mol %; at least about 3.5 mol %; at least about 4 mol %; at least about 4.5 mol %; or at least about 5 mol %.

The conversion of methane to higher molecular weight hydrocarbons, such as ethane and ethylene, can be dependent upon the residence time of reactants such as methane, ethane, and higher hydrocarbons in the OCM reactor 1401. In particular, the ratio of ethane to ethylene can be dependent upon the residence time of reactants, such as methane, ethane, and higher hydrocarbons in the OCM reactor 1401 at temperatures in excess of about 800° C. Experience has shown that the formation of ethylene within the OCM reactor 1401 may occur as a secondary reaction that may rely upon a steam or thermal cracking process rather than an oxidative process. Thus, the conversion of ethane to ethylene may occur at the elevated temperatures of the OCM reaction, either in portions of the OCM reactor 1401 or immediately following the OCM reactor 1401 where the oxidant concentration is reduced.

In some cases, at least a portion of the ethane present in the OCM product stream can be separated and recycled back into the OCM reactor 1401 in order to convert that ethane to ethylene. In some embodiments, at least a portion of the ethane is separated from the OCM product stream, e.g., by passing the OCM product stream or a portion thereof through a downstream or post-production cryogenic separation process. See, for example, U.S. patent application Ser. No. 13/739,954, filed Jan. 11, 2013, which is entirely incorporated herein by reference for all purposes. In some instances, at least a portion of the separated ethane may be re-injected directly into the OCM reactor 1401 at one or more points along the OCM reactor 1401, including within the catalyst unit, the cracking unit 1403, or both. The location of injection or re-injection can be selected to effect a given product distribution out of the OCM reactor 1401, such as a higher proportion of alkenes as compared to alkanes.

In some cases, ethane or other alkanes are injected into the OCM product stream at a location in, at, or in proximity to the OCM reactor 1401. This can advantageously enable the use of process conditions to crack alkanes to alkenes, such as ethane to ethylene. In some examples, alkanes are cracked with the aid of steam. While this cracking of an alkane to alkene (e.g., ethane to ethylene) can also be achieved by injecting the alkane at an earlier stage, the prolonged exposure to the elevated temperature may detrimentally result in greater combustion of the alkane to alkene through the OCM reactor 1401. The alkane can be provided as recycle from the OCM product stream comprising $C_{2+}$ products produced by the OCM reactor 1401. As an alternative, or in addition to, the alkane can be provided from an exogenous source, such as, for example, an ethane output from a natural gas liquids (NGL) processing facility, or the like.

One or more higher hydrocarbons can be combined with the OCM product stream prior to cooling the OCM product stream. In some embodiments, one or more higher hydrocarbons can be introduced to a catalyst unit 1402 or the cracking unit 1403 in the OCM reactor 1401. To reduce the likelihood of forming undesirable byproducts, the oxygen concentration in the OCM product stream at the point of combination with the one or more higher hydrocarbons can be less than about 5 mole %, less than about 2 mol %, less than about 1 mol %, less than 0.5 mol %, or less than 0.1 mol %. To improve the yield of desirable higher hydrocarbon products (e.g., alkenes), the temperature of the OCM product stream at the point of combination with the one or more higher hydrocarbons can be greater than about 600° C.; greater than about 650° C.; greater than about 700° C., greater than about 750° C.; greater than about 800° C.; greater than about 850° C.; greater than about 900° C., or greater than about 920° C. In some embodiments, the temperature of the higher hydrocarbons may be increased prior to combination with the OCM product stream or introduction to the OCM reactor 1401 to minimize the cooling effect of the higher hydrocarbons on the OCM gas. In some embodiments, prior to combining with the OCM product stream or being introduced to the OCM reactor 1401, the temperature of the higher hydrocarbons can be increased to a temperature less than about 750° C.; less than about 700° C.; less than about 650° C.; or less than about 600° C.

In some cases, significant cracking of an alkane to an alkene (e.g., ethane to ethylene) can occur when the alkane is introduced within the catalyst bed of the OCM reactor 1401. At the same time the amount of selectivity of the OCM reaction can be only slightly affected by the addition of up to 20 mol % alkane (e.g., ethane, or propane, or butane) into the OCM product stream generated in the catalyst unit 1402. See, e.g., U.S. patent application Ser. No. 13/900,898, filed May 23, 2013, which is entirely incorporated herein by reference for all purposes.

Ethane or one or more higher hydrocarbons (e.g., alkanes) may be introduced at any point in the OCM reactor 1401, including at one or more points in the streams 1405 or 1406, the catalyst unit 1402, and/or the cracking unit 1403. In some embodiments, ethane may be preferentially introduced at locations in the OCM reactor 1401 where the concentration of the oxidizing agent is reduced to lessen the formation of undesirable reaction byproducts, such as coke and similar long chain combustion byproducts. The ethane or one or more higher hydrocarbons may be introduced to the catalyst unit 1402 using one or more distributors fabricated from one or more non-reactive materials, for instance a ceramic oxide coated high temperature compatible metal or metal alloy such as Inconel, Hastelloy, and Alloy N155 and the like. In at least some implementations the one or more distributors may include a thermal control system to limit the temperature of the distributor and thereby lessen the likelihood of occurrence of premature cracking of the ethane or the one or more higher hydrocarbons prior to the introduction of the ethane or one or more higher hydrocarbons to the OCM reactor 1401.

In at least some embodiments, one or more higher hydrocarbons, for instance recovered ethane or $C_1$-$C_4$ light ends captured in an ethylene to liquids separations process subsequent to the OCM reactor 1401, may be introduced to the OCM reactor 1401, at a point before the OCM reactor 1401 (e.g., by mixing with the methane source 1405), or after the OCM reactor 1401 (e.g., by mixing with the OCM gas). In some embodiments, at least a portion of the one or more higher hydrocarbons may be introduced directly within the catalyst unit 1402. Alternatively, or in addition to, at least a portion of the one or more higher hydrocarbons may be introduced to the OCM gas prior to cooling the OCM gas in a thermal transfer device fluidly coupled to the OCM reactor 1401. For instance, at least a portion of the one or more higher hydrocarbons can be introduced directly to the cracking unit 1403.

Figure 15A:
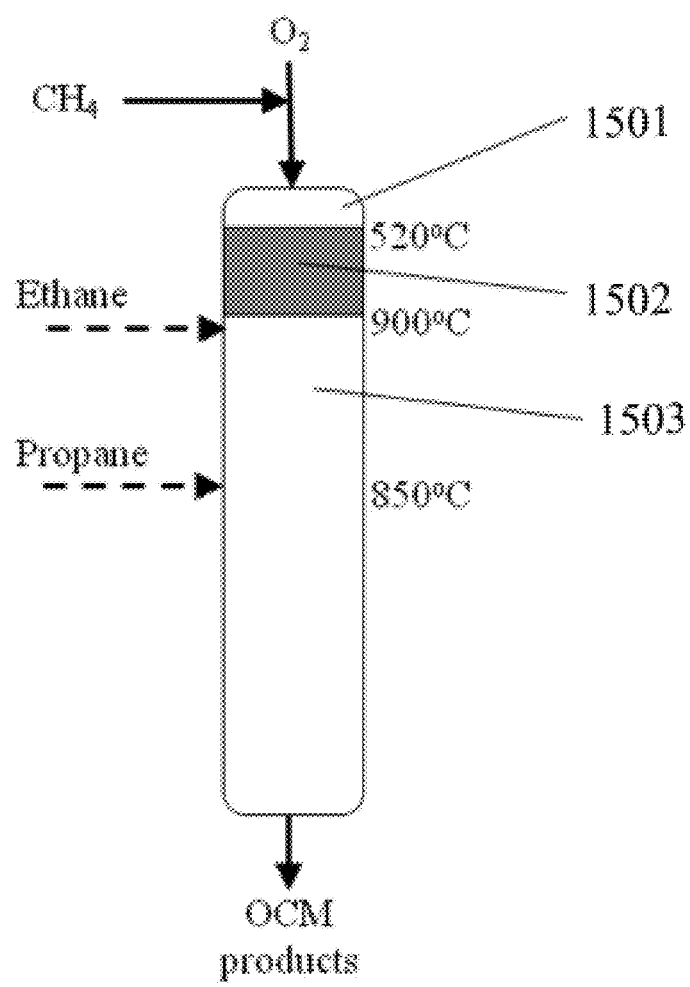
FIG. 15A shows an OCM reactor comprising an integrated catalyst unit and cracking unit.
Figure 15B:
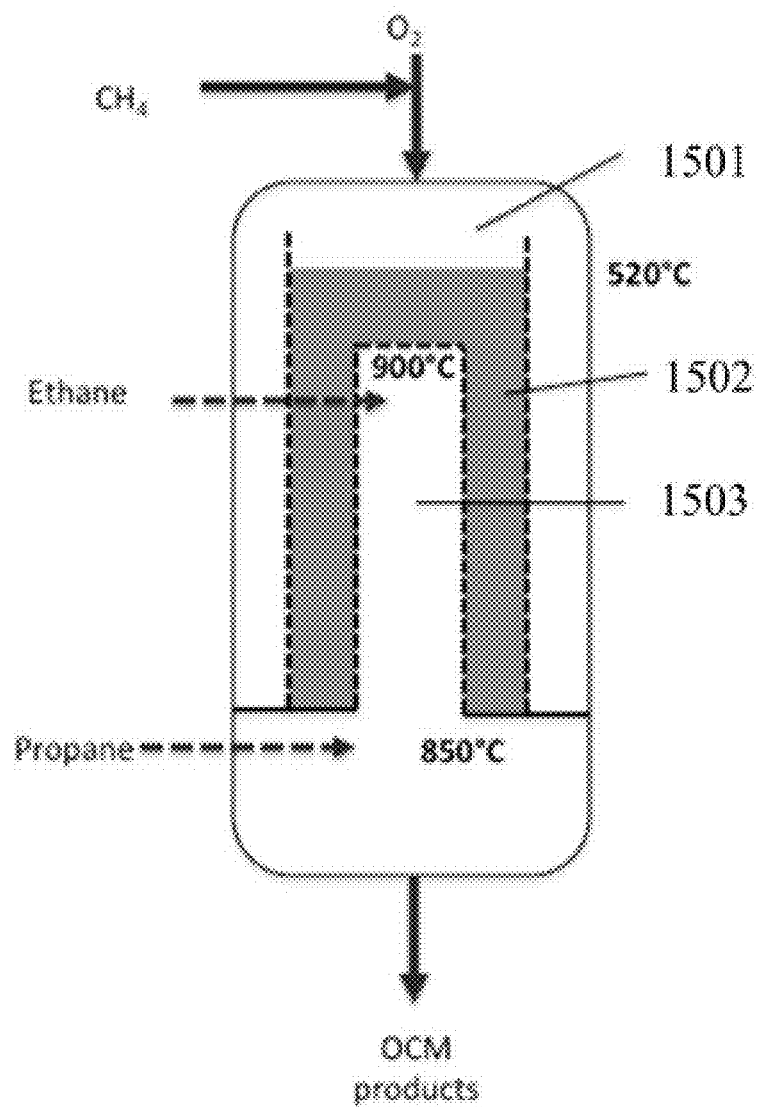
FIG. 15B shows an OCM reactor comprising a radial fixed bed catalyst unit.

FIG. 15A shows an OCM reactor 1501 comprising a catalyst unit 1502 and a cracking unit 1503. The catalyst unit 1502 can be, for example, a packed bed reactor comprising a heterogeneous catalyst. The catalyst unit 1502 can be configured to perform an OCM process using natural gas and $O_2$ inputted into the reactor 1501. The cracking unit 1503 is configured to perform crack alkanes (e.g., ethane) to other types of hydrocarbons, such as alkenes (e.g., ethylene). The cracking unit 1503 can be configured to operate adiabatically using heat liberated in the catalyst unit 1502 in the OCM process, which heat can be conveyed by way of steam generated in the OCM process, for example.

Various reactor types may be employed for use as the OCM reactor 1501. In some examples, the OCM reactor 1501 is a fixed bed reactor, fluidized bed reactor, tubular isothermal reactor or a combination thereof. A fixed bed reactor can be an adiabatic fixed bed reactor. In some examples the OCM reactor 1501 comprises multiple reactors in series. In some cases, the OCM reactor 1501 can be operated at elevated pressures, such as between 1.5-50 bars (absolute), or 2-20 bars (absolute). In some situations, the catalyst unit 1502 can include catalyst particles in the form of nanostructures (e.g., nanowires).

In some cases, steam formed in the OCM process in the catalyst unit 1502 can aid in lowering the partial pressure of alkanes in an OCM product stream, thereby preventing and/or reducing the potential for carbon coking or deposition in the cracking unit. In some situations, in order to minimize OCM product destruction, such as via combustion or carbon coking/deposition, higher chain or molecular weight hydrocarbons can be injected in an oxygen-depleted region of the OCM reactor 1501, such as in the cracking unit 1503. Steam generated in the catalyst unit 1502 can be directed to the cracking unit 1503 at various points along the cracking unit 1503.

During use, the catalyst unit 1502 can have an average temperature between about 450° C. and 1200° C., or 500° C. and 1000° C. The catalyst unit 1502 can have an inlet with an inlet temperature and an outlet with an outlet temperature. During use, the inlet temperature can be less than the outlet temperature. A temperature gradient may exist across the catalyst unit 1502 along a direction of fluid flow (i.e., from inlet to outlet). In an example, during use an inlet of the catalyst unit 1502 is at a temperature of about 520° C. and an outlet of the catalyst unit 1502 is at a temperature of about 900° C. In some examples, the inlet can have a temperature that is less than or equal to about 750° C., 730° C., 710° C., 700° C., 690° C., 670° C., 650° C., 630° C., 610° C., 600° C., 590° C., 570° C., 550° C., 520° C., 510° C., 490° C., 470° C., or 450° C. The outlet may have a temperature that is less than or equal to about 850° C., 860° C., 870° C., 880° C., 890° C., 900° C., 910° C., 920° C., 930° C., 940° C. or 950° C. The outlet temperature can be greater than the inlet temperature. The catalyst unit 1502 can be part of a multistage unit comprising the cracking unit 1503 as the last stage. Cooling of the OCM products may occur in the cracking unit 1503.

The cracking unit 1503 can be used to form a given type or distribution of hydrocarbons. In some embodiments, the cracking unit 1503 can be used to generate an OCM product stream with a higher proportion of alkene products as compared to alkane products, such as a greater proportion of ethylene as compared to ethane. Various properties of the OCM reactor 1501, including operating conditions, can be selected to increase alkene to alkane ratios in OCM product streams. The operating conditions can include, without limitation, product recycle (e.g., $CH_4$ recycle), the catalyst used in the catalyst unit 1502, the size and shape of the OCM reactor 1501, the size and shape of the cracking unit 1503, OCM reactor temperature, the temperature or temperature distribution in the cracking unit 1503, and stream (e.g., hydrocarbon-containing stream) residence time in the cracking unit 1503. In some embodiments, the stream residence time (e.g., post-bed residence time) and cracking unit temperature are controlled to yield a given product distribution. One or more operating conditions of the OCM reactor 1501, including the cracking unit 1503, can be selected such that a molar ratio of $C_{2+}$ alkene to $C_{2+}$ alkane in a product stream out of the OCM reactor 1501 is greater than or equal to about 0.1, 0.2, 0.3, 0.5, 0.6, 0.8, 1, 2, 3, 4, 5, 6, 7, 8, 9, 10, 12, 14, 16, 18, 20, 30, 40, 50, 60, 70, 80, 90, 100, or greater. In some cases, the molar ratio of $C_{2+}$ alkene to $C_{2+}$ alkane is limited by thermodynamic equilibrium, which can be about 6 when water is present at 6% and $H_2$ is present at 2%.

Stream residence time in the cracking unit 1503 can be controlled by regulating the flow rate of oxygen (or other oxidizing agent) and/or methane into the OCM reactor 1501 or the flow rate of OCM products out of the OCM reactor 1501. The flow rate can be regulated with the aid of valves and fluid flow system (e.g., pumps) that can be under the control of a computer system programmed to regulate process parameters, as described elsewhere herein.

In the cracking unit 1503, the high heat capacity of OCM products generated in the catalyst unit 1502 can be used to drive the endothermic cracking of alkanes to alkenes or other types of hydrocarbons (e.g., alkynes). Moreover, the thermal heat capacity of the OCM effluent may be substantially high such that it can be used to further convert additional alkanes (e.g., ethane and propane) to alkenes—more than what is present in OCM effluent—to alkenes (e.g., ethylene and propylene) in the cracking unit 1503 of the OCM reactor 1501.

In some examples, ethylene/ethane ratios can increase with increasing OCM reactor 1501 size. For example, the ethylene to ethane ratios in the OCM product stream can increase in going from 4 millimeters (mm) to 8 mm to 2 inch OCM reactors. In some situations, radial reactors may be used to shield the cracking section from cooler reactor walls. Generally, the increasing $C_{2+}$ alkene to alkane ratio may be a reflection of the increasing adiabaticity the cracking reaction, which may be the result of increasing diameter or cross-sectional size of the reactor 1501. Higher adiabaticity can lead to higher reactor temperatures, which can assist in thermal cracking of paraffins (ethane, propane, etc.) in the cracking unit 1503, leading to increasing olefins output from the OCM reactor 1501.

The cracking unit 1503 can have various sizes and configurations. In some cases, the cracking unit 1503 includes one or more tubes each comprising a fluid flow path leading form an inlet to an outlet of a tube. A residence time of a hydrocarbon stream directed through the cracking unit 1503 can be a function the size of the cracking unit 1503. In some examples, the cracking unit 1503 has a cross-section size (e.g., diameter) of at least about 1 inch, 2 inches, 3 inches, 4 inches, 5 inches, 6 inches, 12 inches, 16 inches, 24 inches, 36 inches, 48 inches, 60 inches, 6 feet, 7 feet, 8 feet, 9 feet, 10 feet, 11 feet, 12 feet, 13 feet, 14 feet, 15 feet, 20 feet, 30 feet or more. The residence time of the OCM product gas in the cracking unit 1503 can be less than or equal to about 2000 milliseconds (ms), 1000 ms, 500 ms, 400 ms, 300 ms, 200 ms, 100 ms, 50 ms, or 10 ms Olefins yield can be improved by addition of external alkanes (e.g., ethane and/or propane) to the catalyst unit 1502, the cracking unit 1503, or both. Natural gas can be the source of ethane, propane, butanes, and other hydrocarbons used to increase olefins yield. Process variables such residence time (e.g., residence time in the cracking unit 1503) and inlet temperature can be used to control OCM product distribution. As an alternative, or in addition to, alkanes can be provided to the cracking unit 1503 as recycle from the OCM products generated in the OCM reactor.

In some embodiments, optimum performance may be achieved by using OCM product residence times in the cracking unit 1503 that are less than about 2000 milliseconds (ms), 1000 ms, 500 ms, 400 ms, 300 ms, 200 ms, 100 ms, 50 ms, or 10 ms, at a cracking unit 1503 temperature from about 800° C. and 950° C., or 810° C. to 900° C. In some cases, the cracking unit 1503 has an inlet temperature (at a location adjacent to the catalyst unit 1502) that is from about 850° C. to 1000° C., or from about 880° C. to 950° C., and an outlet temperature that is from about 750° C. to 850° C., or about 780° C. to 820° C.

In some example, ethane is injected into the cracking unit 1503 at a temperature that is less than or equal to about 850° C., 860° C., 870° C., 880° C., 890° C., 900° C., 910° C., 920° C., 930° C., 940° C. or 950° C. In some cases, this temperature is an outlet temperature of the catalyst unit 1502. Propane is injected into the cracking unit 1503 at a temperature that is less than the temperature at which ethane is introduced into the cracking unit. In some cases, propane is introduced to the cracking unit 1503 at a temperature that is less than or equal to about of 700° C., 710° C., 720° C., 730° C., 740° C., 750° C., 760° C., 770° C., 780° C., 790° C. or 800° C. Butane can be injected into the cracking unit 1503 at a temperature that is less than the temperature at which propane is injected into the cracking unit 1503. In some cases, butane is introduced to the cracking unit 1503 at a temperature that is less than or equal to about of 600° C., 610° C., 620° C., 630° C., 640° C., 650° C., 660° C., 670° C., 680° C., 690° C. or 700° C. Propane can be injected into the cracking unit 1503 at a location that is downstream from the location at which ethane is injected into the cracking unit 1503. Butane (or other higher molecular weight alkanes) can be injected into the cracking unit 1503 at a location that is downstream from the location at which propane is injected into the cracking unit 1503.

In some examples, alkene yield from the OCM reactor 1501 is optimized by selecting an OCM product residence time from about 100 ms and 500 ms. By carefully controlling the residence times (e.g., less than 500 ms) and temperature profile in the cracking unit 1503, the proportion of undesirable $C_{2+}$ products (e.g., ethane) as compared to desirable $C_{2+}$ products (e.g., ethylene) in the OCM product stream may be reduced. In some cases, to minimize OCM product destruction, higher molecular weight hydrocarbons may be injected in the oxygen-depleted region of the OCM reactor 1501, such as the cracking unit 1503. In some situations, an increase in alkene yield can be advantageously realized with minimal increase in capital expenditure, which can enable the formation of desirable alkene products in the OCM product stream with little or no increase in operating cost.

Alkane cracking in the cracking unit 1503 can also lead to a higher concentration of hydrogen in the OCM product stream out of the OCM reactor 1501. The effective carbon efficiency in an OCM process can be significantly increased by methanation of CO and $CO_2$ with $H_2$, e.g., $CO_2 + 2 H_2 \rightarrow CH_4 + 2 H_2O$. Methane can be recycled back to OCM. In an example, any hydrogen formed in the OCM reactor via alkane cracking in the cracking unit 1503 may be converted to methane via reaction with CO or $CO_2$, and the methane can be separated in a separation unit downstream of the OCM reactor 1501 and recycled to the OCM reactor 1501 (e.g., via hydrocarbon recycle 1406 of FIG. 14). Such methanation can take place in a diluted stream with no pre-separation of the CO and $H_2$ from the methane. This can advantageously reduce the need to clean up the recycle stream in cases in which pure or substantially pure $O_2$ is used.

Process parameters may be controlled to effect a given product distribution. Because of higher reactivity, hydrocarbon cracking severity can increases with increasing carbon number of the hydrocarbon. For instance, the cracking severity of propane is higher than the cracking severity of ethane at a given inlet temperature of the cracking unit 1503. In some situations, the temperature of the cracking unit 1503 can be lowered with increasing carbon number to increase the olefin yield and selectivity. The temperature can be regulated (i.e., maintained, lowered or increased) with the aid of a computer system that is programmed to regulate properties of the OCM reactor 1501.

Alkane cracking in the OCM reactor 1501 to form other hydrocarbons, such as alkenes, may be sequential. In some cases, alkane cracking is commenced with ethane followed by propane and other higher hydrocarbons. For example, with the cracking unit 1503 at 900° C., ethane is injected into the cracking unit 1503, which can decrease the temperature of the cracking unit 1503. Once the temperature of the cracking unit 1503 has decreased to below 800° C., for example, propane can be injected into the cracking unit 1503. In some cases, once the temperature of the cracking unit 1503 has decreased to a temperature at or below 700° C., butane can be injected into the cracking unit 1503. A mixed alkane stream can be injected at a point in the cracking unit 1503 at a stream temperature that is less than or equal to about 900° C., 850° C., 800° C., 750° C., 700° C., 650° C. or 600° C.

As an alternative, or in addition to, alkanes can be injected into the cracking unit 1503 at locations that are selected to have a temperature that is suitable for a given alkane. For example, ethane cracking may be optimum at 900° C. and propane cracking may be optimum at 850° C. Ethane can be injected into the cracking unit 1503 at a location that is closer to the catalyst unit 1502 and propane can be injected into the cracking unit 1503 at a location that is further away from the catalyst unit 1502, as shown in FIG. 15A.

The temperature at various locations across the OCM reactor 1501, including the cracking unit 1503 can be detected using temperature sensors and relayed to a computer system. The computer system can then determine the appropriate hydrocarbon to inject into the cracking unit 1503 at a measured temperature. For example, if the measured temperature is 900° C., the computer system can direct the flow of ethane into the cracking unit 1503. In some cases, ethane is directed into the cracking unit 1503 from an external source, such as a natural gas source. Ethane can be selected over other hydrocarbon in the natural gas source using a separation unit (e.g., separation unit 1410 of FIG. 14).

The catalyst unit 1502, the cracking unit 1503, or both can be integrated with a heat exchanger that is configured to remove heat from, or direct heat to, a respective unit. In an example, an integrated heat exchanger is configured to remove heat from the catalyst unit 1502 during the OCM process and direct the removed heat to the cracking unit 1503.

FIG. 15B shows the OCM reactor 1501 in a radial fixed bed configuration. At least a portion of the cracking unit 1503 is circumscribed by at least a portion of the catalyst unit 1502. Ethane can be injected into the cracking unit 1503 at a location upstream of the point at which propane is injected into the cracking unit 1503. In the illustrated example, ethane is injected into the cracking unit 1503 at a temperature of about 900° C., and propane is injected into the cracking unit 1503 at a temperature of about 850° C. The locations (and temperatures) at which external alkanes are injected into the cracking unit 1503 can be selected to effect a given product distribution and conversion.

Figure 16:
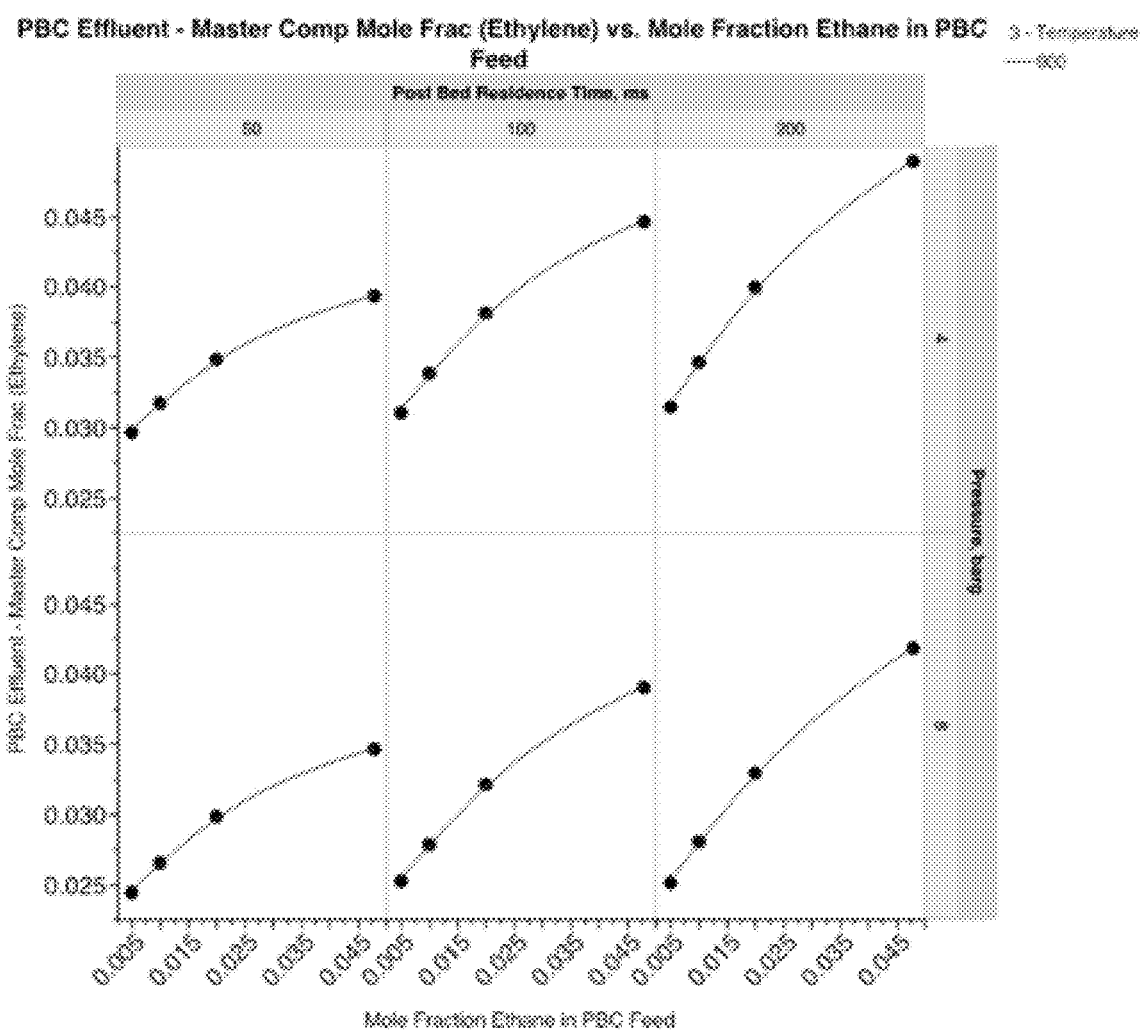
FIG. 16 shows a plot of a thermodynamic and kinetic modeling study showing the mole fraction of ethylene as a function of the mole fraction of ethane at various residence times (50 ms, 100 ms and 200 ms)
Figure 17:
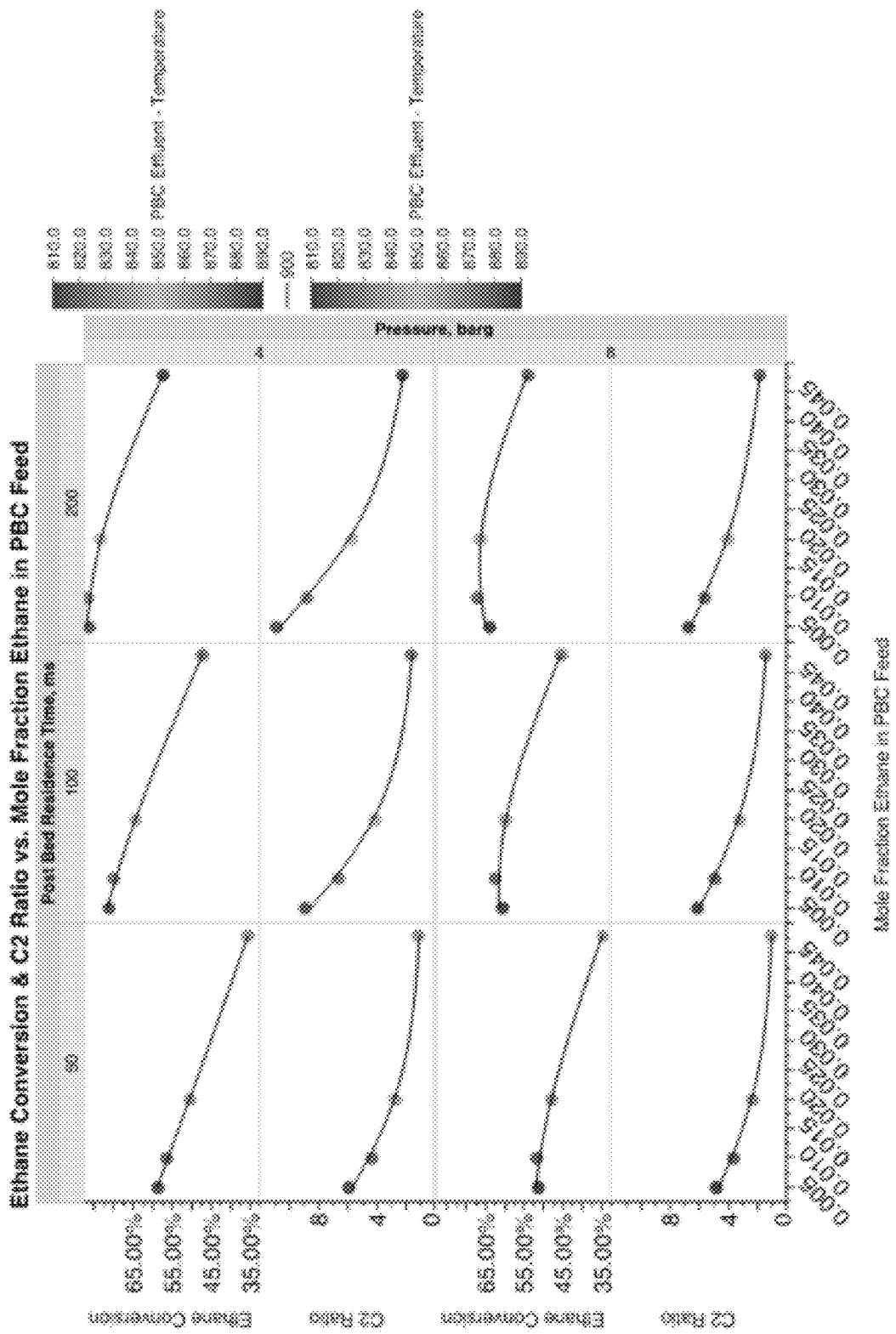
FIG. 17 shows a plot of a thermodynamic and kinetic modeling study showing ethane conversion and $C_2$ ratio as a function of mole fraction of ethane at various residence times (50 ms, 100 ms and 200 ms)

Thermodynamic and kinetic modeling studies of the adiabatic cracking post OCM catalyst bed (see FIGS. 16 and 17) indicate that the alkene yield may be increased using OCM reactors with cracking units, such as post-bed reactor units. In some cases, the ethylene yield in an OCM reactor can be increased by at least a factor of two using OCM reactors with post-reactor cracking units, as described above. For example, at a pressure of about 8 bar (gauge), the percentage of ethylene exiting OCM-assisted cracking section can be as high as about 3.5%, 4.5%, 5.5%, 6.5%, 7.5%, or more with an injection of about 4%, 5%, 6%, 7%, 8%, or more ethane into the cracking unit 1503. FIG. 16 shows the mole fraction of ethylene as a function of the mole fraction of ethane at various residence times (50 ms, 100 ms and 200 ms), and FIG. 17 shows ethane conversion and C2 ratio as a function of mole fraction of ethane at various residence times (50 ms, 100 ms and 200 ms).

Various approaches can be employed to introduce alkanes to an OCM reactor integrated with a cracking unit. FIGS. 18A-18D show various approaches that may be employed. These figures show an OCM reactor comprising an OCM catalyst unit with a downstream cracking unit, and various examples of ethane and propane injection locations. The catalyst unit can include a catalyst bed. A hydrocarbon feed ("HC feed") directs a hydrocarbon (e.g., methane) to the OCM reactor, and an air/$O_2$ stream directs air/$O_2$ to the OCM reactor. The hydrocarbon and air/$O_2$ streams can be directed to a pre-conditioning unit of the OCM reactor, such as a mixer. Ethane and propane can be provided from an external source, such as an NGL processing facility and/or as recycle from an OCM product stream. The hydrocarbon, air/$O_2$, ethane and propane streams can be directed to heat exchangers to preheat the streams prior to introduction to the OCM reactor. In the figures, lengths $L_1$, $L_2$ and $L_3$ can be selected to optimize ethane and propane cracking to desired or otherwise predetermined products, which can be a function of gas temperature and residence time. The ethane injection location is upstream of the propane injection location.

During use, the hydrocarbon and air/$O_2$ directed into the OCM reactor react to form OCM products that are directed along a hydrocarbon-containing stream to the cracking unit and out of the OCM reactor. In the cracking unit, any alkanes in the hydrocarbon-containing stream, including alkanes introduced to the catalyst unit and/or cracking unit from an external source and any alkanes formed in the catalyst unit, can be cracked to alkenes and directed out of the OCM reactor along the hydrocarbon-containing stream.

Figure 18A:
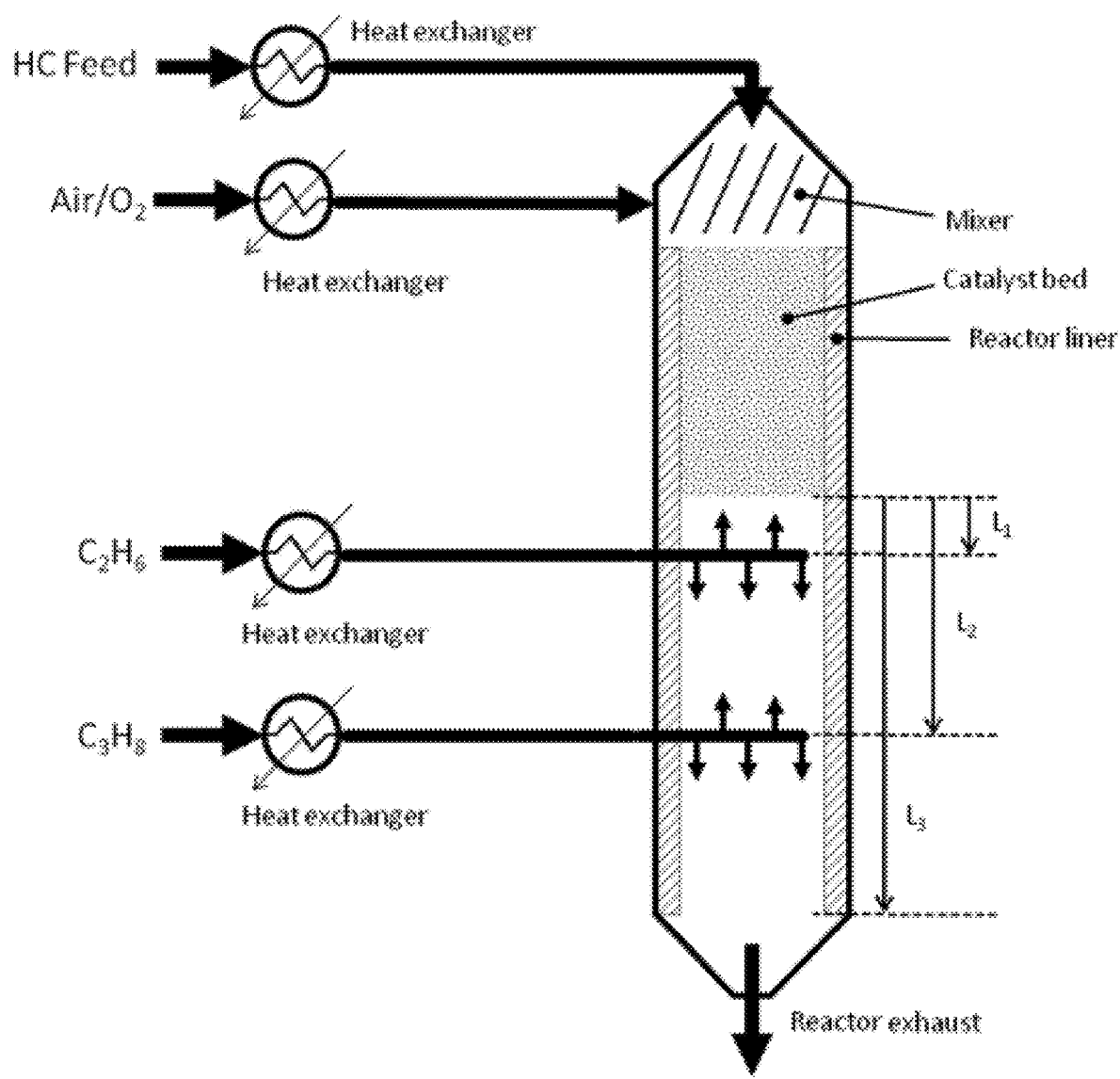
FIGS. 18A-18D show schematically illustrated various OCM reactors with alkane injections lines for introducing alkanes to the OCM reactors.
Figure 18B:
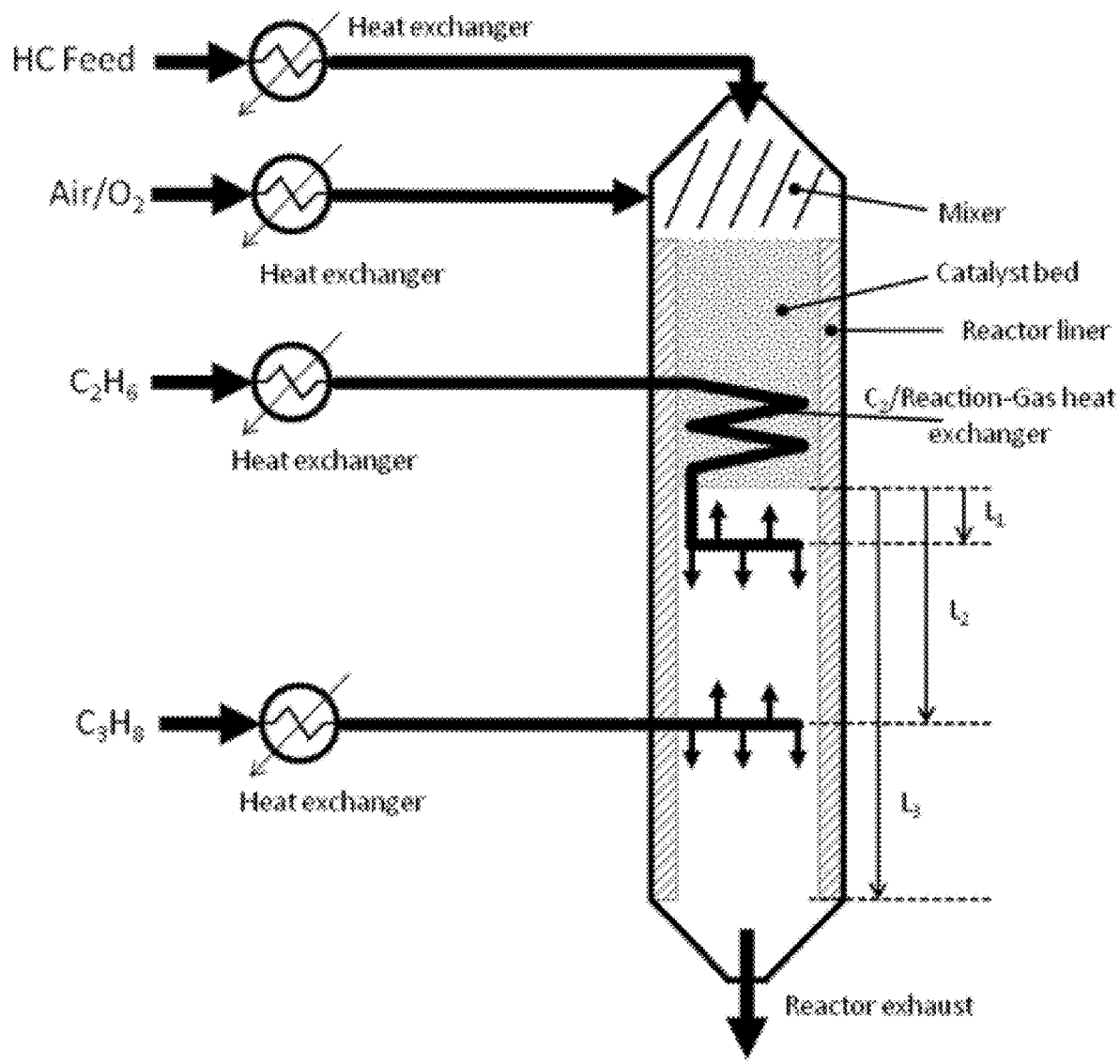
Figure 18C:
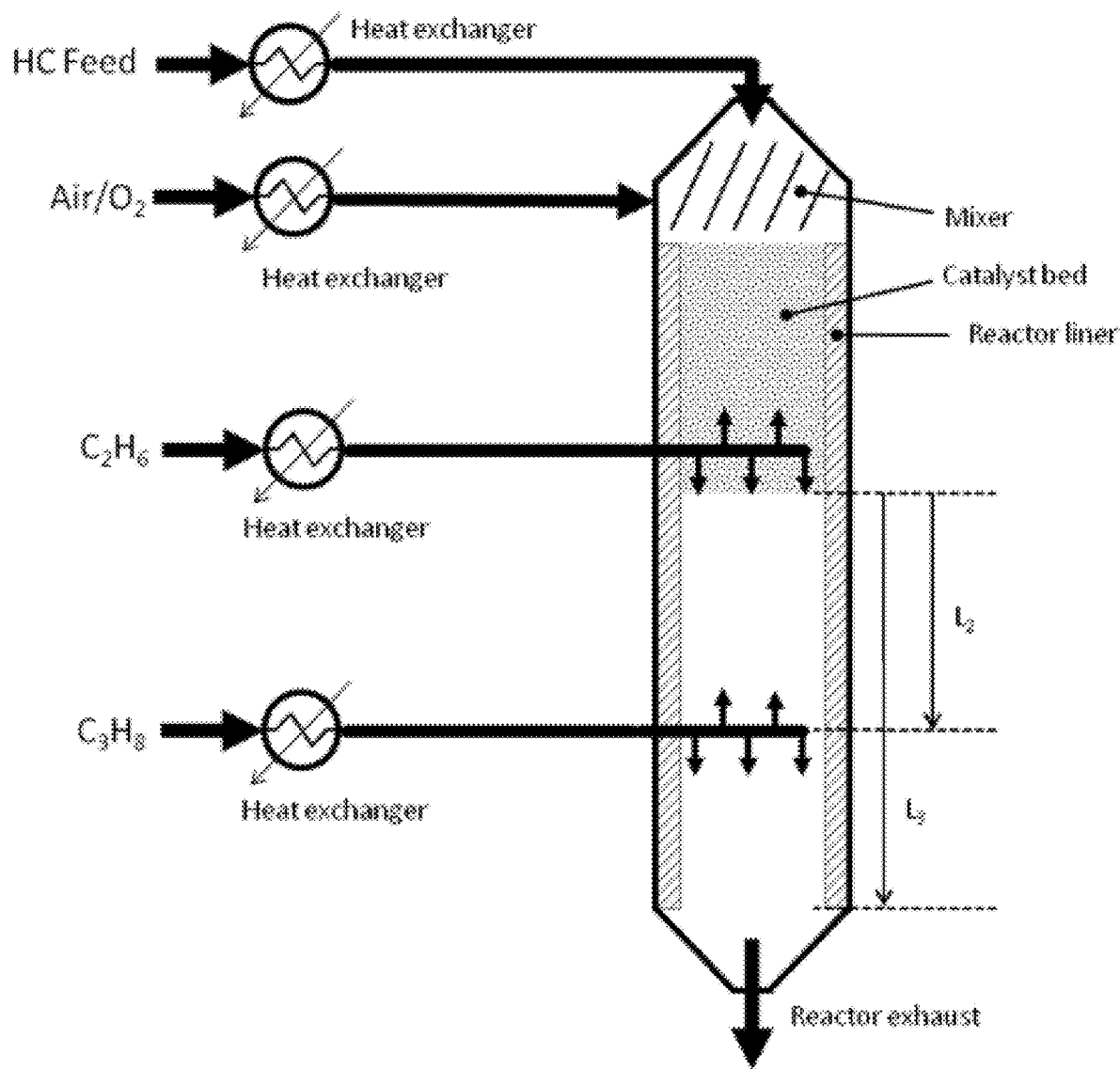
Figure 18D:
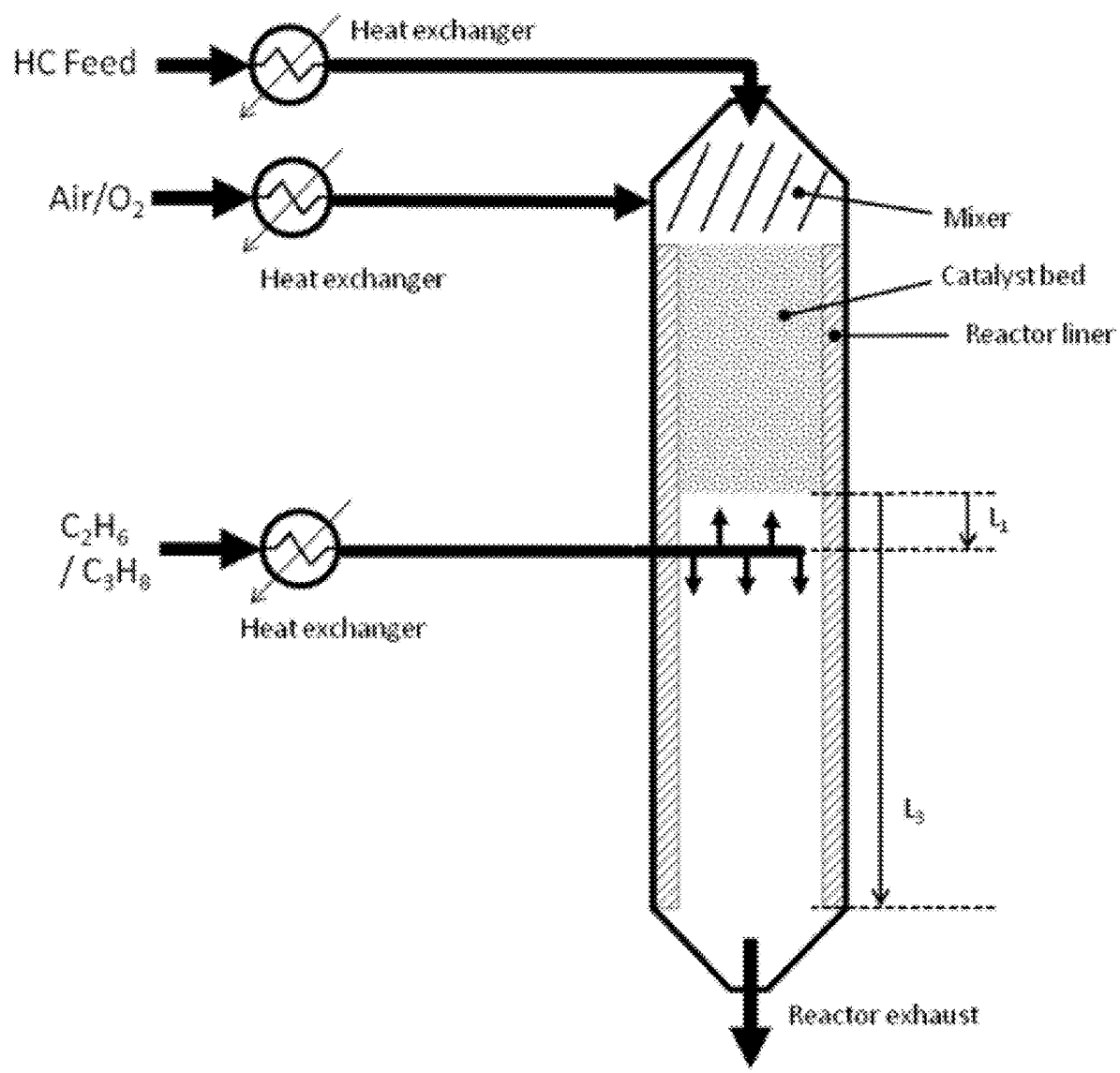

In FIG. 18A, separate ethane and propane injection locations introduce ethane and propane to the cracking unit. In FIG. 18B, integral heat exchange is employed to remove heat from catalyst unit and to heat the ethane stream prior to introduction of the ethane stream into the cracking unit. As an alternative, ethane can be injected into the bottom of the catalyst unit, as shown in FIG. 18C. In FIG. 18D, ethane and propane are injected at the same location (or co-injected).

An aspect of the present disclosure provides mixers and methods of mixing compounds (e.g., ethane and propane) into the cracking unit. Operation of the OCM process with ethane added to the cracking unit can benefit from conditions whereby; (a) ethane is injected into and uniformly mixed with the OCM exhaust gas, and (b) the mixed gases are provided sufficient residence time for conversion prior to thermal quenching. Thermal quenching can halt reactions that yield undesirable hydrocarbon constituents at the expense of ethylene. The mixing of ethane and OCM exhaust gas can be accomplished in a process that is rapid and results in a uniformly blended mixture.

In some cases, high ethylene yields are obtained by providing for residence times between ethane injection and thermal quenching of at least about 5 milliseconds (ms), at least about 10 ms, at least about 20 ms, at least about 30 ms, at least about 40 ms, at least about 50 ms, at least about 60 ms, at least about 70 ms, at least about 80 ms, at least about 100 ms, at least about 120 ms, at least about 140 ms, at least about 160 ms, at least about 180 ms, at least about 200 ms, at least about 300 ms, or at least about 400 ms. In some cases, the residence time is at most about 5 ms, at most about 10 ms, at most about 20 ms, at most about 30 ms, at most about 40 ms, at most about 50 ms, at most about 60 ms, at most about 70 ms, at most about 80 ms, at most about 100 ms, at most about 120 ms, at most about 140 ms, at most about 160 ms, at most about 180 ms, at most about 200 ms, at most about 300 ms, or at most about 400 ms. In some cases, the residence time is between about 10 ms and 100 ms, between about 30 ms and about 80 ms, or between about 50 ms and about 60 ms.

In some embodiments, the alkane (e.g., ethane or propane) is mixed with the OCM exhaust gas uniformly before exiting the mixer, upon exiting the mixer, or prior to initiation of a cracking reaction. The alkane and OCM exhaust gas can be mixed such that the mixed gas has variations in temperature, alkane concentration, or flow rate that do not deviate more than about 1%, 3%, 5%, 10%, 15%, 20%, 25%, 30%, 50%, 60%, or 80% from the average temperature, alkane concentration, or flow rate.

The mixers and mixing processes described herein can result in broad spectrums of mixture ratios. In one embodiment of the mixer, the OCM exhaust gas enters the system at a large end of a converging section in an axial direction. Ethane is injected into the converging section through a plurality of ports that can be directed to produce ethane jets having axial, radial and tangential velocity components. The ports can be substantially directed in tangential and radial directions. The converging section can be connected to a duct of smaller diameter (e.g., the reactor). The geometry of the converging and reactor sections (diameters and lengths) can be selected to provide the desired residence times for reactions to occur. In some cases, a heat exchanger is located downstream of and connected to the reactor, which can be utilized to thermally quench the gas stream. The mixer can be made out of materials that can withstand high temperatures (e.g., about 800 C to 1000 C, which can be the temperature of the OCM exhaust gas). Examples of suitable materials are ceramics such as alumina.

Post-Bed Cracking

An aspect of the present disclosure provides OCM systems and methods for increasing the concentration of alkenes (or olefins) in $C_{2+}$ compounds outputted from an OCM reactor. An OCM system can provide improved alkene yield by in situ alkane cracking in a post-bed section of a reactor (post-bed cracking). Such in situ cracking of alkanes can provide a product stream with hydrocarbon distributions tailored for various end uses. This can advantageously provide $C_{2+}$ product stream that may be better suited for downstream uses, such as the commercial production of polymeric materials, as well as greater carbon efficiency of the overall process.

Post-bed cracking techniques can comprise control of temperature and residence time. Temperature and residence time can be chosen to favor higher ethylene concentration in the effluent from an OCM reactor. Post-bed cracking can be achieved using energy within the OCM effluent. Post-bed cracking can comprise cracking in the presence of OCM effluent steam. Cracking in the presence of steam, such as OCM effluent steam, can provide a higher C2 ratio.

Post-bed cracking can be conducted with a low residence time in the post-bed section. The residence time in the post-bed section can be less than or equal to about 500 milliseconds (ms), 450 ms, 400 ms, 350 ms, 300 ms, 250 ms, 200 ms, 150 ms, 140 ms, 130 ms, 120 ms, 110 ms, 100 ms, 90 ms, 80 ms, 70 ms, 60 ms, 50 ms, 40 ms, 30 ms, 20 ms, or 10 ms. The residence time in the post-bed section can be about 500 milliseconds (ms), 450 ms, 400 ms, 350 ms, 300 ms, 250 ms, 200 ms, 150 ms, 140 ms, 130 ms, 120 ms, 110 ms, 100 ms, 90 ms, 80 ms, 70 ms, 60 ms, 50 ms, 40 ms, 30 ms, 20 ms, or 10 ms.

Post-bed cracking can be conducted at a particular temperature or within a particular temperature range. The post-bed cracking temperature can be at least about 600° C., 650° C., 700° C., 720° C., 740° C., 760° C., 780° C., 800° C., 810° C., 820° C., 830° C., 840° C., 850° C., 860° C., 870° C., 880° C., 890° C., 900° C., 910° C., 920° C., 930° C., 940° C., or 950° C. The post-bed cracking temperature can be at most about 600° C., 650° C., 700° C., 720° C., 740° C., 760° C., 780° C., 800° C., 810° C., 820° C., 830° C., 840° C., 850° C., 860° C., 870° C., 880° C., 890° C., 900° C., 910° C., 920° C., 930° C., 940° C., or 950° C. The post-bed cracking temperature can be about 600° C., 650° C., 700° C., 720° C., 740° C., 760° C., 780° C., 800° C., 810° C., 820° C., 830° C., 840° C., 850° C., 860° C., 870° C., 880° C., 890° C., 900° C., 910° C., 920° C., 930° C., 940° C., or 950° C. The post-bed cracking temperature can be from about 800° C. to about 950° C. The post-bed cracking temperature can be from about 810° C. to about 950° C. The post-bed cracking temperature can be from about 820° C. to about 950° C. The post-bed cracking temperature can be from about 830° C. to about 950° C. The post-bed cracking temperature can be from about 840° C. to about 950° C. The post-bed cracking temperature can be from about 850° C. to about 950° C. The post-bed cracking temperature can be from about 860° C. to about 950° C. The post-bed cracking temperature can be from about 870° C. to about 950° C. The post-bed cracking temperature can be from about 880° C. to about 950° C.

The product stream from processes described herein can have particular compositions. In some cases, the product stream can comprise an acetone content less than or equal to about 100 parts-per-million (ppm), 50 ppm, 10 ppm, 5 ppm, 1 ppm, 100 parts-per-billion (ppb), 50 ppb, 10 ppb, 5 ppb, or 1 ppb. In some cases, the product stream can comprise a carbon dioxide ($CO_2$) content less than or equal to about 100 parts-per-million (ppm), 50 ppm, 10 ppm, 5 ppm, 1 ppm, 100 parts-per-billion (ppb), 50 ppb, 10 ppb, 5 ppb, or 1 ppb. In some cases, the product stream can comprise a carbon monoxide (CO) content less than or equal to about 100 parts-per-million (ppm), 50 ppm, 10 ppm, 5 ppm, 1 ppm, 100 parts-per-billion (ppb), 50 ppb, 10 ppb, 5 ppb, or 1 ppb. In some cases, the product stream can comprise an acetylene content less than or equal to about 2000 parts-per-million (ppm), 1000 ppm, 900 ppm, 800 ppm, 700 ppm, or 600 ppm. In some cases, the product stream can comprise a butene content less than or equal to about 200 parts-per-million (ppm) or 100 ppm. In some cases, the product stream can comprise a propylene content that is greater than or equal to about 0.2%, 0.4%, 0.6%, 0.8%, 1%, %, 3%, 4%, 5%, 6%, 7%, 8%, or 9% relative to an ethylene content of the product stream.

The post-bed region can be used to crack additional external hydrocarbons (e.g., ethane, propane) beyond those contained in the OCM effluent. The heat capacity in the OCM effluent can be sufficient to crack additional hydrocarbons. External hydrocarbons can be provided from a recycle stream. External hydrocarbons can be heated prior to injection into the post-bed section. External hydrocarbons can be heated by, for example, heat exchange with the OCM catalyst bed.

External hydrocarbons to be cracked in the post-bed section can be added sequentially based on carbon number. For example, external hydrocarbons with a lower carbon number (e.g., ethane) can be added to the post-bed cracking region upstream of where external hydrocarbons with a higher carbon number (e.g., propane) are added to the post-bed cracking region. The temperature in the post-bed cracking region can decrease going from the catalyst bed to the reactor outlet. Sequential adding of external hydrocarbons based on carbon number can be used to contact higher carbon number hydrocarbons with lower post-bed cracking temperatures. Sequential addition of external hydrocarbons can result in improved total olefin yields.

The present disclosure provides a reactor system comprising a plug flow reactor with a heat exchanger. The heat exchanger can include one or more heat exchange coils, such as at least 1, 2, 3, 4, 5, 6, 7, 8, 9, 10, 20, 30, 40, 50, or 100 coils. The coils can be part of the same fluid flow path (e.g., tube) or separate fluid flow paths. An OCM reactor can comprise a mixer on top of the reactor to mix a hydrocarbon stream (e.g., natural gas) with an oxygen or air stream. An OCM reactor can comprise an axial fixed catalytic bed, where a hydrocarbon feed stream exothermically reacts with an oxygen stream. An OCM reactor can comprise an empty space below the catalytic bed, which can allow control of residence time to optimize ethane cracking to ethylene (e.g., post-bed cracking). A reactor can comprise a mixer, an axial fixed catalytic bed, and a space for post-bed cracking; components can be designed to provide a plug-flow flow pattern through the reactor and to control residence times. Reactor outlet can be fed into a heat recovery steam generator (HRSG) tubesheet. An OCM reactor can comprise a heat exchanger (e.g., heat exchange coils, heat exchange tubes). A heat exchanger can be located before the reactor outlet, such as after a post-bed cracking space and before feeding into an HRSG tubesheet. A heat exchanger can be used to cool down reactor OCM effluent. A heat exchanger can be used to heat an OCM feed stream. A heat exchanger can be used to heat saturated steam. A heat exchanger can be used to heat boiler feed water (BFW). A heat exchanger can be used to heat an oxygen or air stream. A heat exchanger can reduce the temperature of an OCM effluent stream below the temperature range at which cracking reactions can occur (e.g., below 600° C.). This can reduce or prevent coke formation, such as coke formation in an HRSG system.

Figure 19:
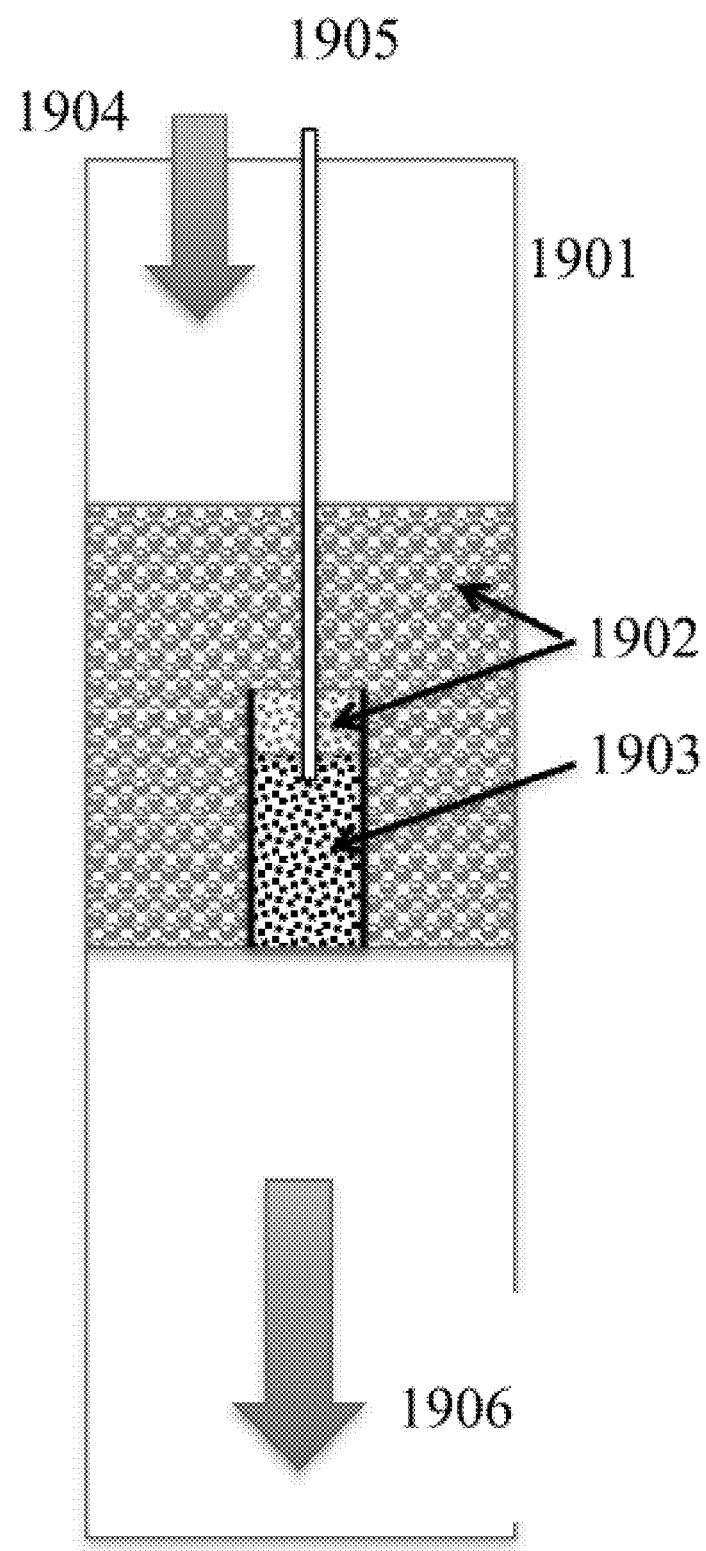
FIG. 19 shows a schematic of an OCM reactor with an inert packing zone.

Reactor systems can comprise a low flow pocket with catalytically inert material. FIG. 19 shows a reactor 1901 with an OCM catalyst bed 1902. The low flow pocket can be in at least a portion of the catalyst bed 1902 or extend through all or substantially all of the catalyst bed 1902, such as at least about 20%, 30%, 40%, 50%, 60%, 70%, 80%, 90%, 95%, or 99% of the catalyst bed 1902. A region of catalytically inert material 1903 can be included in the catalyst bed. The catalytically inert material can include a material that does not facilitate or appreciably facilitate an OCM process. A stream of natural gas and oxygen 1904 can be flowed into the reactor inlet. A stream of other hydrocarbons (e.g., C2, C3) 1905 can be injected into the inert region. A product stream 1906 of OCM and cracking products can exit the reactor. An inert region can be used to create a low flow pocket. The inert region can comprise different particle sizes compared to the main catalyst bed. The inert region can discharge into the post-bed cracking region. The inert region can result in an increased residence time for material injected into the region (e.g., C2 and C3 hydrocarbons). Increased residence time can result in additional heat transfer to the injected material. Most or all of the oxygen provided to the reactor can be consumed upstream of the inert region. At least about 50%, 60%, 70%, 80%, 90%, 95%, 96%, 97%, 98%, 99%, 99.9%, 99.99%, 99.999%, or 100% of the oxygen provided to the reactor can be consumed upstream of the inert region.

Prior to cracking, alkanes such as ethane or propane can be pre-heated. Alkanes can be pre-heated to a temperature of at least about 500° C., 510° C., 520° C., 530° C., 540° C., 550° C., 560° C., 570° C., 580° C., 590° C., 600° C., 610° C., 620° C., 630° C., 640° C., 650° C., 660° C., 670° C., 680° C., 690° C., 700° C., 710° C., 720° C., 730° C., 740° C., 750° C., 760° C., 770° C., 780° C., 790° C., 800° C., 810° C., 820° C., 830° C., 840° C., 850° C., 860° C., 870° C., 880° C., 890° C., or 900° C. Pre-heating can be conducted in the presence of steam. Steam can be added as an oxidant. Steam can be added as a diluent. Pre-heating can be conducted in the absence of steam. Pre-heating can be conducted in the presence of $CO_2$. $CO_2$ can be added as an oxidant. $CO_2$ can be added as a diluent (i.e., a diluting agent). The specific heat capacity of $CO_2$ is about 2.5 times lower than that of steam. Mixing hydrocarbons with $CO_2$ rather than with steam can result in a higher mixture temperature. The rate of ethane thermal cracking can be enhanced by the presence of $CO_2$. Increased concentrations of $CO_2$ can shift the Boudouard reaction to the left and mitigate coke production. A system using added $CO_2$ can comprise a downstream amine scrubber for $CO_2$ separation.

A hybrid reactor system can be employed which combines isothermal and adiabatic sections. An isothermal section can comprise a tubular reactor as described herein. Process operating conditions, such as inlet temperature, flow rate, and heat transfer medium level, can be controlled to produce reactor effluent (e.g., OCM reactor effluent) at a desired temperature or composition. A hybrid reactor comprising a first isothermal tubular stage followed by a second adiabatic stage can provide high conversion, high ethylene yield, and high C2 ratio.

The present disclosure provides for a reactor system comprising a two-reactor configuration. A two-reactor system can comprise a first OCM reactor and second cracking reactor. The second cracking reactor can comprise a smaller diameter or width than the first OCM reactor. The first OCM reactor can comprise a tubular reactor. The second cracking reactor can comprise a tubular reactor. At least about 50%, 60%, 70%, 80%, 90%, 95%, 96%, 97%, 98%, 99%, 99.9%, 99.99%, 99.999%, or 100% of the oxygen provided to the first OCM reactor can be consumed within the first OCM reactor. The outlet stream from the first OCM reactor can be fed into the second cracking reactor. The second cracking reactor can be heated. The residence time within the second cracking reactor can be smaller than the residence time within the first OCM reactor by at least about 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, or 1000 times. Relative residence times can be controlled by designing the relative diameter or width of the two reactors. The second cracking reactor can comprise packing or support material (e.g. SiC rings or spheres). Packing or support material can provide additional surface area for cracking.

Auto-Thermal Reforming

Systems of the present disclosure may be employed for use in auto-thermal reforming (ATR). In ATR, methane reacts with oxygen and steam to produce syngas (primarily CO and $H_2$) with a targeted $CO/H_2$ ratio. An ATR reactor typically includes a burner followed by a catalytic bed containing an ATR catalyst (e.g., nickel). In the burner, combustion is the primary reaction and generates the heat that is then used in the catalytic bed to feed the reforming reactions. In the catalytic bed, reactions approach near final chemical equilibrium at a significantly lower temperature than in the burner zone, which may be thermodynamically favorable and leads to higher conversions.

From a chemical process standpoint, the optimal design for an ATR unit may be one where both combustion and reforming reactions occur simultaneously over a catalytic bed. Such a design is described as a flame-less ATR, i.e., an ATR without the burner zone. While this design may lead to higher conversion and reduced consumption of oxygen, its technical implementation is only enabled if a suitable mixer exists, such as, for example, a mixer that 1) mixes methane-containing and oxygen-containing streams with the required degree of uniformity prior to entering the catalytic bed for ATR, and 2) mixes the methane-containing and oxygen-containing streams entirely within the auto-ignition delay time. In fact, if only a portion of the mixed stream is allowed to spend longer than the auto-ignition delay time in the mixer zone, combustion can start, thus generating a flame that may propagate through the entire mixture. The catalytic bed would not be able to withstand the flame temperature, leading to a technical failure of the ATR system. Conversely, if the mixer can uniformly combine the entire streams within the maximum allowable time, the un-reacted mixed stream can proceed to the catalytic bed, where methane can be optimally converted to syngas. In view of this requirement, the distribution of residence times in the mixer can be such that 100% of the mixed stream spends less than the auto-ignition delay time in the mixer itself.

Auto-thermal reforming systems of the present disclosure can include mixers, which can reduce auto-ignition delay times prior to directing methane and oxygen to an ATR catalyst. In some embodiments, a method for flame-less auto-thermal reforming (ATR) to generate syngas comprises mixing a first gas stream comprising methane with a second gas stream comprising oxygen to form a third gas stream, and prior to auto-ignition of the third gas stream, performing a flame-less ATR reaction using the third gas stream to produce a product stream comprising hydrogen ($H_2$) and carbon monoxide (CO).

For example, a mixer for use in ATR can uniformly combine two or more gaseous streams into one gaseous stream while allowing for the mixed stream in its entirety to spend only a maximum allowable time in the mixer itself. The mixer can include a series of parallel airfoil-shaped manifolds inserted in the cross section of a reactor or any other flow device, such as a pipe, that carries one of the gaseous streams. The other gaseous streams are fed to the airfoil-shaped manifolds, which have suitably designed ports to enable the injection of the gas inside the manifolds into the main gaseous stream flowing outside the manifolds.

Computer Control Systems

The present disclosure provides computer control systems that can be employed to regulate or otherwise control OCM methods and systems provided herein. A control system of the present disclosure can be programmed to control process parameters to, for example, effect a given product distribution, such as a higher concentration of alkenes as compared to alkanes in a product stream out of an OCM reactor.

Figure 20:
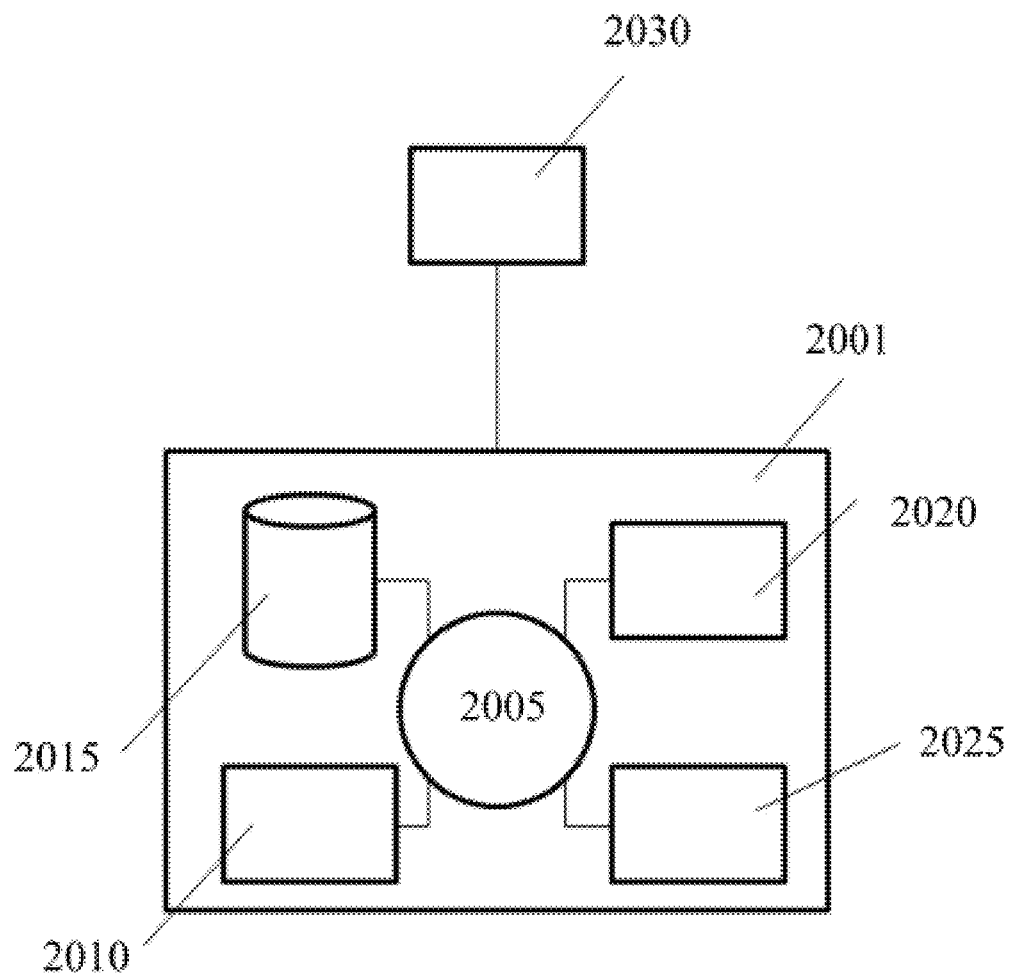
FIG. 20 shows a computer system that is programmed or otherwise configured to regulate OCM reactions.

FIG. 20 shows a computer system 2001 that is programmed or otherwise configured to regulate OCM reactions, such as regulate fluid properties (e.g., temperature, pressure and stream flow rate(s)), mixing, heat exchange and OCM reactions. The computer system 2001 can regulate, for example, fluid stream ("stream") flow rates, stream temperatures, stream pressures, OCM reactor temperature, OCM reactor pressure, the quantity of products that are recycled, and the quantity of a first stream (e.g., methane stream) that is mixed with a second stream (e.g., air stream).

The computer system 2001 includes a central processing unit (CPU, also "processor" and "computer processor" herein) 2005, which can be a single core or multi core processor, or a plurality of processors for parallel processing. The computer system 2001 also includes memory or memory location 2010 (e.g., random-access memory, read-only memory, flash memory), electronic storage unit 2015 (e.g., hard disk), communication interface 2020 (e.g., network adapter) for communicating with one or more other systems, and peripheral devices 2025, such as cache, other memory, data storage and/or electronic display adapters. The memory 2010, storage unit 2015, interface 2020 and peripheral devices 2025 are in communication with the CPU 2005 through a communication bus (solid lines), such as a motherboard. The storage unit 2015 can be a data storage unit (or data repository) for storing data.

The CPU 2005 can execute a sequence of machine-readable instructions, which can be embodied in a program or software. The instructions may be stored in a memory location, such as the memory 2010. Examples of operations performed by the CPU 2005 can include fetch, decode, execute, and writeback.

The storage unit 2015 can store files, such as drivers, libraries and saved programs. The storage unit 2015 can store programs generated by users and recorded sessions, as well as output(s) associated with the programs. The storage unit 2015 can store user data, e.g., user preferences and user programs. The computer system 2001 in some cases can include one or more additional data storage units that are external to the computer system 2001, such as located on a remote server that is in communication with the computer system 2001 through an intranet or the Internet.

The computer system 2001 can be in communication with an OCM system 2030, including various elements of the OCM system. Such elements can include sensors, flow regulators (e.g., valves), and pumping systems that are configured to direct a fluid.

Methods as described herein can be implemented by way of machine (e.g., computer processor) executable code stored on an electronic storage location of the computer system 2001, such as, for example, on the memory 2010 or electronic storage unit 2015. The machine executable or machine readable code can be provided in the form of software. During use, the code can be executed by the processor 2005. In some cases, the code can be retrieved from the storage unit 2015 and stored on the memory 2010 for ready access by the processor 2005. In some situations, the electronic storage unit 2015 can be precluded, and machine-executable instructions are stored on memory 2010.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Although systems and methods of the present disclosure have been described in the context of methane and air (or oxygen), such systems and methods may be employed for use with other hydrocarbons and oxidizing agents (e.g., $NO_3$, $NO_2$, or $O_3$). Non-limiting examples of hydrocarbons include alkanes, alkenes, alkynes, aldehydes, ketones, and combinations thereof. For instance, mixers and integrated heat exchanges of the disclosure may be employed for use with ethane, propane, pentane, or hexane. Non-limiting examples of oxidizing agents include $O_2$, $H_2O_2$, $NO_3$, $NO_2$, $O_3$, and combinations thereof. Moreover, although certain examples of the present disclosure have made reference to air, other fluids containing oxygen or an oxidizing agent (e.g., $NO_2$) may be used.

EXAMPLES

Example 1—Post-Bed Cracking of Ethane

Figure 21:
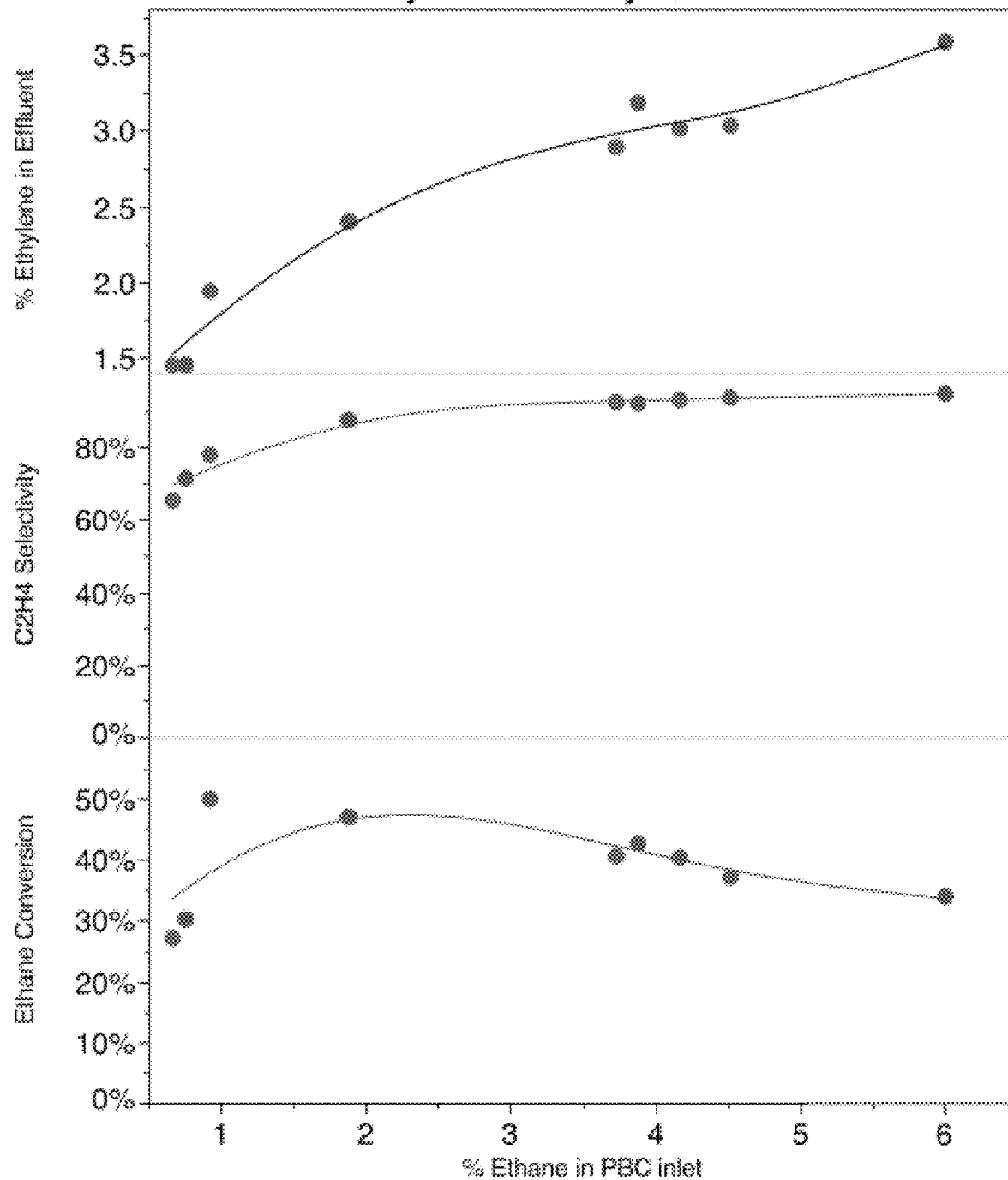
FIG. 21 shows a plot of data for ethane conversion and ethylene selectivity in a post-bed cracking (PBC) process.

A reactor system is provided comprising an OCM reactor with an OCM catalyst bed section and a post-bed cracking section. The ratio of methane and oxygen provided to the OCM catalyst bed section is adjusted to control the temperature of the stream at the outlet of the OCM catalyst bed section leading into the post-bed cracking section. The temperature is between about 880° C. and about 900° C. Results are shown in FIG. 21 for percent ethylene in post-bed cracking section effluent versus percent ethane in post-bed cracking section inlet stream (upper graph), for $C_2H_4$ selectivity versus percent ethane in post-bed cracking section inlet stream (middle graph), and for ethane conversion versus percent ethane in post-bed cracking section inlet stream (lower graph).

Example 2—Flow Splitting Reactor

Figure 22:
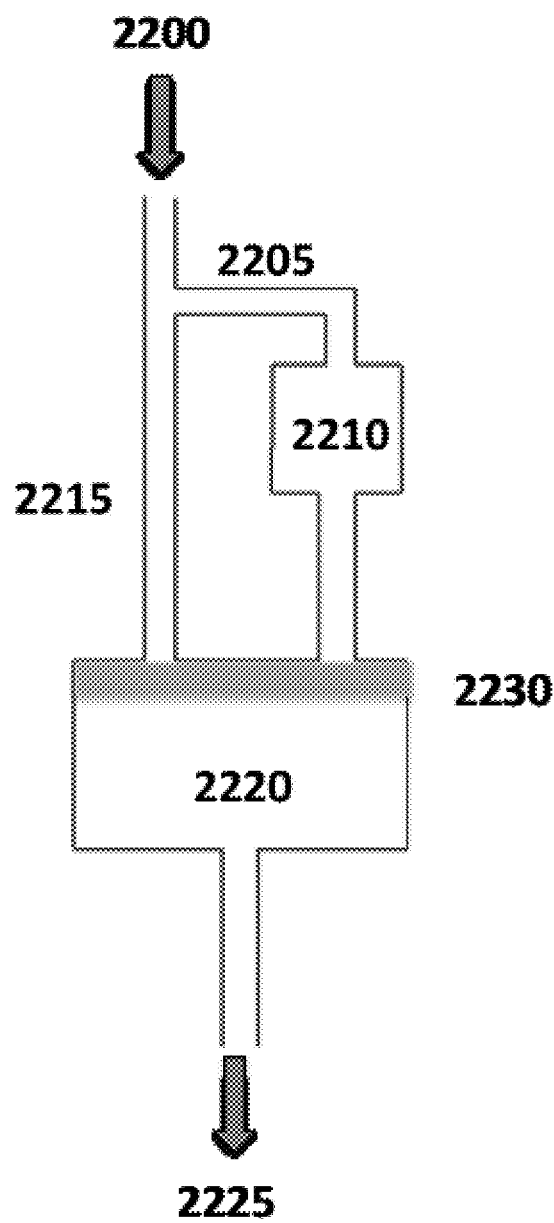
FIG. 22 shows an example of performing an OCM reaction with bypass.

An example of a reactor having a flow split of the OCM feed gas is shown in FIG. 22. Here, the OCM gas feed mixture 2200 containing both natural gas and oxygen is first split into two streams. A first stream 2205 is then reacted in a first OCM reactor 2210 before having its effluent recombined with the second stream 2215. The combined stream is then reacted further in a second OCM reactor 2220 or catalyzed reactor section to produce a product 2225. The first and/or second OCM reactors can have a mixer or mixing region 2230. In some cases the first and second OCM reactors are regions of a single OCM reactor.

The ratio of gas flow directed to the first reactor to the total feed flow in the system can be between about 5% and about 50%, or in some cases between about 10% and about 35%. The feed inlet temperature can be between about 400° C. and about 550° C. with an amount of oxygen in the feed as needed to achieve a system outlet temperature (or adiabatic temperature of the product mixture) of between about 820° C. and about 920° C.

For an adiabatic system, the inlet temperature of a well-mixed stream at the inlet to the second OCM 2220 can be adjusted to be between about 500° C. and about 750° C. or between about 600° C. and about 700° C. by choosing the proper ratio of the flow of the first stream 2205 to the second stream 2215.

The extent of mixing in the second OCM reactor 2220 can be adjusted to avoid or create non axial (in flow direction) temperature and oxygen concentration gradients. There can be instances where these gradients are desirable to improve system operability (e.g., for operation below light off inlet temperature of the catalyst and above extinction temperature of the catalyst of reactor). In some cases, hot spots at the front end of the second reactor 2220 reactor can promote catalyst activity at the front end of the catalyst bed.

Example 3—Flow Splitting Reactor

Figure 23:
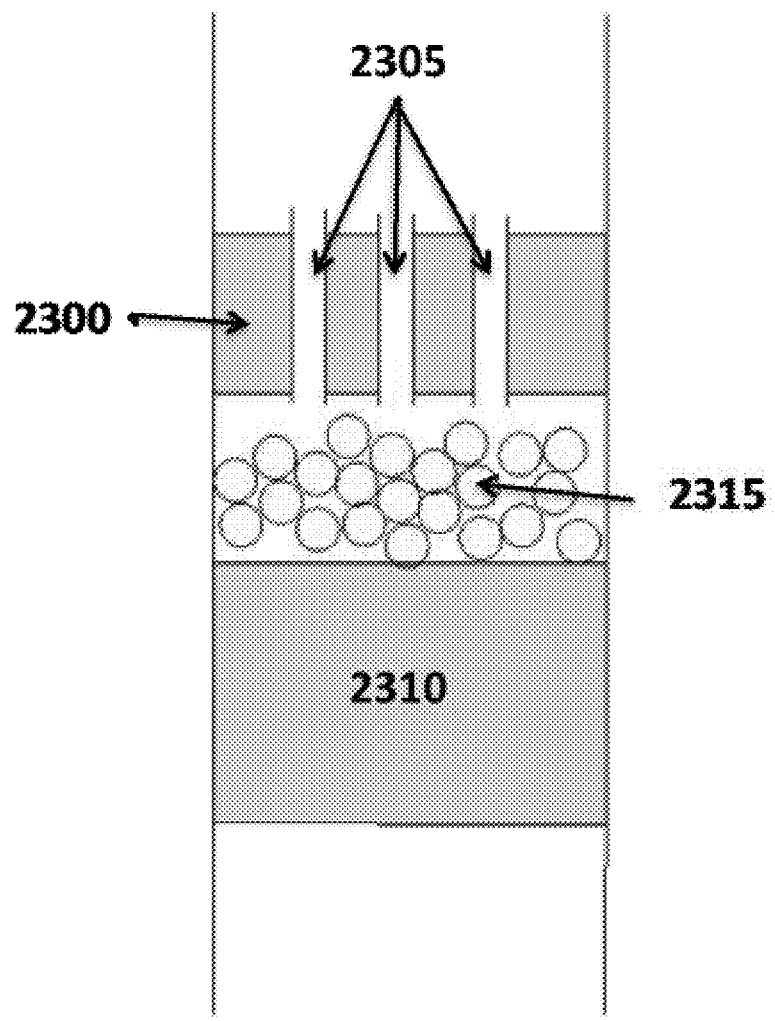
FIG. 23 shows an example of a reactor for performing an OCM reaction with bypass.

Another example of a reactor having OCM flow split is shown in FIG. 23. In this design, a first OCM reactor 2300, one or more bypass legs 2305 and the second OCM reactor 2310 are contained within the same reactor shell. Flow splitting and bypass of the OCM feed gas is obtained by imbedding catalytically inert tubes within the catalyst packing to provide pathways for the feed gas through the first reactor section 2300 that is free of contact from catalytically active surfaces. A mixing region 2315 can be provided between the first and second OCM reactor sections.

The reactor system was assembled according to the schematic shown in FIG. 23. The catalyst shape was 3 mm extrudate cut into about 1 cm lengths. The refractory lined container internal diameter (ID) was 2.2 inches. The first OCM reactor section was 3 inches long with three 10 mm ID quartz tubes set to bypass about 70% of the inlet feed to the second reactor section.

One inch of Zirconia beads (3 mm diameter) were used in the mixer region 2315 to mix the bypass flow and the reactor streams from the first reactor section.

The second reactor section 2310 also used a 3 inches long OCM catalyst bed made of the same catalyst material as the first reactor section.

The gas linear velocity through the OCM catalyst packing in the first section was about 35% of the gas linear velocity through the OCM catalyst packing in the second section. The contact time of the reacting feed to the catalyst is about 3-fold greater in the first OCM reactor section 2300 than in the second OCM reactor section 2310.

Example 4—Separate Reaction of Wet and Dry Natural Gas

The flow splitting reactors and methods described herein can also be used for different gas feeds being processed in different reactors or reactor subsections. A potential benefit of such an implementation can be that processing of wet natural gas feed (e.g., containing above 2% $C_{2+}$ hydrocarbons) in the second OCM reactor can be more effective than processing this mixture through a single packed bed reactor.

Figure 24:
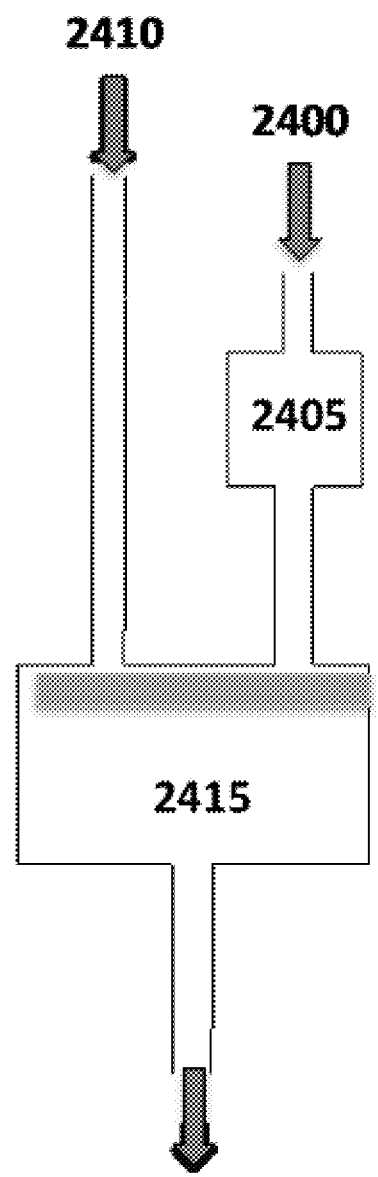
FIG. 24 shows an example of performing an OCM reaction with multiple feedstocks.

With reference to FIG. 24, when both dry and wet natural gas feeds are available (e.g., when using a pressure swing adsorption system to dry part of the natural gas coming into the plant), it can advantageous to use the dry natural gas feed 2400 to provide heat and product through the first OCM reactor section 2405, while the wet natural gas feed 2410 can be directed to the second OCM reactor section 2415 to minimize combustion of the $C_{2+}$ molecules contained in the wet gas feed. The hydrocarbon to oxygen ratio and preheating temperature of the two feed streams can be controlled independently.

Figure 25:
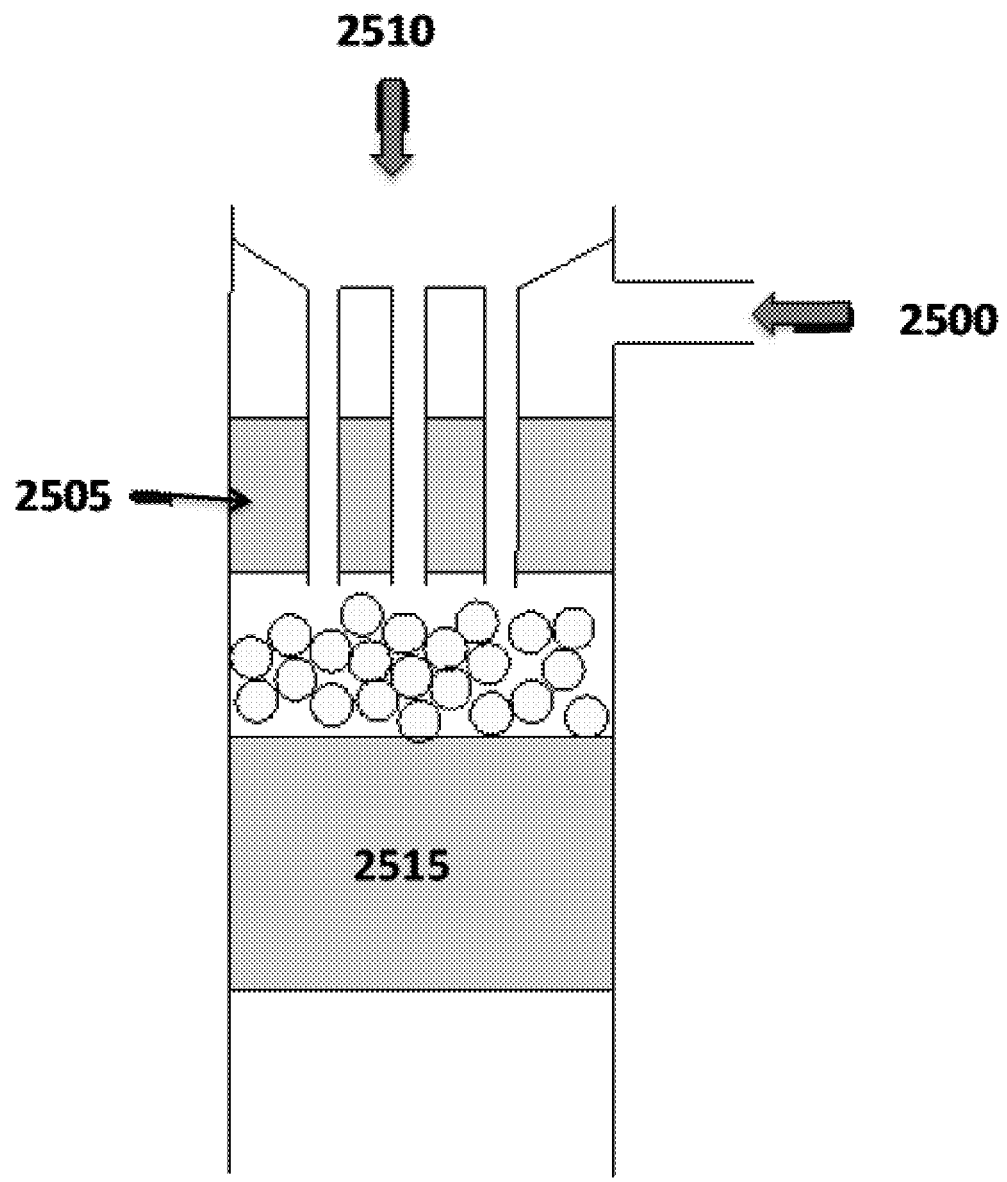
FIG. 25 shows an example of a reactor for performing an OCM reaction with multiple feedstocks.

In some cases, integration within a single shell can be desirable (e.g., to minimize heat losses and residence time of the unreactive feed prior to contact the catalytic material). FIG. 25 shows an embodiment of such system with separate feeds. A first feed 2500 is directed into a first reactor or reactor segment 2505 and a second feed 2510 is directed into a second reactor or reactor segment 2515. The feeds can differ in any number of ways including by their natural gas to oxygen ratio, by their temperature of pre-heating, or being for wet and dry natural gas.

This embodiment can allow external control of the split ratio of bypass gas to total gas (in contrast to a system relying on pressure drop defined by the catalyst bed packing flow resistance to set the split ratios).

Example 5—Flow Splitting Reaction

The reactor system assembled in Example 3 was tested for OCM catalytic performance when used as the second reactor in a series of OCM reactors. The reactor system inlet contained a mixture of methane, ethylene, ethane, CO, $CO_2$, water and hydrogen, to which air was added.

Figure 26:
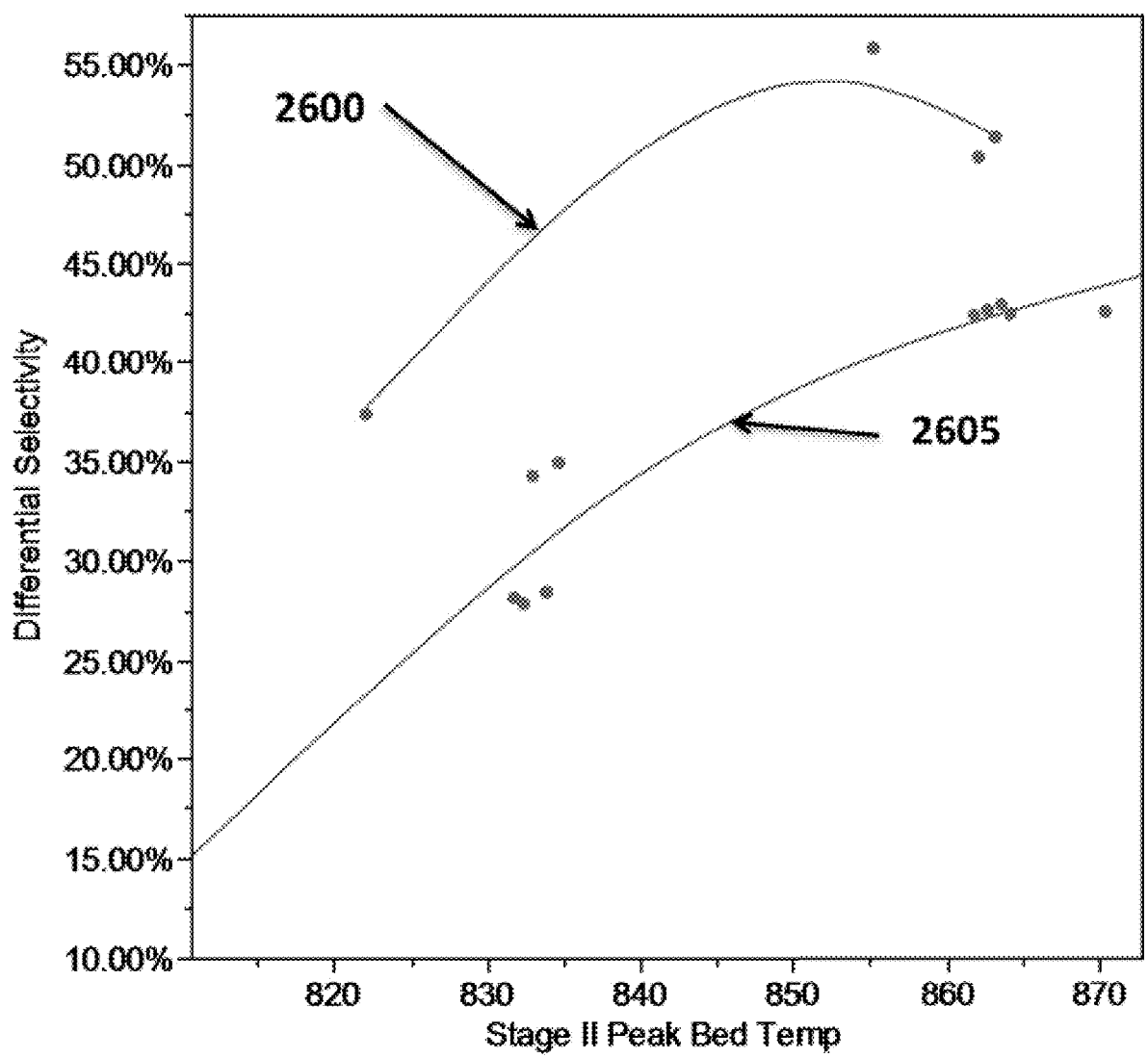
FIG. 26 shows an example of the effect of selectivity as a function of peak bed temperature for OCM with bypass.

Performance of the reactor system with bypass tubes was compared to the performance of the same catalyst (and amount thereof) without flow splitting and staged reaction of the oxygen. FIG. 26 compares the differential selectivity as a function of peak bed temperature for the system with a bypass reactor 2600 and without a bypass reactor 2605. Differential (net) selectivity to higher hydrocarbons (ethylene, ethane, propane and propylene) was measured as a function of the amount of oxygen injected, resulting in different adiabatic operating temperatures for the reactor back end. The data points shown are for a reactor system inlet temperature of 515° C.

This example shows the benefit with regard to selectivity of the staging of oxygen consumption in different reactor sub-sections for the selective coupling of methane of feed gas containing highly reactive species.

Figure 27:
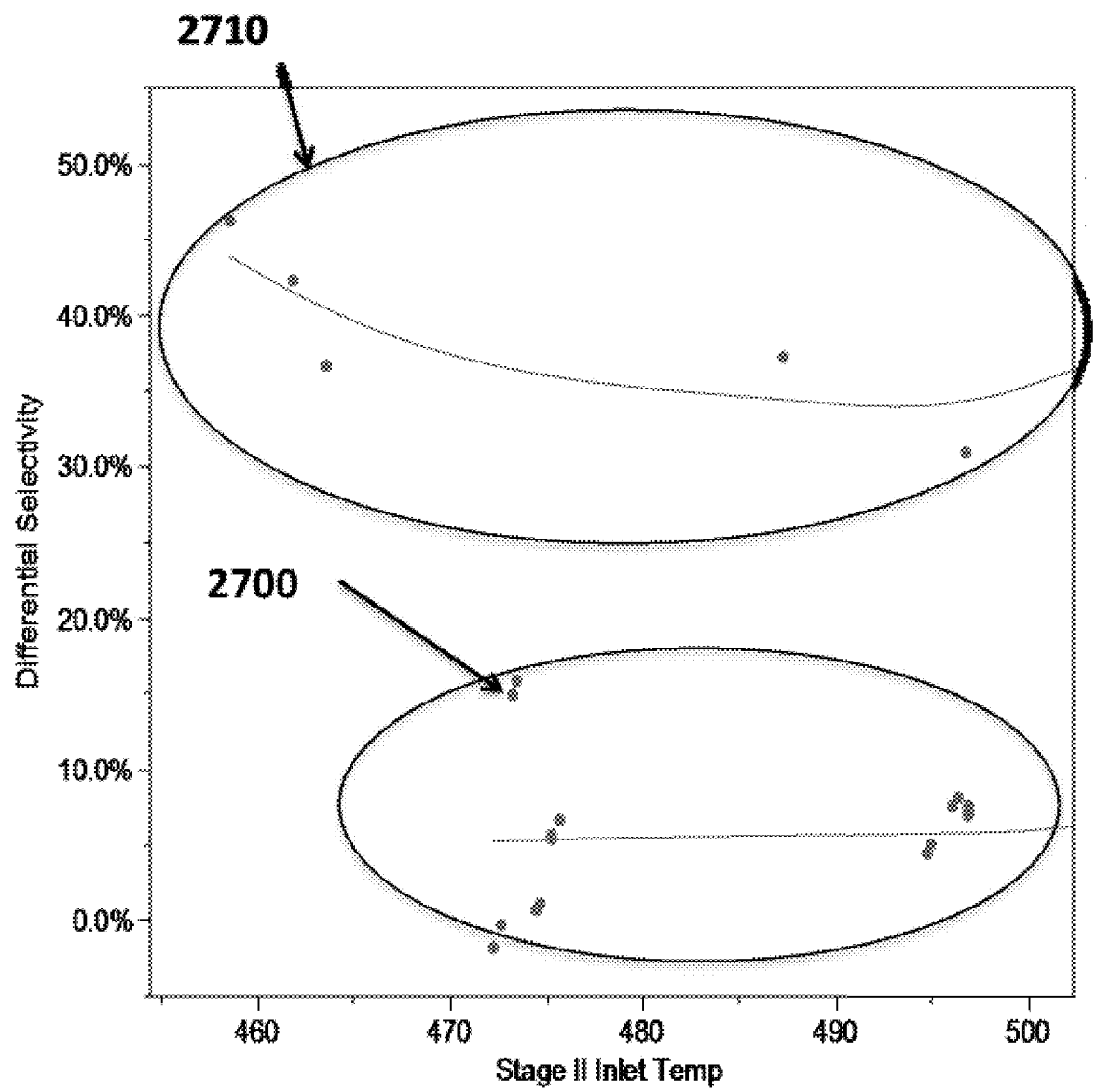
FIG. 27 shows an example of the effect of selectivity as a function of inlet temperature for OCM with bypass.

FIG. 27 shows performance versus the reactor system inlet feed temperature. Here, the single packed bed performance quickly drops with inlet temperature 2700, whereas the split flow system with staged oxygen consumption is still operational down to about 460° C. 2710. Oxygen breakthrough analysis also shows the same trend (data now shown).

Example 6—Reactor with Heat Exchange

Figure 28:
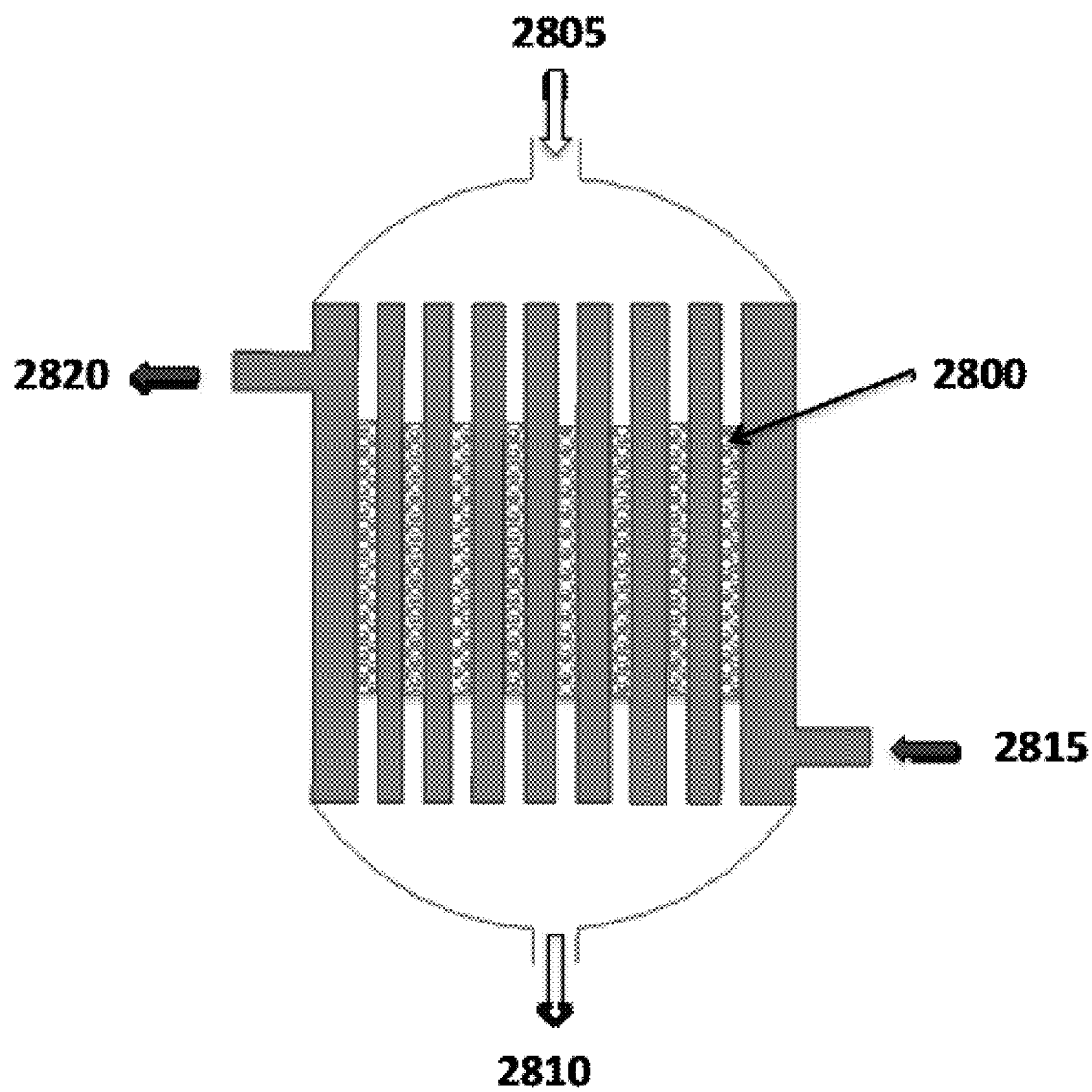
FIG. 28 shows an example of a reactor with heat transfer capability using molten salts.

The reactors with heat exchange described herein can be used to remove or inject heat into a catalyst bed carrying out an exothermic or endothermic chemical reaction. FIG. 28 presents a schematic drawing of a typical reactor with heat exchange. The catalyst bed 2800 is loaded in narrow and long tubes assembled into an area of the reactor that has feed gas flowing into the reactor 2805 and product gas flowing out of the reactor 2810. The outer side of the tube is contacted with a heat transfer media that enters 2815 and exits 2820 the reactor, but does not directly contact the catalyst bed. Molten salt are the preferred heat transfer media for temperatures above about 400° C. and below about 600° C.

As OCM can be performed at temperature as low as 420° C. (e.g., using catalyst described in U.S. patent application Ser. No. 13/115,082, U.S. patent application Ser. No. 13/479,767, U.S. patent application Ser. No. 13/689,611, and U.S. patent application Ser. No. 13/901,319, each of which is incorporated herein by reference in its entirety), the molten salt cooled tubular reactors described herein can be used to build a reactor system with increased ethylene yield compared to adiabatic type reactors. Additional description of performing OCM in reactors with heat exchange can be found in U.S. patent application Ser. No. 13/900,898, which is incorporated herein by reference in its entirety.

Demonstration of the benefit of this type of reactor was carried out a pilot scale using 5 feet long single tube reactors. In the following examples, different catalyst packing strategies enhanced the reactor performance or operability as described.

Example 7—Molten Salt OCM Tubular Reactor

A one-inch section of schedule 40 pipe (1.05 inches ID) made of 304 stainless steel was welded to a U tube. A packed bed of 14 inches of OCM catalyst having ring shaped particles of 6 mm OD and 3 mm ID was loaded in the tube. The reactor tube was immersed in a HITEC heat transfer salt bath with a molten level above the exit of the catalyst bed packing. The molten salt was circulated to insure good temperature uniformity of the molten salt bath.

Feed gas coming into the bottom of the 1-inch pipe through the U tube was pre-heated by the hot molten salt before contacting the OCM catalyst in the pipe.

The molten salt temperature was controlled between 450° C. and 550° C. External wall temperature of the pipe was measured every 3 inches and the catalyst operating conditions were adjusted to keep the outer pipe wall temperature under 600° C.

Methane and air mixtures were fed through the reactor at total gas flow rate between 50 and 100 SLPM (standard liter per minute) and a pressure between 1 and 2 bar-gauge (barg). The ratio of methane to oxygen was varied between 4 and 10.

Example 8—Effect of Bed Packing

The reactor described in Example 7 was packed with a catalyst packing divided into two sections. A first section (3 inches long) was separated from a second section (11 inches long) section by 2 inches of silicon carbide bead packing (6 mm diameter). The silicon carbide is chemically inert and does not activate methane or oxygen. However, this inactive material allows for cooling of the partially reacted process stream, resulting in a significant change in the axial temperature profile of the reactor.

Figure 30:
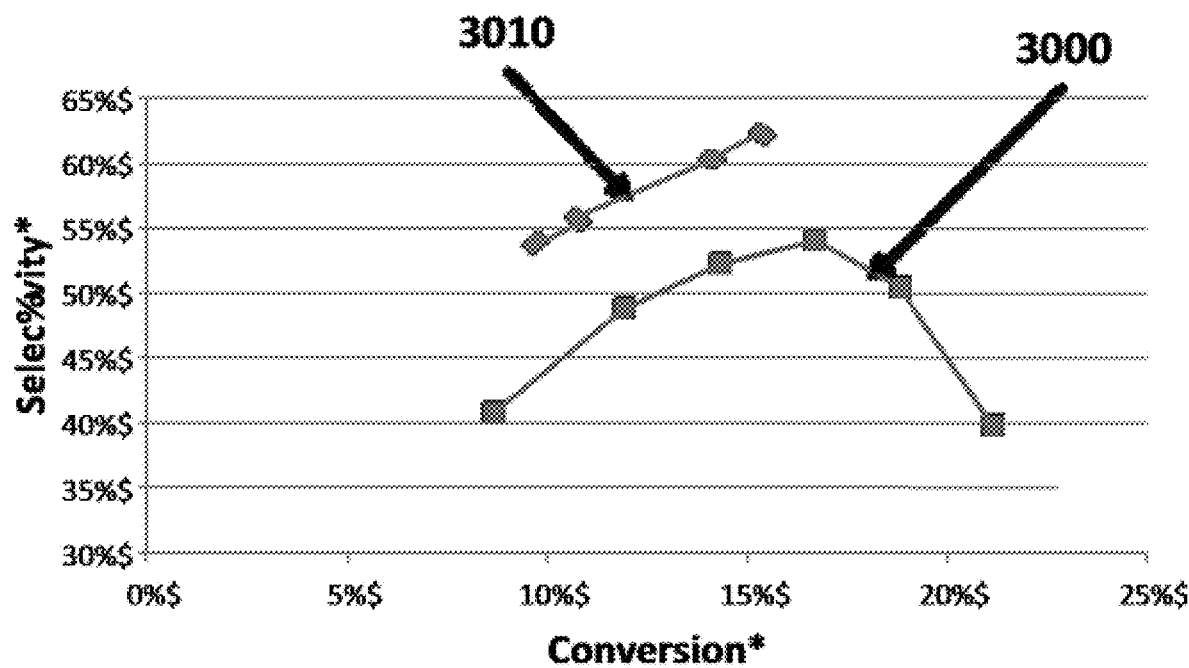
FIG. 30 shows an example of the effect of catalyst packing geometry.

FIG. 30 shows a graph of $C_{2+}$ selectivity of the OCM reaction versus methane conversion. The un-segmented catalyst bed (14-inch) described in Example 7 is shown as square markers 3000 and the segmented catalyst bed (3-inch and 14-inch sections) is shown as diamond markers 3010. The comparison of the two bed packing geometries was performed at about 1.5 barg and a total feed flow of 50 SLPM with a molten salt temperature of 550° C.

FIG. 30 shows that the segmented catalyst bed has an improved $C_{2+}$ selectivity. This difference is also reflected in the thermal profile of the catalyst with a decreased peak temperature for the segmented bed versus the non-segmented bed (data not shown). While the reactor wall temperature is maintained below 600° C., the center of the tube can reach temperature in excess of 900° C. A stable axial and radial temperature profile was observed in the catalyst bed. As hot catalyst spots above 900° C. can be detrimental to the selectivity of the OCM reaction, addition of axial cooling bands can affect the operating window and performance of the tubular molten salt cooled reactor.

Example 9—OCM with Low Linear Flow Velocity

Figure 31:
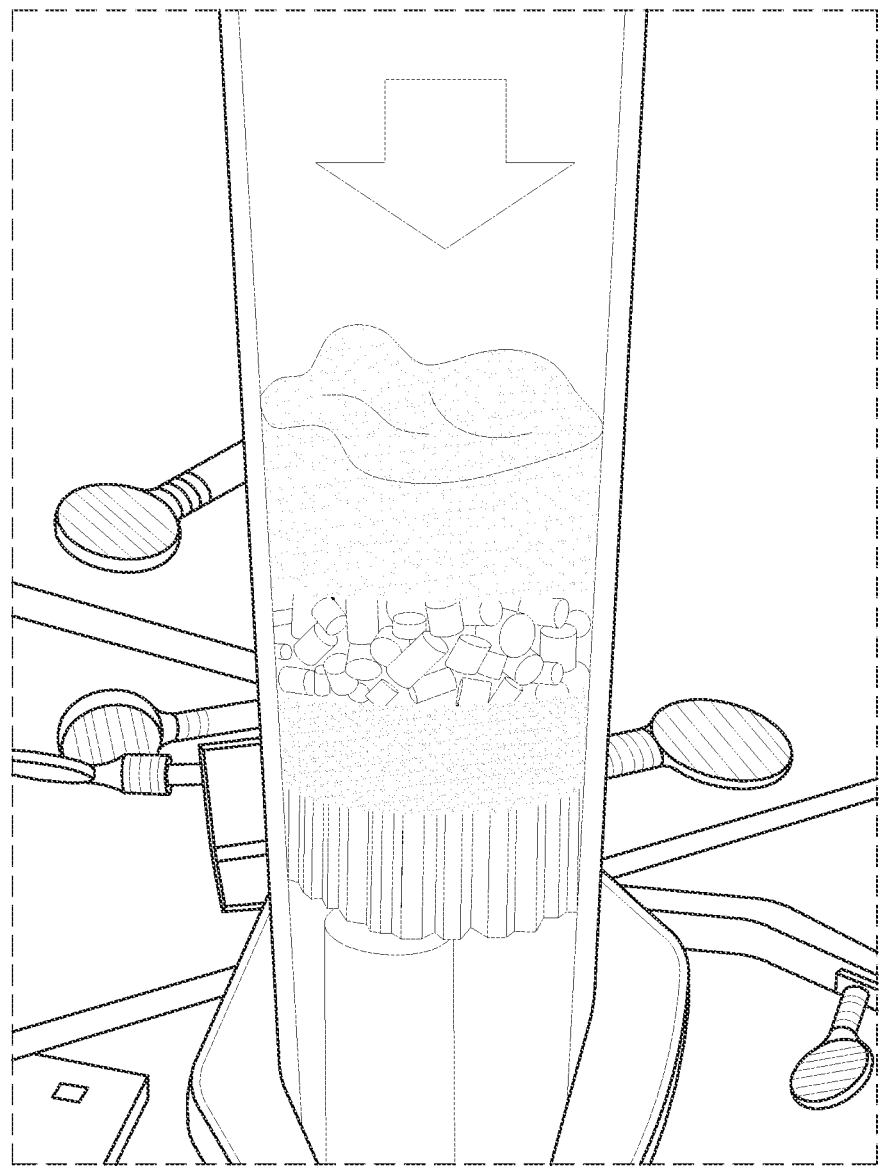
FIG. 31 shows an example of a low linear velocity OCM reactor.

The reactor shown in FIG. 31 was used to perform OCM at a low linear gas velocity. The reactor is a quartz reactor with 22 mm ID and 24 mm OD. External surface of the quartz reactor (the catalyst bed section) was densely covered by layers of insulation in order to minimize heat loss from the catalyst bed. The standard reaction (i.e., non-low linear velocity) was performed using 8 mm quartz tubing. The quartz tubing was inside stainless steel tubing for the quartz tubing housing.

The OCM catalyst was an extrudate that was used for both regular (i.e., non-low linear velocity run) and low linear velocity trials. The extrudate was approximately 2 mm in diameter and length. The catalyst bed height in the quartz reactor was 5 mm. As shown in FIG. 31, the catalyst bed was sandwiched by inert ceramic wool layers for flow uniformity and minimization of radiation heat transfer.

The flow rates employed in the low linear velocity trials are listed in the table below.

| Reactor | 8 mm, Regular Velocity | 22 mm, Low Linear Velocity | |
|---|---|---|---|
| I.D. (mm) | 8 | 22 | 22 |
| Cross-sectional area (cm2) | 0.5 | 3.8 | 3.8 |
| Bed height (cm) | 2.0 | 0.5 | 0.5 |
| CH4 flow (SCCM) | 400 | 600 | 900 |
| Air flow (SCCM; for CH4/O2 = 10) | 190.5 | 285.7 | 428.6 |
| Feed flow (SCCM) | 590.5 | 885.7 | 1328.6 |
| Linear velocity (cm/min) | 796.2 | 157.9 | 236.9 |
| GHSV (1/hour) | 35,259 | 27,974 | 41,962 |

The furnace temperature was raised slowly (ramping rate 2° C./min) for low linear velocity runs. The steady state performance was measured when the furnace temperature reached the target temperatures (500° C., 550° C., 600° C., 650° C. and 700° C., respectively). The feed mixture preheating temperature reading (measured on top of the inert ceramic wool layer) was slightly lower than furnace temperature, but within about 10° C. For regular runs (non-low linear velocity runs), the furnace ramping temperature was 3° C./min and the furnace temperature was used for the preheating temperature.

Figure 32:
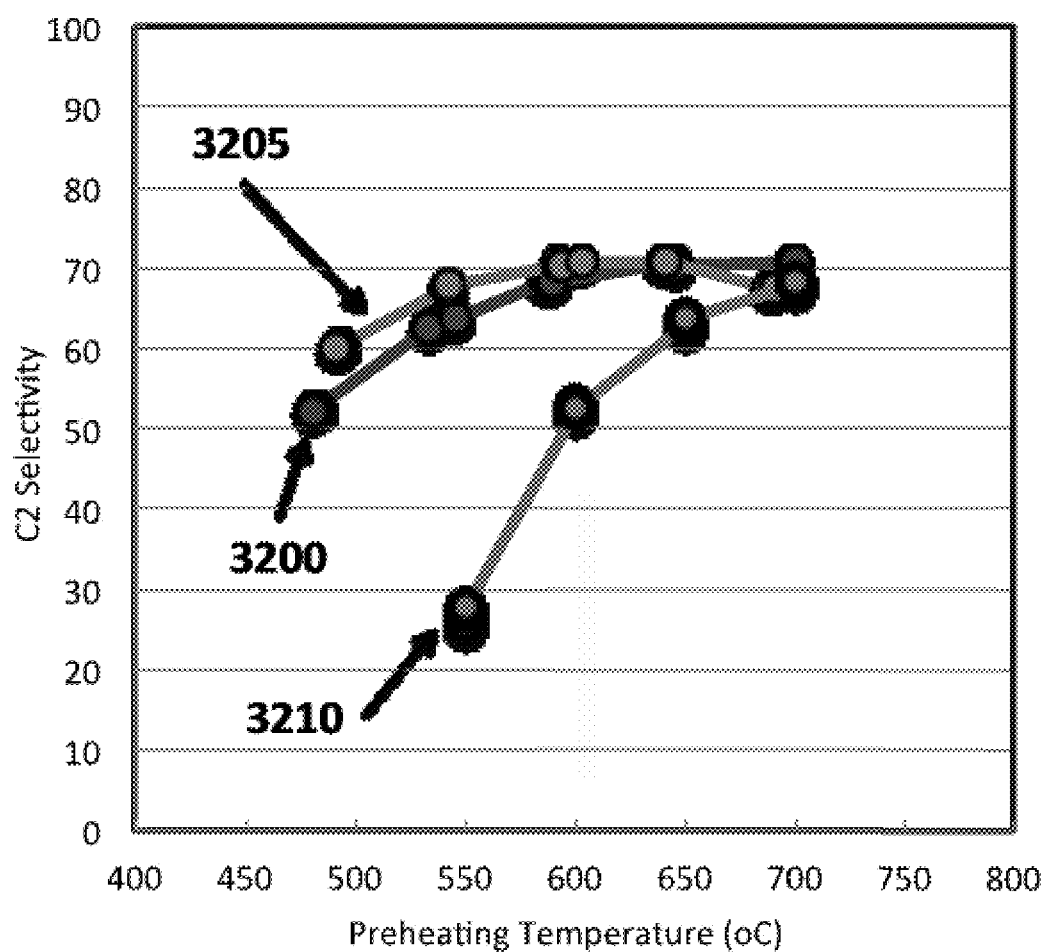
FIG. 32 shows an example of the effect of performing the OCM reaction at low linear velocity.

The C2 selectivity (% ethlyene+ethane) is plotted versus temperature in FIG. 32. The results show that low linear velocity (600 SCCM 3200 or 900 SCCM 3205) can have a higher selectivity than high linear velocity (8 mm reactor 3210). Comparing the performance of the low L/D aspect ratio catalyst bed to a higher L/D aspect ratio for C2 selectivity shows an improved selectivity for the thinner bed operated with low feed gas linear velocity. C2 Selectivity at 550° C. gas inlet temperature increases from about 25% to about 65% by changing the geometry of the catalyst container, which can illustrate the influence of the thermal profile within the catalyst bed on OCM reaction product distribution. Another benefit of a low linear velocity can be the ability to use smaller catalyst particulates in the bed, as flow resistance typically scales with linear velocity.

Some low linear velocity reactors include a radial reactor design in which the catalyst bed entrance area is maximized relative to a standard axial reactor geometry as described in U.S. patent application Ser. No. 13/900,898, which is incorporated herein by reference in its entirety.

Example 10—Design of an Alkane Mixer

Figure 35:
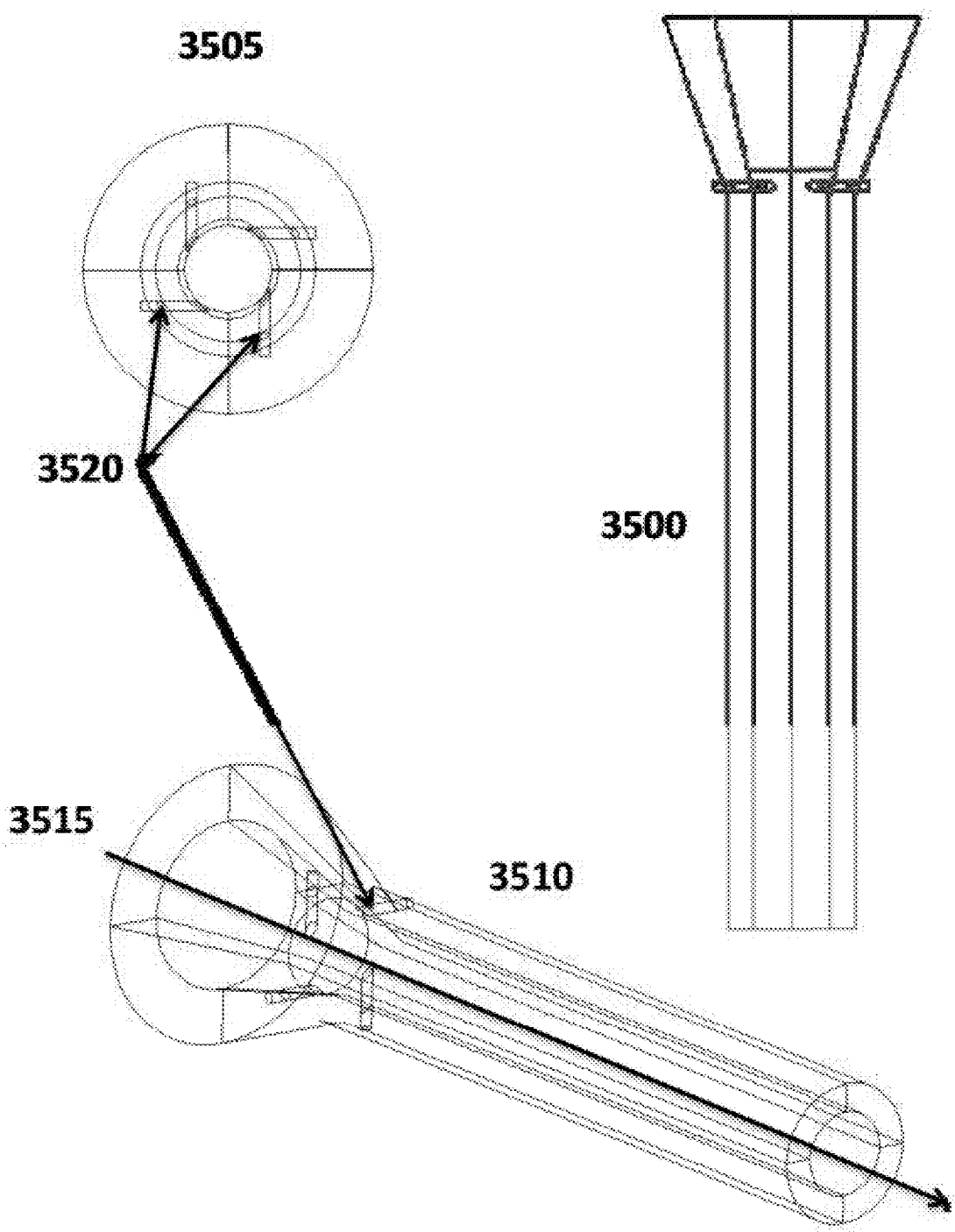
FIG. 35 shows an example of a mixer for injecting alkanes into an OCM reactor.
Figure 36:
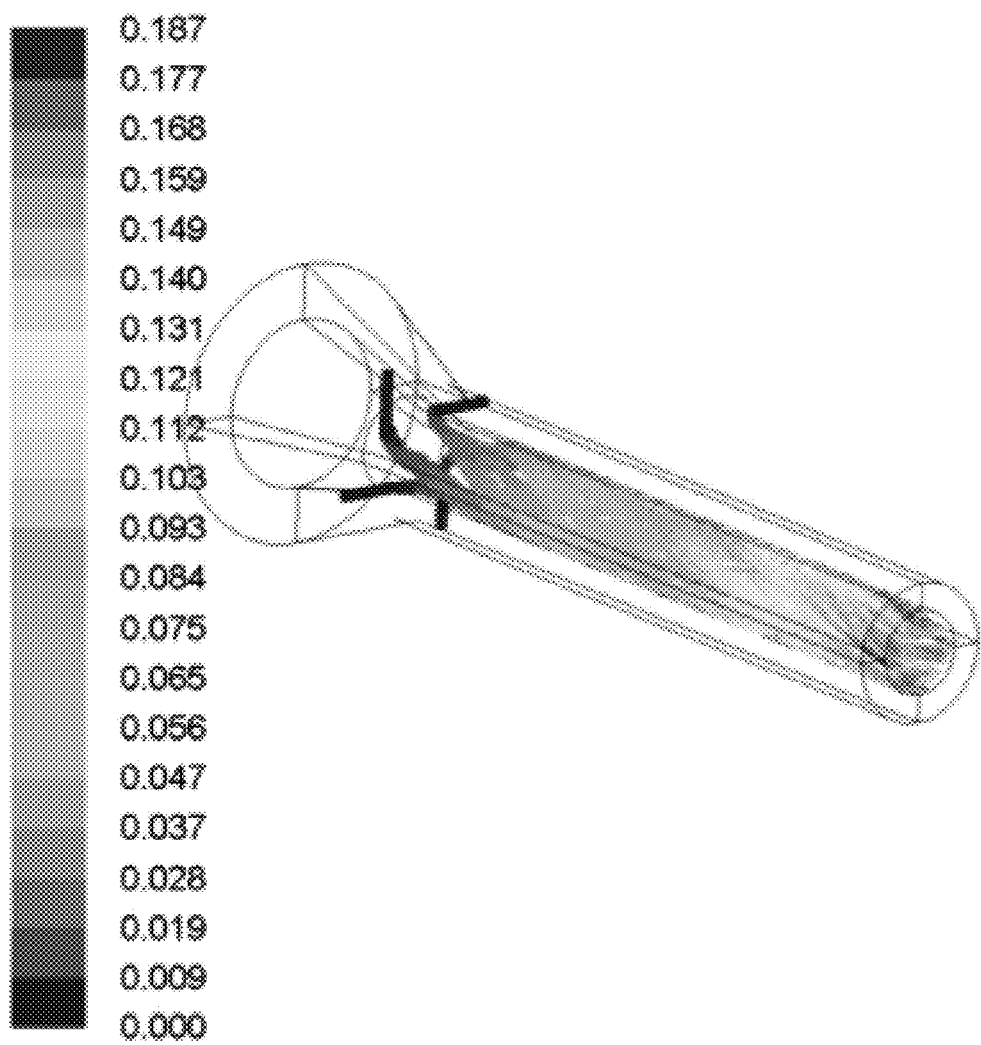
FIG. 36 shows an example of a simulation of gas flow through a mixer.

In some embodiments of the present disclosure, alkanes (e.g., ethane) is injected into the OCM reactor to be converted into ethylene using the heat of the OCM reaction. FIG. 35 shows an example of a mixer that can be used for alkane injection into the OCM reactor. The mixer is shown from a side profile view 3500, from an end view 3505 and from a perspective view 3510. The OCM product gas flows through the center of the mixer along its long axis (and optionally around the outside of the mixer) 3515. The alkane stream is injected into the mixer in a plurality directions perpendicular to the long axis 3520 and mixes with the OCM effluent as it travels down the center of the mixer along its long axis. FIG. 36 shows an example of a computational fluid dynamics (CFD) simulation of the mixing of the alkane with the OCM product gas.

Additional descriptions of OCM reactors, catalysts and processes that may be employed for use with devices, systems and methods of the present disclosure may be found in, for example, U.S. patent application Ser. No. 13/900,898, U.S. patent application Ser. No. 13/936,783, U.S. patent application Ser. No. 14/099,614, U.S. patent application Ser. No. 13/115,082, U.S. patent application Ser. No. 13/479,767, U.S. patent application Ser. No. 13/689,611, U.S. patent application Ser. No. 13/739,954, U.S. patent application Ser. No. 13/901,319, U.S. patent application Ser. No. 14/212,435, U.S. Provisional Patent Application 62/050,729, U.S. Provisional Patent Application 62/073,478, and U.S. Provisional Patent Application 62/051,779, each of which is incorporated herein by reference in its entirety.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A system for mixing two or more gas streams, comprising:
   (a) a conduit comprising a fluid flow path for a first gas;
   (b) a first gas distribution manifold comprising one or more openings that are distributed across said fluid flow path, wherein said first gas distribution manifold directs a second gas stream into said fluid flow path;

(c) a second gas distribution manifold comprising airfoil shaped manifolds that facilitate mixing such that said first gas and said second gas become uniformly mixed; and (d) a reactor bed in fluid communication with said fluid flow path, wherein said reactor bed comprises an oxidative coupling of methane catalyst.

2. The system of claim 1, wherein said first manifold and second manifold prevent flow separation within said mixer.

3. The system of claim 1, wherein said manifolds mix said first gas and said second gas within about 200 milliseconds.

4. The system of claim 1, wherein said reactor bed is in contact with at least a portion of said manifolds.

5. The system of claim 1, wherein each of said airfoil-shaped manifolds comprises a first end and a second end situated along said fluid flow path, wherein said one or more openings are disposed between said first end and said second end.

6. A reactor system for performing oxidative coupling of methane to generate hydrocarbon compounds containing at least two carbon atoms ($C_{2+}$ compounds), comprising:

(a) a mixer comprising (i) a conduit providing a fluid flow path for a first gas stream comprising methane and (ii) a plurality of airfoil-shaped manifolds distributed across said fluid flow path, wherein said airfoil-shaped manifolds inject a second gas stream comprising oxygen into said fluid flow path to provide a third gas stream comprising methane and oxygen; and (b) a catalyst that performs an oxidative coupling of methane (OCM) reaction using said third gas stream to produce a product stream comprising one or more $C_{2+}$ compounds.

7. The reactor system of claim 6, wherein said airfoil-shaped manifolds are in contact with said catalyst.

8. The reactor system of claim 6, wherein said reactor comprises at least two stages of mixer and catalyst.

9. The reactor systems of claim 8, wherein said reactor comprises a bypass leg directing a portion of said first gas stream to a mixer stage located after a first catalyst stage and before a second catalyst stage.

10. The reactor system of claim 6, wherein said reactor comprises an internal heat exchanger that is capable of transferring heat from said catalyst to said second gas stream prior to said second gas stream entering said mixer.

11. The reactor system of claim 6, wherein said airfoil-shaped manifolds uniformly mix said first and second gas streams to provide said third gas stream.

12. The reactor system of claim 6, wherein said catalyst is included in a catalyst bed.

13. The reactor system of claim 12, wherein at least a portion of said catalyst bed is in said mixer.

14. The reactor system of claim 12, wherein said catalyst bed is in a reactor downstream of said mixer.

15. A reactor system for performing oxidative coupling of methane to generate hydrocarbon compounds containing at least two carbon atoms ($C_{2+}$ compounds), comprising:

(a) a mixer capable of mixing a first gas stream comprising methane with a second gas stream comprising oxygen to provide a third gas stream;

(b) a catalyst that performs an oxidative coupling of methane (OCM) reaction using said third gas stream to produce a product stream comprising one or more C2+compounds, wherein said OCM reaction liberates heat; and (c) one or more flow reversal pipes in fluid communication with said mixer and at least partially surrounded by said catalyst, wherein said flow reversal pipes comprise an inner pipe circumscribed by an outer pipe along at least a portion of said length of said inner pipe, wherein said inner pipe is open at both ends and said outer pipe is closed at an end that is surrounded by said catalyst, wherein said flow reversal pipes are configured to transfer heat from said catalyst to said second gas stream during flow along said inner pipe and/or a space between said inner pipe and outer pipe.

16. The reactor of claim 15, wherein said second gas stream (i) flows through said inner pipe into said catalyst along a first direction and (ii) flows in a space between said inner pipe and outer pipe out of said catalyst along a second direction that is substantially opposite to said first direction.

17. The reactor of claim 15, wherein said second gas stream (i) flows through a space between said inner pipe and outer pipe and into said catalyst along a first direction and (ii) flows in said inner pipe and out of said catalyst along a second direction that is substantially opposite to said first direction.

18. A system for performing oxidative coupling of methane (OCM) reaction to generate hydrocarbon compounds containing at least two carbon atoms ($C_{2+}$ compounds), comprising:

(a) an OCM reactor comprising an OCM catalyst that facilitates an OCM reaction to generate said $C_{2+}$ compounds;

(b) an injector comprising a fluid flow conduit that directs a first gas stream through at least a portion of said OCM reactor to one or more openings that are in fluid communication with said OCM reactor, wherein said fluid flow conduit is in thermal communication with said OCM reactor, and wherein said first gas stream comprises one of methane and an oxidizing agent; and (c) a gas distribution manifold comprising one or more openings that are in fluid communication with said one or more openings of said injector and said OCM reactor, wherein said gas distribution manifold directs a second gas stream into said OCM reactor, which second gas stream comprises said other of methane and said oxidizing agent.

19. The system of claim 18, wherein said injector comprises one or more ribs each comprising one or more openings.

20. The system of claim 19, wherein said one or more ribs are airfoils.

* * * * *